(12) United States Patent
Hu et al.

(10) Patent No.: US 7,368,571 B2
(45) Date of Patent: *May 6, 2008

(54) HIV-INTEGRASE INHIBITORS, PHARMACEUTICAL COMPOSITIONS AND METHODS FOR THEIR USE

(75) Inventors: Qiyue Hu, Carlsbad, CA (US); Atsuo Kuki, Encinitas, CA (US); Dawn Marie Nowlin, San Diego, CA (US); Michael Bruno Plewe, San Diego, CA (US); Hai Wang, San Diego, CA (US); Junhu Zhang, San Diego, CA (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/470,301

(22) Filed: Sep. 6, 2006

(65) Prior Publication Data

US 2007/0004768 A1 Jan. 4, 2007

Related U.S. Application Data

(63) Continuation of application No. 10/699,068, filed on Oct. 30, 2003, now Pat. No. 7,135,482.

(60) Provisional application No. 60/422,513, filed on Oct. 31, 2002.

(51) Int. Cl.
*C07D 471/02* (2006.01)
*C07D 471/00* (2006.01)

(52) U.S. Cl. ...................... 546/113; 546/118
(58) Field of Classification Search ............... 546/113, 546/118
See application file for complete search history.

(56) References Cited

U.S. PATENT DOCUMENTS

| | | | |
|---|---|---|---|
| 4,371,536 A | 2/1983 | Braestrup et al. | |
| 5,010,077 A | 4/1991 | Braestrup et al. | |
| 5,262,537 A * | 11/1993 | Huang et al. ............... | 546/118 |
| 5,616,609 A | 4/1997 | Li et al. | |
| 5,726,203 A | 3/1998 | Ikekawa et al. | |
| 6,057,297 A | 5/2000 | Politi et al. | |
| 6,075,021 A | 6/2000 | Evanno et al. | |
| 6,395,743 B1 | 5/2002 | Heimbuch et al. | |
| 6,403,347 B1 | 6/2002 | Bills et al. | |
| 7,001,912 B2 | 2/2006 | Kuki et al. | |
| 7,135,482 B2 * | 11/2006 | Hu et al. ............... | 514/300 |
| 7,138,408 B2 | 11/2006 | Kuki et al. | |
| 2002/0123527 A1 | 9/2002 | Walker et al. | |

FOREIGN PATENT DOCUMENTS

| | | |
|---|---|---|
| EP | 0 030 254 | 10/1984 |
| EP | 1 086 101 | 3/2001 |
| EP | 1 209 158 | 5/2002 |
| EP | 1 375 486 | 1/2004 |
| GB | 2 209 032 | 4/1989 |
| GB | 2 271 566 | 4/1994 |
| GB | 2 306 476 | 5/1997 |
| GB | 2 327 674 | 2/1999 |
| JP | 2003-119137 | 4/2003 |
| JP | 2003-171381 | 6/2003 |
| WO | WO 98/18473 | 5/1998 |
| WO | WO00/68235 | 11/2000 |
| WO | WO 01/09114 | 2/2001 |
| WO | WO 02/02516 | 1/2002 |
| WO | WO 02/070491 | 9/2002 |
| WO | WO 03/033496 | 4/2003 |
| WO | WO 03/035076 | 5/2003 |
| WO | WO 03/047564 | 6/2003 |
| WO | WO 03/049690 | 6/2003 |
| WO | WO 03/062204 | 7/2003 |
| WO | WO 03/077850 | 9/2003 |
| WO | WO 03/082881 | 10/2003 |
| WO | WO 03/086319 | 10/2003 |
| WO | WO 2004/035076 | 4/2004 |
| WO | WO 2004/039803 | 5/2004 |
| WO | WO 2004/067531 | 8/2004 |
| WO | WO 2005/103003 | 11/2005 |
| WO | WO 2005/103051 | 11/2005 |
| WO | WO 2006/027694 | 3/2006 |

OTHER PUBLICATIONS

Abdel-Magid, A., et al., "Reductive Amination of Aldehydes and Ketones by Using Sodium Triacetoxyborohydride," *Tetrahedron Letters*, 1990, 5595-5598, vol. 31, No. 39.

Abdel-Magid, et al., "Reductive Amination of Aldehydes and Ketones with Sodium Triacetoxyborohydride. Studies on Direct and Indirect Reductive Amination Procedures," *Journal of Organic Chemistry*, 1996, 3849-3862, vol. 61.

(Continued)

*Primary Examiner*—Rita Desai
*Assistant Examiner*—John Mabry
(74) *Attorney, Agent, or Firm*—Steve T. Zelson; David L. Kershner

(57) ABSTRACT

Bicycling hydroxamate compounds represented by the Formula I:

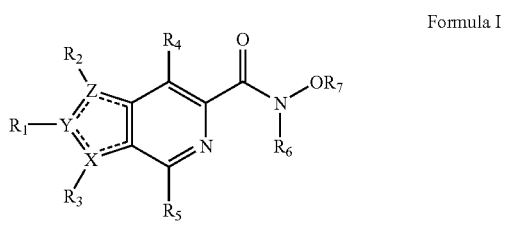

Formula I are described. The bicyclic hydroxamate compounds and compositions containing those compounds may be used to inhibit or modulate an enzyme activity of HIV Integrase and to treat HIV mediated diseases and conditions.

2 Claims, No Drawings

OTHER PUBLICATIONS

Amatore, C., et al., "Intimate Mechanism Of Oxidative Addition To Zerovalent Palladium Complexes In The Presence Of Halide Ions And Its Relevance To The Mechanism Of Palladium-Catalyzed Nucleophilic Substitutions," *J. Am. Chem. Soc.*, 1993, 9531-9541, vol. 115.

Bagshawe, K., "Antibody-Directed Enzyme Prodrug Therapy: A Review," *Drug Development Research*, 1995, 220-230, vol. 34.

Barbier, C., et al., "Preparation of Lavendamycin Analogues," *Heterocycles*, 2000, 37-48, vol. 53, No. 1.

Bertolini, et al., "A New Rational Hypothesis for the Pharmacophore of the Active Metabolite of Leflunomide, a Potent Immonsuppresive Drug," *Journal of Medicinal Chemistry*, 1997, 2011-2016, vol. 40.

Biere, H., et al., "Ein einfacher Zugang zum Pyrrolo[1,2-c]pyrimidin und Pyrrolo[3,2-c]pyridin-System," *Liebigs Ann. Chem.*, 1987, 491-497 (English Abstract Enclosed).

Bodor, "Novel Approaches to the Design of Safer Drugs: Soft Drugs and Site-Specific Chemical Delivery Systems," *Advances in Drug Research*, 1984, 255-331, vol. 13.

Butler, S., et al., "A Quantitative Assay for HIV DNA Integration in vivo," *Nature Medicine*, 2001, 631-634, vol. 7, No. 5.

Cain, M., et al., "Biomimetic Approach to Potential Benzodiazepine Agonists and Antagonists," *Heterocycles*, 1982, 1003-1007, vol. 19, No. 6.

Campbell, K., et al., "The Preparation of unsymmetrical Secondary Aliphatic Amines," *J. Am. Chem. Soc.*, 1944, 82-84, vol. 66.

Chen, B., et al., "Distinct Modes Of Human Immunodeficiency Virus Type 1 Proviral Latency Revealed By Superinfection Of Nonproductively Infected Cell Lines With Recombianant Luciferase-Encoding Viruses" *Journal Of Virology*, 1994, 654-660, vol. 68, No. 2.

Chen, J., et al., "Crystal structure of the HIV-1 integrase catalytic core and C-terminal domains: A model for viral DNA binding," *PNAS*, 2000, 8233-8238, vol. 97, No. 15.

Coker, J., et al., "The Cyanomethylation of Indole," *Journal of Organic Chemistry*, 1963, 589-590, vol. 28.

Dear, G., et al., "Mass directed peak selection, an efficient method of drug metabolite identification using directly coupled liquid chromatography—mass spectrometry—nuclear magnetic resonance spectroscopy," *Journal of Chromatography B*, 2000, 281-293, vol. 748.

Dekhane, M., et al., "A New Efficient Synthesis of Ethyl β-Carboline-3-Carboxylate (β-CCE) and Methyl 4-Methyl-β-Carboline-3-Carboxylate (4-Methyl-β-CCM) Starting from Indole-2-Carboxaldehyde," *Tetrahedron*, 1994, 6299-6306, vol. 50, No. 21.

Dekhane, M., et al., "A Practical Synthesis of 1h-Pyrrlo[2,3-c]Pyridine-5-Carboxylic Acid Derivatives From Pyrrole-2-Carboxaldehydes," *Tetrahedron*, 1993, 8139-8146, vol. 49, No. 36.

Dodd, R., et al., "Synthesis and Pharmacological Activity of a Pyrido [3',4':5,4]Pyrrolo[1,2-c]-[1,4] Benzodiazepine-3, 10-Dione, A New Benzodiazepine-β--Carboline Type Hybrid Molecule," *Heterocycles*, 1989, 1101-1113, vol. 28, No. 2.

Dodd, R., et al., "The Oxidation of Aromatic Aldehydes to Carboxylic Acids Using Hydrogen Peroxide in Formic Acid," *Synthesis*, 1993, 295-297.

Doisy, X., et al., "Synthesis And Benzodiazepine Receptor (ω Receptor) Affinities Of 3-Substituted Derivatives Of Pyrrolo[2,3-c]Pyridine-5-Carboxylate, A Novel Class of ω₁ Selective Ligands," *Bioorganic & Medicinal Chemistry*, 1999, 921-932, vol. 7.

Doyle, T., et al., "Nuclear Analogs of β-lactam Antibiotics. I. Synthesis of O-2-isocephams," *Can. J. Chem.*, 1977, 468-483, vol. 55.

Eberle, M., "Contribution to the Chemistry of Indole About the 5-(1-Indolyl)-2-pentanone System," *Journal of Organic Chemistry*, 1976, 633-636, vol. 41, No. 4.

Erofeev, Y., et al., "Introduction of 3-Indolymethyl Residues in Nitroacetic Acid Esters," *Khim. Get. Soed.*, 1978, 780.

Gilchrist, T., et al., "Synthesis of Fused Pyridines under Neutral Conditions," *J.C.S. Chem. Comm.*, 1979, 627-628.

Goldgur, Y., et al., "Structure Of the HIV-1 Integrase Catalytic Domain Complexed With An Inhibitor: A Platform For Antiviral Drug Design," *PNAS*, 1999, 13040-13043, vol. 96, No. 23.

Grobler, J., et al., "Diketo Acid Inhibitor Mechanism And HIV-1 Integrase: Implications For Metal Binding In The Active Site Of Phosphotransferase Enzymes," *PNAS*, 2002, 6661-6666, vol. 99, No. 10.

Guzman, F., et al., "Biomimetic Approach to Potential Benzodiazepine Receptor Agonists and Antagonists," *Journal of Medicinal Chemistry*, 1984, 564-570, vol. 27.

Hansen, M., et al., "Integration Complexes Derived From HIV Vectors For Rapid Assays In Vitro," *Nature Biotechnology*, 1999, 578-582, vol. 17, No. 6.

Hazuda, D., et al., "Discovery and Analysis of Inhibitors of the Human Immunodeficiency Integrase," *Drug Design and Discovery*, 1997, 17-24, vol. 15.

Henn, L., et al., "Formation of Indoles, Isoquinolines, and Other Fused Pyridines from Azidocrylates," *J. Chem. Soc. Perkin Trans.*, 1984, 2189-2196, vol. 1.

Ho, B., et al. "Inhibitors of Monoamine Oxidase: Influence of Methyl Substitution on the Inhibitory Activiy of beta-Carbolines," *J. Pharm.Sci.*, 1968, 269-274, vol. 57, No. 2.

Ho, B., et al., "Inhibitors of Monoamine Oxidase III: 9-Substituted beta-Carbolines," *J.Pharm Sci.*, 1969, 219-221, vol. 58, No. 2.

Hughes, L., et al., "Progress In The Mitsunobu Reaction, A Review," *Organic Preparations And Procedures Int.*, 1996, 127-164, vol. 28, No. 2.

Jenkins, T., et al., "A Soluble Active Mutant of HIV-1 Integrase," *Journal of Biological Chemistry*, 1996, 7712-7718, vol. 271, No. 13.

Kantlehner, W., et al., "Umsetzungen von tert-Butoxy-$N,N,N^1,N^1$-tetramethylmethandiamin mit NH- und CH-aciden Verbingdungen," *Liebigs Ann. Chem.*, 1980, 344-357 (English Abstract Enclosed).

Kelley, J., et al., "Attempted Inhibition of Histidine Decarboxylase with β-Alkyl Analogues of Histidine," *Journal of Medicinal Chemistry*, 1977, 721-723, vol. 20, No. 5.

Knight, D., et al., "On The diverse Outcomes Of Base-Induced Cyclisations Of 2-Alkynylphenylhydroxamic Acids," *Tetrahedron Letters*, 2002, 9187-9189, vol. 43.

Kozikowski, A., et al., "Use of N,N-Dimethyl(Methylene)Ammonium Chloride in the Functionalization of Indoles," *Heterocycles*, 1980, 55-58, vol. 14, No. 1.

Kreher, R., et al., "Cyclisierende Kondensation von 1H-Pyrrol-3,4-dicarbaldehyden mit 1,2-bifunktionellen Verbindungen [1]," *Chemiker-Zeitung*, 1984, 275-277, vol. 108, No. 9 (English Abstract Enclosed).

Krutosikova, A., et al., "Condensed O-, N-Heterocycles by the Transformation of Azidoacrylates," *Monatsh. Chem.*, 1992, p. 807-815, vol. 123.

Lane, C., "Sodium Cyanoborohydride—A Highly Selective Reducing Agent for Organic Functional Groups," *Synthesis*, 1975, 135-146.

Lee, J., et al.,"Aromatization of Cyclohexenes and Cyclohexadienes With Selenium Dioxide-Trimethylsilyl Polyphosphate," *Tetrahedron Letters*, 1992, 6363-6366, vol. 33, No. 42.

Lewin, S., et al., "Use Of Real-Time PCR And Molecular Beacons To Detect Virus Replication In Human Immunodeficiency Virus Type 1-Infected Individuals On Prolonged Effective Antiretroviral Therapy," *Journal of Virology*, 1999, 6099-6103, vol. 73, No. 7.

Little, S., et al., "Antiretroviral Effect Of L-000870810, A Novel HIV-1 Integrase Inhibitor, In HIV-1 Infected Patients," 12th Conference On Retroviruses And Opportunistic Infections, Feb. 2005, Abstract 161.

Lyttle, D., et al., "The Chemistry of Nitroacetic Acid and its Esters. I. The Alkylation of Alkyinitroacetates with Gramine," *J. Am. Chem. Soc.*, 1947, 2118-2119, vol. 69.

Mataka, S., et al., "Condensation Reaction of 3,4-Dibenzoyl-1-methyl-2,5-diphenylpyrrole and—1-phenylpyrazole with Methylamine Derivatives Affording Pyrrolo [3,4-c]pyridine and 2H-Pyrazolo[3,4-c]- and [4,3-c]pyridines," *J. Heterocyclic. Chem.*, 1981, 1073-1075, vol. 18.

Mehta, A., et al., "Ortho-Directed Lithiation Studies of 3-Carboxy-beta-carbolines," *J. Org. Chem.*, 1993, 7587-7590, vol. 58.

Molina, P., et al., "An Efficient Iminophosphorane-Mediated Synthesis of Thieno[3,2-c]pyridine, Thieno[2,3-c]pyridine and Furo[3,2-c]-pyridine Derivatives," *Synthesis*, 1987, p. 45-48.

Molina, P., et al., "Pyrido Annelation Reaction by a Tandem Aza Wittig/Electro-cyclic Ring-Closure Strategy: Preparation of Pyrazolo [4,3-c]- and Pyrazolo[3,4-c]pyridine Derivatives," *Tetrahedron*, 1991, 6737-6746, vol. 47, No. 33.

Neef, G., et al., "Synthesis of 4-Substituted β-Carbolines," *Heterocycles*, 1983, 1295-1313, vol. 20, No. 7.

Pais, G., et al., "Structure Activity Of 3-Aryl-1,3-Diketo-Containing Compounds As HIV-1 Integrase Inhibitors," *J. Med. Chem.*, 2002, 3184-3194, vol. 45.

Prokopov, A., et al., "Synthesis of 6-Azaindole," *Khim. Geterotsikl. Soedin.*, 1977, 919.

Prox, A., et al., "Rapid Structure Elucidation of Drug Metabolites by use of Stable Isotopes," *Xenobiotica.*, 1973, 103-112, vol. 3, No. 2.

Quandil, A., et al., "Synthesis And Pharmacological Evaluation Of Substituted Naphth[2,3-de]isoquinolines (Dinapsoline Analogues) As $D_1$ and $D_2$ Dopamine Receptor Ligands," *Bioorganic & Medicimal Chemistry*, 2003, 1451-1464, vol. 11.

Rousseau, J., et al., "Synthesis of 3-Deaza-β-hydroxyhistidine Derivatives and Their Use for the Preparation of Substituted Pyrrolo[2,3-c]pyridine-5-carboxylates via the Pictet-Spengler Reaction," *Journal of Organic Chemistry*, 1998, 2731-2737, vol. 63.

Sakamoto, T., et al., "Condensed Heteroaromatic Ring Systems. XVIII.[1] Palladium-Catalyzed Cross-Coupling Reaction Of Aryl Bromides With (z)-1-Ethoxy-2-Tributylstannylethene And Its Utilization For Construction Of Condensed Heteroaromatics," *Tetrahedron*, 1991, 1877-1886,, vol. 47, No. 10-11.

Sakamoto, T., et al., "Condensed Heteroaromatic Ring Systems. XXXI.[1)], Synthesis Of Pyrrolo[2,3-d]Pyrimidines And Pyrrolo[3,2-d]Pyrimidines," *Chem. Pharm. Bull.*, 1993, 81-86, vol. 41, No. 1.

Sandrin, J., et al., "Pictet-Spengler Condensations In Refluxing Benzene," *Heterocycles*, 1976, 1101-1104, vol. 4, No. 6.

Sayasith, K., et al., "Targeting HIV-1 Integrase," *Expert Opinion Ther. Targets*, 2001, 443-464, vol. 5, No. 4.

Schlecker, W., et al., "Synthesis of 4-arylpyridines and Substituted beta-Carbolines," *Tetrahedron*, 1995, 9531-9542, vol. 51, No. 35.

Scott, W., et al., "Palladium-Catalyzed Coupling Of Vinyl Triflates With Organostannanes. Synthetic And Mechanistic Studies" *J. Am. chem. Soc.*, 1986, 3033-3040, vol. 108.

Settimj, G., et al, "β-/carbolines as Agonistic or Antagonistic Benzodiazepine Receptor Ligands. 1. Synthesis of some 5, 6-and 7-Amino Derivatives of 3-Methoxycarbonyl-β-carboline (βCCM) and of 3-ethoxycarbonyl-β-Carboline (βCCE,)" *J. Heterocycl. Chem.*, 1988, 1391-1397, vol. 25.

Shafiee, A., et al., "Synthesis of 2-Aryl-6-carbethoxythiazolo[4,5-c]pyridine and 7-Chloro-2-phenylthiazolo[5,4-c]pyridine [1]," *J. Heterocyclic Chem.*, 1986, 1171-1173, vol. 23

Shan, D., et al., "Prodrug Strategies Based on Intramolecular Cyclization Reactions," *Journal of Pharmaceutical Science*, 1997, 765-767, vol. 86, No. 7.

Singh, S., et al., "Ethyl α-Amino-β,β-Diethoxypropionate, a Useful Synthon for the Preparation of 3,4-Fused Pyridine-6-Carboxylates from Aromatic Aldehydes," *Heterocycles*, 1997, 379-391, vol. 44, No. 1.

Snyder, H., et al., "The Synthesis of the 2-Amino-3-(3-indolyl)-butyric Acids(β-Methyltryptophans)," *J. Am. Chem. Soc.*, 1957, 2217-2221, vol. 79.

Soerens, D., et al., "Study of the Pictet-Spengler Reaction in Aprotic Media: Synthesis of the β-Galactosidase Inhibitor, Pyridindolol," *Journal of Organic Chemistry*, 1979, 535-545, vol. 44, No. 4.

Spraul, M., et al., "Liquid chromatography coupled with high-field proton NMR for profiling human urine for endogenous compounds and drug metabolites," *Journal of Pharmaceutical & Biomedical Analysis*, 1992, 601-605, vol. 10, No. 8.

Still, W., et al., "Rapid Chromatographic Technique for Preparative Separations with Moderate Resolution," *Journal of Organic Chemistry*, 1978, 2923-2925, vol. 43, No. 14.

Stille, J., et al., "," Angew. Chem., 1986, 504, vol. 98.

Stille, J., et al., "The Palladium-Catalyzed Cross-Coupling Reactions Of Organotin Reagents With Organic Electrophiles," *Angew. Chem. Int. Ed. Engl.*, 1986, 508-524, vol. 25.

Sundberg, R., et al., "Syntheses with N-Protected 2-Lithioindoles," *Journal of Organic Chemistry*, 1973, 3324-3330, vol. 38, No. 19.

Terwilliger, E., et al., "Construction And Use Of A Replication-Competent Human Immunodeficiency Virus (HIV-1) That Expresses The Chloramphenicol Acetyltransferase Enzyme," *PNAS*, 1989, 3857-3861, vol. 86.

Trout, G., et al., "Synthesis of Some Histidine Analogs and Their Effect on the Growth of a Histidine-Requiring Mutant of *Leuconostoc mesenteroides*," *Journal of Medicinal Chemistry*, 1972, 1259-1261, vol. 15, No. 12.

Wai, J., et al., "4-Aru;-2,4-Dioxobutanoic Acid Inhibitors Of HIV-1 Integrase And Viral Replication In Cells," *Journal of Medicinal Chemistry*, 2000, 4923-4926, vol. 43, No. 26.

Weislow, O., et al., "New Soluble-Formazan Assay For HIV-1 Cytopathic Effects; Application To High-Flux Screening Of Synthetic And Natural Products For AIDS-Antiviral Activity," *Journal Of The National Cancer Institute*, 1989, 577-586, vol. 81, No. 8.

Young, S., et al., "Inhibition Of HIV-1 Integrase By Small Molecules: The Potential For A New Class Of AIDS Chemotherapeutics," *Current Opinion Drug Discovery & Development*, 2001, 402-410, vol. 4, No. 4.

Young, S., et al., "L-870, 810: A Potent Antiviral HIV Integrase Inhibitor with Potential Clinical Utility," *Poster presented at International AIDS Conference*, Barcelona, (Jul. 7-12, 2002).

* cited by examiner

HIV-INTEGRASE INHIBITORS, PHARMACEUTICAL COMPOSITIONS AND METHODS FOR THEIR USE

This application is a continuation of U.S. patent application Ser. No. 10/699,068, filed Oct. 30, 2003 now U.S. Pat. No. 7,135,482, which claims priority from U.S. patent application Ser. No. 60/422,513, filed Oct. 31, 2002, all of which are hereby incorporated by reference in their entirety.

The present invention is directed to bicyclic hydroxamates and pharmaceutically acceptable salts, pharmaceutically acceptable prodrugs, and pharmaceutically acceptable metabolites thereof, their synthesis, and their use as modulators or inhibitors of the HIV Integrase enzyme. The compounds of the present invention are useful for modulating (e.g. inhibiting) an enzyme activity of HIV Integrase enzyme and for treating diseases or conditions mediated by human immunodeficiency virus ("HIV"), such as for example, acquired immunodeficiency syndrome ("AIDS"), and AIDS related complex ("ARC").

BACKGROUND OF THE INVENTION

The retrovirus designated "human immunodeficiency virus" or "HIV" is the etiological agent of a complex disease that progressively destroys the immune system. The disease is known as acquired immune deficiency syndrome or AIDS. AIDS and other HIV-caused diseases are difficult to treat due to the ability of HIV to rapidly replicate, mutate and acquire resistance to drugs. To attempt to slow the spread of the virus after infection, treatment of AIDS and other HIV-caused diseases has focused on inhibiting HIV replication.

Since HIV is a retrovirus, and thus, encodes a positive-sense RNA strand, its mechanism of replication is based on the conversion of viral RNA to viral DNA, and subsequent insertion of the viral DNA into the host cell genome. HIV replication relies on three constitutive HIV encoded enzymes: reverse transcriptase (RT), protease and integrase.

Upon infection with HIV, the retroviral core particles bind to specific cellular receptors and gain entry into the host cell cytoplasm. Once inside the cytoplasm, viral RT catalyzes the reverse transcription of viral ssRNA to form viral RNA-DNA hybrids. The RNA strand from the hybrid is then partially degraded and a second DNA strand is synthesized resulting in viral dsDNA. Integrase, aided by viral and cellular proteins, then transports the viral dsDNA into the host cell nucleus as a component of the pre-integration complex (PIC). In addition, integrase provides the permanent attachment, i.e., integration, of the viral dsDNA to the host cell genome which, in turn, provides viral access to the host cellular machinery for gene expression. Following integration, transcription and translation produce viral precursor proteins. Protease then cleaves the viral precursor proteins into viral proteins which, after additional processing, are released from the host cell as newly infectious HIV particles.

A key step in HIV replication, insertion of the viral dsDNA into the host cell genome, is believed to be mediated by integrase in at least three, and possibly, four, steps: (1) assembly of proviral DNA; (2) 3'-end processing causing assembly of the PIC; (3) 3'-end joining or DNA strand transfer, i.e., integration; and (4) gap filling, a repair function. See, e.g., Goldgur, Y. et al., *PNAS* 96(23): 13040-13043 (November 1999); Sayasith, K. et al., *Expert Opin. Ther. Targets* 5(4): 443-464 (2001); Young, S. D., *Curr. Opin. Drug Disc. & Devel.* 4(4): 402-410 (2001); Wai, J. S. et at., *J. Med. Chem.* 43(26): 4923-4926 (2000); Debyser, Z. et al., *Assays for the Evaluation of HIV-1 Integrase Inhibitors*, from *Methods in Molecular Biology* 160: 139-155, Schein, C. H. (ed.), Humana Press Inc., Totowa, N.J. (2001); and Hazuda, D. et al., *Drug Design and Disc.* 13:17-24 (1997).

In the first step, integrase forms a stable complex with the viral long terminal repeat (LTR) regions. Once the complex is formed, integrase then performs an endonucleolytic processing step whereby the terminal GT dinucleotides of the 3' ends (immediately downstream from a conserved CA dinucleotide) of both DNA strands are cleaved. The processed DNA/integrase complex (the PIC) then translocates across the nuclear membrane. Once inside the host cell nucleus, integrase performs the third step, 3'-end joining, whereby a cut is made in the host cell DNA to covalently join the processed 3'-ends of the viral processed DNA during two transesterification reactions. In the fourth step, cellular enzymes repair the resultant gap at the site of viral DNA insertion. The enzymes, if any, employed in the repair process have not been accurately identified. Sayasith, K. et al., *Expert Opin. Ther. Targets* 5(4): 443-464 (2001). Thus, the role that integrase plays in the gap filling function is not known.

It is clear that the role that integrase plays in the integration of the viral DNA into the host cell genome occurs through well-ordered reactions directed by various viral and cellular factors. This knowledge provides a variety of opportunities to block the essential step of integration (and the essential enzyme integrase) in the HIV life cycle.

Currently, AIDS and other HIV-caused disease are treated with an "HIV cocktail" containing multiple drugs including RT and protease inhibitors. However, numerous side effects and the rapid emergence of drug resistance limit the ability of the RT and protease inhibitors to safely and effectively treat AIDS and other HIV-caused diseases. In view of the shortcomings of RT and protease inhibitors, there is a need for another mechanism through which HIV replication can be inhibited. Integration, and thus integrase, a virally encoded enzyme with no mammalian counterpart, is a logical alternative. See, e.g., Wai, J. S. et al., *J. Med. Chem.* 43:4923-4926 (2000); Grobler, J. et al., *PNAS* 99: 6661-6666 (2002); Pais, G. C. G. et al., *J. Med. Chem.* 45: 3184-3194 (2002); Young, S. D., *Curr. Opin. Drug Disc. & Devel.* 4(4):402-410 (2001); Godwin, C. G. et al., *J. Med. Chem.* 45:3184-3194 (2002); Young, S. D. et al., "L-870, 810: Discovery of a Potent HIV Integrase Inhibitor with Potential Clinical Utility," Poster presented at the XIV International AIDS Conference, Barcelona (Jul. 7-12, 2002); and WO 02/070,491.

It has been suggested that for an integrase inhibitor to function, it should inhibit the strand transfer integrase function. See, e.g., Young, S. D., *Curr. Opin. Drug Disc. & Devel.* 4(4): 402-410 (2001). Thus, there is a need for HIV inhibitors, specifically, integrase inhibitors, and, more specifically, strand transfer inhibitors, to treat AIDS and other HIV-caused diseases. The inventive agents disclosed herein are novel, potent and selective HIV-integrase inhibitors, and, more specifically, strand transfer inhibitors, with high antiviral activity and low toxicity.

The references made to published documents throughout this application more fully describe the state of the art to which this invention pertains. The disclosures of these references are hereby incorporated by reference in their entireties.

SUMMARY OF THE INVENTION

The invention is directed to compounds represented by Formula I:

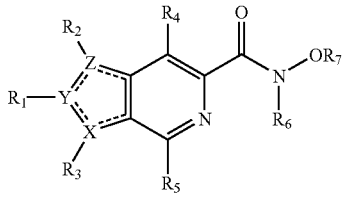

Formula I wherein:

$R_1$, $R_2$ and $R_3$ are each independently:

hydrogen; —C(O)O$R_c$; or an alkyl, alkenyl, heteroalkyl, or haloalkyl group, unsubstituted or substituted with one or more substituents independently selected from the group consisting of:

halogens; —O—; —O$R_c$; $NR_cR_c$; C(O)$NR_cR_c$; $NR_cC(O)NR_cR_c$; $NR_cC(O)R_c$; $NR_cC(NR_c)NR_cR_c$; $SR_c$; S(O)$R_c$; S(O)$_2R_c$; S(O)$_2NR_cR_c$; and alkyl, aryl, cycloalkyl, heteroaryl, and alkoxy-heteroaryl groups, unsubstituted or substituted by one or more substituents independently selected from the group consisting of:

halogens; —C($R_c$)$_3$; —OH; and alkyl, alkenyl, aryl and heteroaryl groups, unsubstituted or substituted with one or more independently selected $R_c$ groups, where $R_c$ is one or more substituents independently selected from the group consisting of: halogens; hydrogen; OH; unsubstituted alkyl; unsubstituted alkenyl; unsubstituted alkynyl; unsubstituted aryl; unsubstituted cycloalkyl; unsubstituted heterocycloalkyl; unsubstituted heteroaryl; aryl and heteroaryl groups substituted with one or more substituents independently selected from the group consisting of halogen and alkyl; or two or more $R_c$ groups together cyclize to form part of a heteroaryl or heterocycloalkyl group unsubstituted or substituted with an unsubstituted alkyl group;

$R_4$ is hydrogen or an alkyl, alkenyl, alkynyl, heteroalkyl, or haloalkyl group, unsubstituted or substituted with —O$R_d$ where $R_d$ is an unsubstituted alkyl group;

$R_5$ is hydrogen or an alkyl, alkenyl, alkynyl, heteroalkyl, or haloalkyl group;

$R_6$ is hydrogen or an alkyl, alkenyl, alkynyl, heteroalkyl, or haloalkyl group, unsubstituted or substituted with an aryl group;

$R_4$ and $R_6$ together with the N to which $R_6$ is attached cyclize to form the following compound represented by the Formula Id:

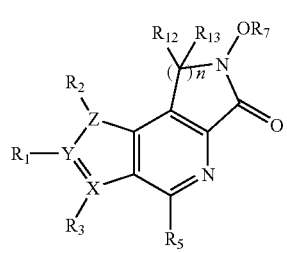

Formula Id wherein $R_{12}$ and $R_{13}$ are each independently:

hydrogen; —C(O)O$R_c$; or an alkyl, alkenyl, heteroalkyl, or haloalkyl group, unsubstituted or substituted with one or more substituents independently selected from the group consisting of:

halogens; —O—; —O$R_c$; $NR_cR_c$; C(O)$NR_cR_c$; $NR_cC(O)NR_cR_c$; $NR_cC(O)R_c$; $NR_cC(NR_c)NR_cR_c$; $SR_c$; S(O)$R_c$; S(O)$_2R_c$; S(O)$_2NR_cR_c$; and alkyl, aryl, cycloalkyl, heteroaryl, and alkoxy-heteroaryl groups, unsubstituted or substituted by one or more substituents independently selected from the group consisting of:

halogens; —C($R_c$)$_3$; —OH; and alkyl, alkenyl, aryl and heteroaryl groups, unsubstituted or substituted with one or more independently selected $R_c$ groups, where $R_c$ is one or more substituents independently selected from the group consisting of: halogens; hydrogen; unsubstituted alkyl; unsubstituted alkenyl; unsubstituted alkynyl; unsubstituted aryl; unsubstituted cycloalkyl; unsubstituted heterocycloalkyl; unsubstituted heteroaryl; aryl and heteroaryl groups substituted with one or more substituents independently selected from the group consisting of halogen and alkyl; or two or more $R_c$ groups together cyclize to form part of a heteroaryl or heterocycloalkyl group unsubstituted or substituted with an unsubstituted alkyl group; and n is 1, 2 or 3;

$R_7$ is hydrogen or an alkyl, alkenyl, alkynyl, heteroalkyl, haloalkyl, aryl, cycloalkyl, heterocycloalkyl or heteroaryl group, unsubstituted or substituted with one or more substituents independently selected from the group consisting of:

halogens; and aryl, cycloalkyl, heterocycloalkyl, and heteroaryl groups, unsubstituted or substituted with one or more halogen groups;

X is C or N;

Y is C or N;

Z is C or N; and there is a double bond between X and the 6-membered ring and Z and the 6-membered ring; or between X and Y; or between Y and Z;

or a pharmaceutically acceptable salt, pharmaceutically acceptable prodrug, or a pharmaceutically active metabolite thereof.

In another aspect, the invention is directed to compounds represented by Formula I:

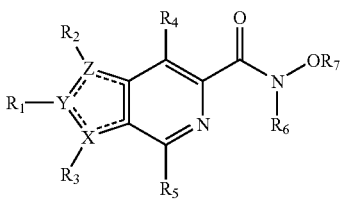

Formula I wherein:

$R_1$ is hydrogen or —C(O)O$R_c$, where $R_c$ is an unsubstituted alkyl, unsubstituted alkenyl, or unsubstituted alkynyl group;

$R_2$ is hydrogen or an alkyl, alkenyl, or heteroalkyl group, unsubstituted or substituted with one or more substituents independently selected from the group consisting of:

—O—; —NR_dR_d; —OR_d; halogens; and an aryl group, unsubstituted or substituted with one or more substituents independently selected from the group consisting of:
  halogens; —C(R_d)_3; unsubstituted alkyl, alkyl-R_d, alkenyl-R_d, and aryl groups, where R_d is one or more substituents independently selected from the group consisting of hydrogen; unsubstituted alkyl, unsubstituted alkenyl, and unsubstituted aryl groups;

R_3 is hydrogen or an alkyl, alkenyl, or heteroalkyl group, unsubstituted or substituted with one or more substituents independently selected from the group consisting of:
  —O—; —OR_e; and, alkyl, aryl, cycloalkyl, and heteroaryl groups, unsubstituted or substituted with one or more substituents independently selected from the group consisting of:
    halogens; —OH; and aryl or heteroaryl groups, substituted with one or more R_e substituents, where R_e is one or more substituents independently selected from the group consisting of halogens; hydrogen; OH; unsubstituted alkyl; and aryl unsubstituted or substituted with one or more substituents independently selected from the group consisting of halogen and alkyl;

R_4 is hydrogen or an alkyl group, unsubstituted or substituted with —OR_f, where R_f is an unsubstituted alkyl group;

R_5 is hydrogen or an alkyl group;

R_6 is hydrogen or an alkyl group unsubstituted or substituted with an aryl group;

R_4 and R_6 together with the N to which R_6 is attached cyclize to form the following compound represented by the Formula Id:

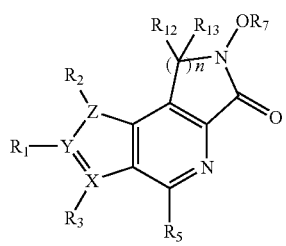

Formula Id wherein R_12 and R_13 are each independently hydrogen; and
n is 1;

R_7 is hydrogen or an alkyl alkenyl, or aryl group, unsubstituted or substituted with an aryl group, unsubstituted or substituted with one or more halogens;

X is C or N;

Y is C;

Z is C or N; and there is a double bond between X and the 6-membered ring and Z and the 6-membered ring; or between X and Y; or between Y and Z;

or a pharmaceutically acceptable salt, pharmaceutically acceptable prodrug, or a pharmaceutically active metabolite thereof.

In yet another aspect, the invention is directed to compounds of the Formula I:

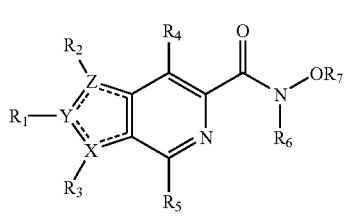

Formula I where
R_1 is hydrogen or —C(O)O-ethyl;

R_2 is hydrogen, methyl, ethyl, propyl, vinyl, allyl, or benzyl, unsubstituted or substituted with one or more substituents independently selected from the group consisting of:
  halogens, —O—, OH, amino, and phenyl, unsubstituted or substituted with one or more substituents selected from the group consisting of:
    methyl, ethyl, phenyl, benzyl, 2-phenylethyl, 3-phenylallyl, and 2-phenylvinyl;

R_3 is methyl, ethyl, butyl, or benzyl, unsubstituted or substituted with one or more substituents independently selected from the group consisting of:
  halogens, OH, methyl, cyclohexyl, —O—, thiadiazole, thiophenyl, and phenoxy, unsubstituted or substituted with one or more substituents independently selected from the group consisting of:
    halogens, phenyl, and ethoxy;

R_4 is hydrogen, methyl or methoxymethyl;

R_5 is hydrogen or methyl;

R_6 is hydrogen, methyl, or benzyl;

R_7 is hydrogen, methyl, benzyl, phenyl, allyl, or tert-butyl, unsubstituted or substituted with one or more halogens; and R_4 and R_6 together with the N to which R_6 attaches cyclize to form a pyrrole-2-one.

The invention is also directed to compounds having the Formula I:

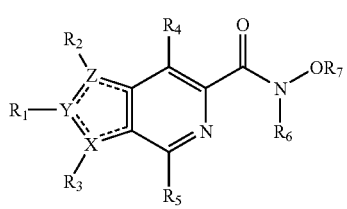

Formula I where
R_1 is hydrogen or —C(O)O-ethyl;

R_2 is selected from hydrogen; hydroxymethyl; methoxymethyl; ethoxymethyl; 2-phenylvinyl; 3-phenylprop-1-enyl; [(2-phenylvinyl)oxy]methyl; dimethylaminomethyl; benzyloxymethyl; 4-fluorobenzyl; 2-phenylvinyl; 2-phenylethyl; 3-phenylpropyl; 2-phenylethoxymethyl; [(phenylprop-2-enyl)oxy]methyl; [(3-phenylallyl)oxy]methyl; methyl; ethyl; and allyl;

R_3 is selected from hydrogen; 2,4-difluorobenzyl; 2,3-difluorobenzyl; 4-fluorobenzyl; 3-chloro-2,6-difluorobenzyl; 3-chloro-5-fluoro-2-hydroxybenzyl; 5-chloro-thiophen-2-ylmethyl; 3-chloro-2-fluorobenzyl; 2,3-dichlorobenzyl;

5-ethoxy-[1,2,3]thiadiazol-4-ylmethyl; 3-methyl-butyl; 2-cyclohexyl-ethyl; 2,4-difluoro-phenoxymethyl; 3,5-difluoro-2-hydroxybenzyl; 2-chloro-4-fluoro-phenoxymethyl; 3-chloro-5-fluoro-2-hydroxybenzyl; 4-fluoro-phenoxymethyl; 5-fluoro-2-hydroxy-benzyl; 2,3,4-trifluoro-phenoxymethyl; 3,4,5-trifluoro-2-hydroxybenzyl; 2-chloro-phenoxymethyl; and 5-chloro-2-hydroxy-benzyl;

$R_4$ is hydrogen, methyl or methoxymethyl;

$R_5$ is hydrogen or methyl;

$R_6$ is hydrogen, methyl, or benzyl;

$R_7$ is hydrogen, methyl, benzyl, phenyl, pentafluorobenzyl, allyl, tert-butyl; and $R_4$ and $R_6$ together with the N to which $R_6$ attaches cyclize to form a pyrrol-2-one.

Inventive compounds represented by the Formula I include, but are not limited to, the following compounds represented by Formula Ia, Ib, Ic and Ie:

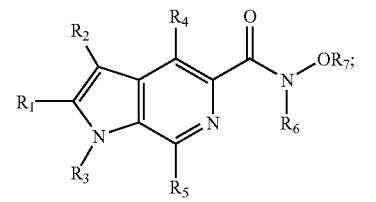

Formula Ia

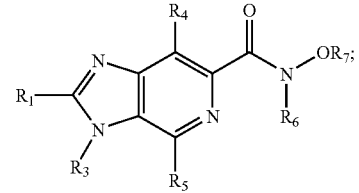

Formula Ib

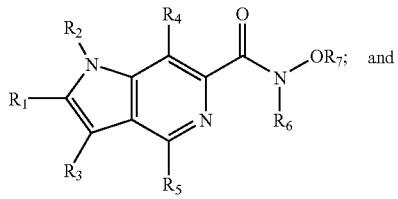

Formula Ic

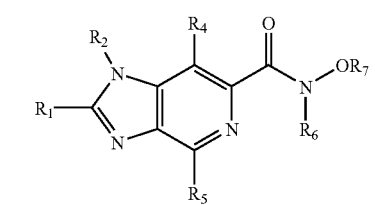

Formula Ie

In addition to compounds of Formula I, (including Formula Ia, Ib, Ic and Ie), the invention is also directed to pharmaceutically acceptable salts, pharmaceutically acceptable prodrugs, and pharmaceutically active metabolites of such compounds, and pharmaceutically acceptable salts of such metabolites. Such compounds, salts, prod rugs and metabolites are at times collectively referred to herein as "HIV Integrase agents."

The invention also relates to pharmaceutical compositions each comprising a therapeutically effective amount of an HIV Integrase agent of the invention in combination with a pharmaceutically acceptable carrier, diluent, or carrier therefore.

Additionally, the invention is directed to methods of inhibiting or modulating an enzyme activity of HIV Integrase, comprising contacting the enzyme with an effective amount of at least one HIV Integrase agent.

The invention also relates to methods of treating a disease or condition mediated by HIV, comprising administering to a mammal in need of such treatment a therapeutically effective amount of at least one HIV Integrase agent. The disease or condition mediated by HIV may be, for example, AIDS or ARC.

In another aspect, the invention is directed to methods of evaluating the HIV integrase modulatory activity of a test compound, comprising:

a) immobilizing viral DNA on a surface, wherein the viral DNA has been modified to contain a CA base pair overhang at the 5' end;

b) adding integrase to the immobilized DNA;

c) adding a test compound to the immobilized viral DNaintegrase mixture;

d) obtaining target DNA radiolabeled at both 3' ends of the ds-DNA;

e) combining the immobilized viral DNA/integrase/compound mixture with the radiolabeled target DNA to initiate a reaction;

f) stopping the reaction by adding a stop buffer to the combination of (e); and g) reading the assay results in a scintillation counter to determine whether the test compound modulates the activity of the integrase.

Other aspects, features, and advantages of the invention will become apparent from the detailed description of the invention and its preferred embodiments.

DETAILED DESCRIPTION OF THE INVENTION AND PREFERRED EMBODIMENTS

The compounds of Formula I are useful for modulating or inhibiting HIV Integrase enzyme. More particularly, the compounds of Formula I are useful as modulators or inhibitors of HIV Integrase activity, and thus are useful for the prevention and/or treatment of HIV mediated diseases or conditions (e.g., AIDS, and ARC), alone or in combination with other known antiviral agents.

Definitions

As used herein, the terms "comprising" and "including" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, neo-pentyl, hexyl, isohexyl, and the like.

The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary alkyl amines, alkyl sulfides, and the like.

The term "alkenyl" refers to a straight- or branched-chain alkenyl group having from 2 to 12 carbon atoms in the chain. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain.

Illustrative alkynyl groups include prop-2-ynyl, but-2-ynyl, but-3-ynyl, 2-methylbut-2-ynyl, hex-2-ynyl, and the like.

The term "haloalkyl" refers to a straight- or branched-chain alkyl or alkenyl group having from 2-12 carbon atoms in the chain and where one or more hydrogens is substituted with a halogen. Illustrative haloalkyl groups include trifluoromethyl, 2-bromopropyl, 3-chlorohexyl, 1-iodo-isobutyl, and the like.

The term "aryl" (Ar) refers to a monocyclic, or fused or spiro polycyclic, aromatic carbocycle (ring structure having ring atoms that are all carbon) having from 3 to 12 ring atoms per ring. Illustrative examples of aryl groups include the following moieties:

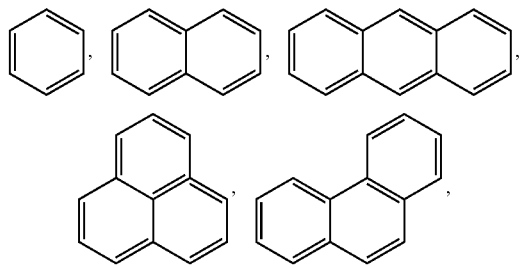

and the like.

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from 3 to 12 ring atoms per ring. Illustrative examples of aryl groups include the following moieties:

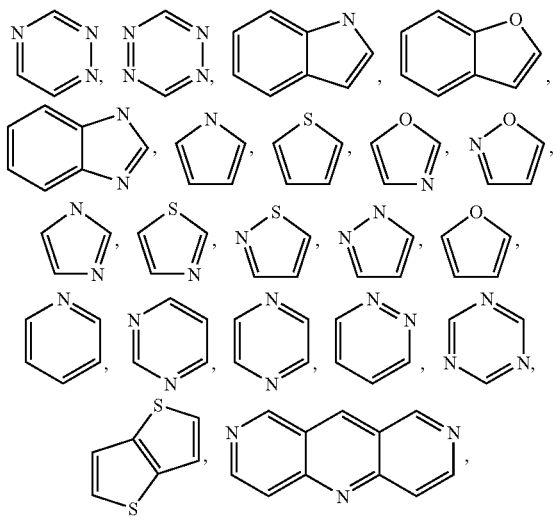

and the like.

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

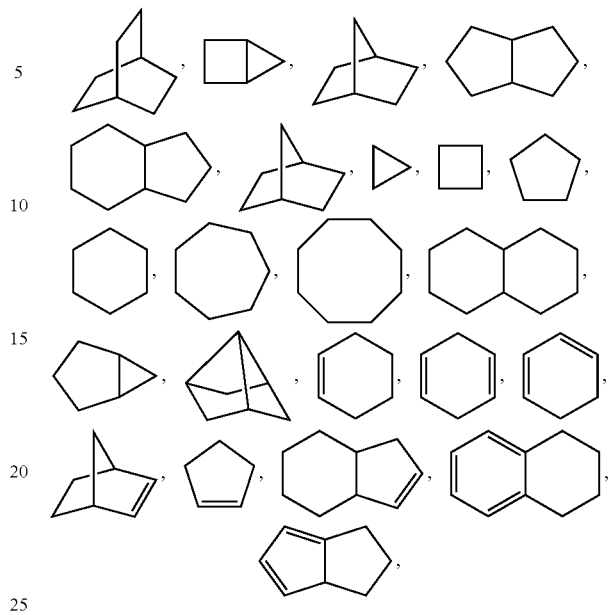

and the like.

A "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

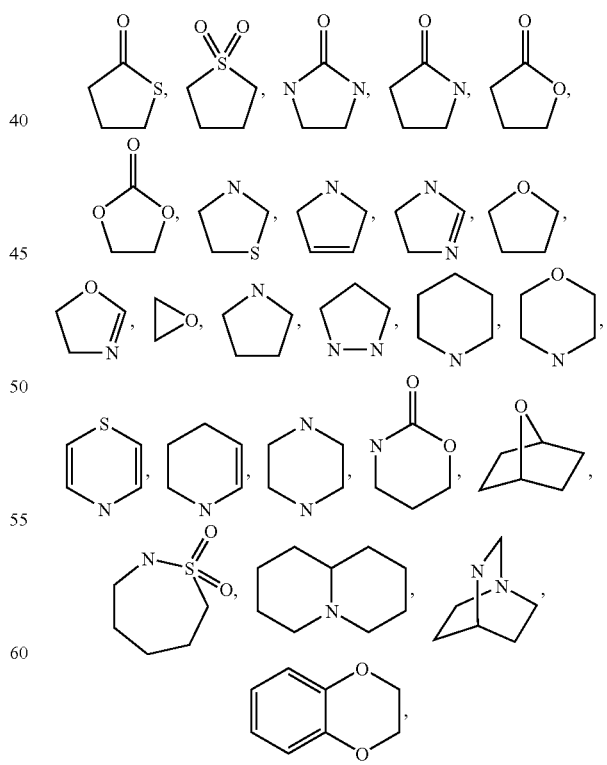

and the like.

The term "halogen(s)" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

HIV Integrase Agents

HIV Integrase agents in accordance with the invention include active tautomeric and stereoisomeric forms of the compounds of Formula I, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

It is understood that while a compound may exhibit the phenomenon of tautomerism, the formula drawings within this specification expressly depict only one of the possible tautomeric forms. It is therefore to be understood that a formula is intended to represent any tautomeric form of the depicted compound and is not to be limited merely to a specific compound form depicted by the structural formula.

It is also understood that a compound of Formula I may exist as an "E" or "Z" configurational isomer, or a mixture of E and Z isomers. It is therefore to be understood that a formula is intended to represent any configurational form of the depicted compound and is not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. In one preferred embodiment, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I is intended to cover, where applicable, solvated as well as unsolvated forms of the compounds. Thus, each formula includes compounds having the indicated structure, including the hydrated as well as the non-hydrated forms.

In addition to compounds of the Formula I, the HIV Integrase agents of the invention include pharmaceutically acceptable salts, prodrugs, and active metabolites of such compounds, and pharmaceutically acceptable salts of such metabolites. A "pharmaceutically acceptable prodrug" is a compound that may be converted under physiological conditions or by solvolysis to the specified compound or to a pharmaceutically acceptable salt of such compound. A "pharmaceutically active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011-2016 (1997); Shan et al., *J. Pharm. Sci.*, 86(7), 765-767 (1997); Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al. eds., Harwood Academic Publishers, 1991); Dear et al., *J. Chromatogr. B*, 748, 281-293 (2000); Spraul et al., *J. Pharmaceutical & Biomedical Analysis*, 10(8), 601-605 (1992); and Prox et al., *Xenobiol.*, 3(2), 103-112 (1992).

The term "pharmaceutically acceptable salts" refers to salt forms that are pharmacologically acceptable and substantially non-toxic to the subject being administered the HIV Integrase agent. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isothionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

Preferred HIV Integrase Agents

Preferred HIV Integrase agents of the invention include compounds represented by Formula I:

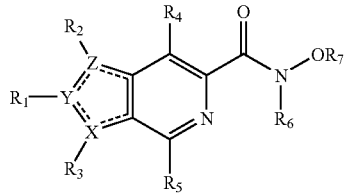

Formula I wherein:

$R_1$ is hydrogen or —C(O)OR$_c$, where R$_c$ is an unsubstituted alkyl, unsubstituted alkenyl, or unsubstituted alkynyl group;

$R_2$ is hydrogen or an alkyl, alkenyl, or heteroalkyl group, unsubstituted or substituted with one or more substituents independently selected from the group consisting of:

—O—; —NR$_d$R$_d$; —OR$_d$; halogens; and an aryl group, unsubstituted or substituted with one or more substituents independently selected from the group consisting of:

halogens; —C(R$_d$)$_3$; unsubstituted alkyl, alkyl-R$_d$, alkenyl-R$_d$, and aryl groups, where R$_d$ is one or more substituents independently selected from the group consisting of hydrogen; unsubstituted alkyl, unsubstituted alkenyl, and unsubstituted aryl groups;

$R_3$ is hydrogen or an alkyl, alkenyl, or heteroalkyl group, unsubstituted or substituted with one or more substituents independently selected from the group consisting of:

—O—; —OR$_e$; and, alkyl, aryl, cycloalkyl, and heteroaryl groups, unsubstituted or substituted with one or more substituents independently selected from the group consisting of:

halogens; —OH; and aryl or heteroaryl groups, substituted with one or more R$_e$ substituents, where R$_e$ is one or more substituents independently selected from the group consisting of halogens; hydrogen; OH; unsubstituted alkyl; and aryl unsubstituted or substituted with one or more substituents independently selected from the group consisting of halogen and alkyl;

$R_4$ is hydrogen or an alkyl group, unsubstituted or substituted with —OR$_f$, where R$_f$ is an unsubstituted alkyl group;

$R_5$ is hydrogen or an alkyl group;

$R_6$ is hydrogen or an alkyl group unsubstituted or substituted with an aryl group;

$R_4$ and $R_6$ together with the N to which $R_6$ is attached cyclize to form the following compound represented by the Formula Id:

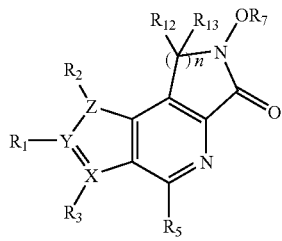

Formula Id wherein $R_{12}$ and $R_{13}$ are each independently hydrogen; and n is 1;

$R_7$ is hydrogen or an alkyl alkenyl, or aryl group, unsubstituted or substituted with an aryl group, unsubstituted or substituted with one or more halogens;

X is C or N;

Y is C;

Z is C or N; and there is a double bond between X and the 6-membered ring and Z and the 6-membered ring; or between X and Y; or between Y and Z;

or a pharmaceutically acceptable salt, pharmaceutically acceptable prodrug, or a pharmaceutically active metabolite thereof.

More preferred are HIV Integrase agents of the Formula I, where $R_1$ is hydrogen or —C(O)O-ethyl;

$R_2$ is hydrogen, methyl, ethyl, propyl, vinyl, allyl, or benzyl, unsubstituted or substituted with one or more substituents independently selected from the group consisting of:

halogens, —O—, OH, amino, and phenyl, unsubstituted or substituted with one or more substituents selected from the group consisting of:

methyl, ethyl, phenyl, benzyl, 2-phenylethyl, 3-phenylallyl, and 2-phenylvinyl;

$R_3$ is methyl, ethyl, butyl, or benzyl, unsubstituted or substituted with one or more substituents independently selected from the group consisting of:

halogens, OH, methyl, cyclohexyl, —O—, thiadiazole, thiophenyl, and phenoxy, unsubstituted or substituted with one or more substituents independently selected from the group consisting of:

halogens, phenyl, and ethoxy;

$R_4$ is hydrogen, methyl or methoxymethyl;

$R_5$ is hydrogen or methyl;

$R_6$ is hydrogen, methyl, or benzyl;

$R_7$ is hydrogen, methyl, benzyl, phenyl, allyl, or tert-butyl, unsubstituted or substituted with one or more halogens; and $R_4$ and $R_6$ together with the N to which $R_6$ attaches cyclize to form a pyrrole-2-one.

Even more preferred are HIV Integrase agents of the Formula I, where $R_1$ is hydrogen or —C(O)O-ethyl;

$R_2$ is selected from hydrogen;

hydroxymethyl;

methoxymethyl;

ethoxymethyl;

2-phenylvinyl;

3-phenylprop-1-enyl;

[(2-phenylvinyl)oxy]methyl;
dimethylaminomethyl;
benzyloxymethyl;
4-fluorobenzyl;
2-phenylvinyl;
2-phenylethyl;
3-phenylpropyl;
2-phenylethoxymethyl;
[(phenyl prop-2-enyl)oxy]methyl;
[(3-phenylallyl)oxy]methyl;
methyl;
ethyl; and
allyl;
$R_3$ is selected from
hydrogen;
2,4-difluorobenzyl;
2,3-difluorobenzyl;
4-fluorobenzyl;
3-chloro-2,6-difluorobenzyl;
3-chloro-5-fluoro-2-hydroxybenzyl;
5-chloro-thiophen-2-ylmethyl;
3-chloro-2-fluorobenzyl;
2,3-dichlorobenzyl;
5-ethoxy-[1,2,3]thiadiazol-4-ylmethyl;
3-methyl-butyl;
2-cyclohexyl-ethyl;
2,4-difluoro-phenoxymethyl;
3,5-difluoro-2-hydroxybenzyl;
2-chloro-4-fluoro-phenoxymethyl;
3-chloro-5-fluoro-2-hydroxybenzyl;
4-fluoro-phenoxymethyl;
5-fluoro-2-hydroxy-benzyl;
2,3,4-trifluoro-phenoxymethyl;
3,4,5-trifluoro-2-hydroxybenzyl;
2-chloro-phenoxymethyl; and
5-chloro-2-hydroxy-benzyl;
$R_4$ is hydrogen, methyl or methoxymethyl;
$R_5$ is hydrogen or methyl;
$R_6$ is hydrogen, methyl, or benzyl;
$R_7$ is hydrogen, methyl, benzyl, phenyl, pentafluorobenzyl, allyl, tert-butyl;
$R_4$ and $R_6$ together with the N to which $R_6$ attaches cyclize to form a pyrrol-2-one.

Most preferred are the compounds set forth in the examples below, including the following compounds:
1-(2,4-Difluorobenzyl)-N-hydroxy-1H-pyrrolo[2,3-c]pyridine-5-carboxamide;
1-(2,4-Difluorobenzyl)-N-hydroxy-N-methyl-1H-pyrrolo[2, 3-c]pyridine-5-carboxamide;
1-(4-Fluorobenzyl)-N-hydroxy-1H-pyrrolo[2,3-c]pyridine-5-carboxamide;
1-(4-Fluorobenzyl)-N-hydroxy-N-methyl-1H-pyrrolo[2,3-c]pyridine-5-carboxamide;
N-Benzyl-1-(4-fluorobenzyl)-N-hydroxy-1H-pyrrolo[2,3-c]pyridine -5-carboxamide;
1-(3-Chloro-2,6-difluorobenzyl)-N-hydroxy-1H-pyrrolo[2, 3-c]pyridine-5-carboxamide;
1-(5-Chloro-thiophen-2-ylmethyl)-N-hydroxy-1H-pyrrolo[2,3-c]pyridine-5-carboxamide;
1-(3-Chloro-2-fluorobenzyl)-N-hydroxy-1H-pyrrolo[2,3-c]pyridine-5-carboxamide;
1-(2,3-Dichlorobenzyl)-N-hydroxy-1H-pyrrolo[2,3-c]pyridine-5-carboxamide;
1-(5-Ethoxy-[1,2,3]thiadiazol-4-ylmethyl)-N-hydroxy-1H-pyrrolo[2,3-c]pyridine-5-carboxamide;
1-(2,4-Difluorobenzyl)-N-hydroxy-4-methyl-1H-pyrrolo[2, 3-c]pyridine-5-carboxamide;
1-(2,4-Difluorobenzyl)-3-ethoxymethyl-N-hydroxy-1H-pyrrolo[2, 3-c]pyridine-5-carboxamide;
1-(2,4-Difluorobenzyl)-N-hydroxy-3-hydroxymethyl-1H-pyrrolo[2,3-c]pyridine-5-carboxamide;
1-(2,4-Difluorobenzyl)-3-dimethylaminomethyl-N-hydroxy-1H-pyrrolo[2,3-c]pyridine-5-carboxamide;
3-Benzyloxymethyl-1-(2,4-difluorobenzyl )-N-hydroxy-1H-pyrrolo[2, 3-c]pyridine-5-carboxamide;
3-(2,4-Difluorobenzyl)-N-hydroxy-3H-imidazo[4,5-c]pyridine-6-carboxamide;
1-(2,4-Difluorobenzyl)-N-hydroxy-1H-imidazo[4,5-c]pyridine-6-carboxamide;
1-(2,4-Difluorobenzyl)-3-ethoxymethyl-N-hydroxy-N-methyl-1H-pyrrolo[2, 3-c]pyridine-5-carboxamide;
1-(2,4-Difluorobenzyl)-N-hydroxy-3-hydroxymethyl-N-methyl-1H-pyrrolo[2,3-c]pyridine-5-carboxamide;
1-(2,4-Difluorobenzyl)-3-dimethylaminomethyl-N-hydroxy-N-methyl-1H-pyrrolo[2,3-c]pyridine-5-carboxamide;
1-(2,4-Difluorobenzyl)-N-methoxy-1H-pyrrolo[2,3-c]pyridine-5-carboxamide;
1-(2,4-Difluorobenzyl)-3-ethoxymethyl-N-methoxy-1H-pyrrolo[2,3-c]pyridine-5-carboxamide;
1-(2,4-Difluorobenzyl)-3-hydroxymethyl-N-methoxy-1H-pyrrolo[2,3-c]pyridine-5-carboxamide;
1-(2,4-Difluorobenzyl)-3-dimethylaminomethyl-N-methoxy-1H-pyrrolo[2,3-c]pyridine-5-carboxamide;
N-Benzyloxy-1-(2,4-difluorobenzyl)-1H-pyrrolo[2,3-c]pyridine-5-carboxamide;
N-Benzyloxy-3-(4-fluorobenzyl)-3H-imidazo[4,5-c]pyridine-6-carboxamide;
3-(4-Fluorobenzyl)-N-methoxy-3H-imidazo[4,5-c]pyridine-6-carboxamide;
3-(4-Fluorobenzyl)-N-phenoxy-3H-imidazo[4,5-c]pyridine-6-carboxamide;
3-(4-Fluorobenzyl)-N-[(pentafluorobenzyl)oxy]-3H-imidazo[4,5-c]pyridine-6-carboxamide;
N-(Allyloxy)-3-(4-fluorobenzyl )-3H-imidazo[4,5-c]pyridine-6-carboxamide;
6-(2,4-Difluorobenzyl)-2-hydroxy-1,6-dihydrodipyrrolo[3,2-d:3',4'-b]pyridin-3(2H)-one;
3-(2,3-Difluorobenzyl)-N-phenoxy-3H-imidazo[4,5-c]pyridine-6-carboxamide;
3-(2,3-Difluorobenzyl)-N-methoxy-3H-imidazo[4,5-c]pyridine-6-carboxamide;
N-Allyloxy-3-(2,3-difluorobenzyl)-3H-imidazo[4,5-c]pyridine-6-carboxamide;
1-(4-Fluorobenzyl)-N-phenoxy-1H-imidazo[4,5-c]pyridine-6-carboxamide;
N-tert-Butoxy-3-(2,3-difluorobenzyl )-3H-imidazo[4,5-c]pyridine-6-carboxamide;
N-Methoxy-3-(3-methyl-butyl)-3H-imidazo[4,5-c]pyridine-6-carboxamide;
3-(3-Methyl-butyl)-N-phenoxy-3H-imidazo[4,5-c]pyridine-6-carboxamide;
3-(2-Cyclohexyl-ethyl)-N-phenoxy-3H-imidazo[4,5-c]pyridine-6-carboxamide;
3-(2-Cyclohexyl-ethyl)-N-methoxy-3H-imidazo[4,5-c]pyridine-6-carboxamide;
N-Allyloxy-3-(2-cyclohexyl-ethyl )-3H-imidazo[4,5-c]pyridine-6-carboxamide;
1-(2,4-Difluorobenzyl)-N-hydroxy-4-methoxymethyl-1H-pyrrolo[2, 3-c]pyridine-5-carboxamide;
1-(2,4-Difluorobenzyl)-N-hydroxy-3-(2-phenylvinyl)-1H-pyrrolo[2,3-c]pyridine-5-carboxamide;
1-(2,4-Difluorobenzyl)-N-hydroxy-3-(3-phenylprop-1-enyl)-1H-pyrrolo[2,3-c]pyridine-5-carboxamide;

1-(2,4-Difluorobenzyl)-N-hydroxy-3-(2-phenylethyl)-1H-pyrrolo[2,3-c]pyridine-5-carboxamide;
1-(2,4-Difluorobenzyl)-N-hydroxy-3-(3-phenylpropyl)-1H-pyrrolo[2,3-c]pyridine-5-carboxamide; 1-(2,4-Difluorobenzyl)-N-hydroxy-3-{[(2-phenylethyl)oxy]methyl}-1H-pyrrolo[2,3-c]pyridine-5-carboxamide;
1-(2,4-Difluorobenzyl)-N-hydroxy-3-{[(3-phenylallyl)oxy]methyl}-1H-pyrrolo[2,3-c]pyridine-5-carboxamide;
1-(2,4-Difluorobenzyl)-N-hydroxy-3-methyl-1H-pyrrolo[2,3-c]pyridine-5-carboxamide;
1-(2,4-Difluorobenzyl)-3-ethyl-N-hydroxy-1H-pyrrolo[2,3-c]pyridine-5-carboxamide;
3-Allyl-1-(2,4-difluorobenzyl)-N-hydroxy-1H-pyrrolo[2,3-c]pyridine-5-carboxamide;
1-(2,4-Difluorobenzyl)-N-hydroxy-7-methyl-1H-pyrrolo[2,3-c]pyridine-5-carboxamide;
Ethyl 1-(2,4-Difluorobenzyl )-5-hydroxycarbamoyl-1H-pyrrolo[2, 3-c]pyridine-2-carboxylate;
3-(2,4-Difluoro-phenoxymethyl)-1-ethyl-N-hydroxy-1H-pyrrolo[3,2-c]pyridine-6-carboxamide;
3-(3,5-Difluoro-2-hydroxybenzyl)-1-ethyl-N-hydroxy-1H-pyrrolo[3,2-c]pyridine-6-carboxamide;
3-(2-Chloro-4-fluoro-phenoxymethyl)-1-ethyl-N-hydroxy-1H-pyrrolo[3,2-c]pyridine-6-carboxamide;
3-(3-Chloro-5-fluoro-2-hydroxybenzyl)-1-ethyl-N-hydroxy-1H-pyrrolo[3,2-c]pyridine-6-carboxamide;
1-Ethyl-3-(4-fluoro-phenoxymethyl)-N-hydroxy-1H-pyrrolo[3,2-c]pyridine-6-carboxamide;
1-Ethyl-3-(5-fluoro-2-hydroxybenzyl)-N-hydroxy-1H-pyrrolo[3,2-c]pyridine-6-carboxamide;
1-Ethyl-N-hydroxy-3-(2,3,4-trifluoro-2-phenoxymethyl)-1H-pyrrolo[3,2-c]pyridine-6-carboxamide;
1-Ethyl-N-hydroxy-3-(3,4,5-trifluoro-2-hydroxybenzyl)-1H-pyrrolo[3,2-c]pyridine-6-carboxamide;
3-(2-Chloro-phenoxymethyl )-1-ethyl-N-hydroxy-1H-pyrrolo[3,2-c]pyridine-6-carboxamide;
3-(5-Chloro-2-hydroxy-benzyl)-1-ethyl-N-hydroxy-1H-pyrrolo[3,2-c]pyridine-6-carboxamide and pharmaceutically acceptable salts thereof.

Additionally, compounds that modulate or inhibit HIV Integrase enzyme activity are desirable and are a preferred embodiment of the present invention. The activity of a HIV Integrase agent as an HIV Integrase inhibitor may be measured by any of the methods available to those skilled in the art, including in vivo and in vitro assays.

Pharmacology and Utility

Several different assay formats are available to measure integrase-mediated integration of viral DNA into target (or host) DNA and thus, identify compounds that modulate (e.g., inhibit) integrase activity. In general, for example, ligand-binding assays may be used to determine interaction with an enzyme of interest. When binding is of interest, a labeled enzyme may be used, wherein the label is a fluorescer, radioisotope, or the like, which registers a quantifiable change upon binding to the enzyme. Alternatively, the skilled artisan may employ an antibody for binding to the enzyme, wherein the antibody is labeled allowing for amplification of the signal. Thus, binding may be determined through direct measurement of ligand binding to an enzyme. In addition, binding may be determined by competitive displacement of a ligand bound to an enzyme, wherein the ligand is labeled with a detectable label. When inhibitory activity is of interest, an intact organism or cell may be studied, and the change in an organismic or cellular function in response to the binding of the inhibitory compound may be measured. Alternatively, cellular response can be determined microscopically by monitoring viral induced syncytium-formation (HIV-1 syncytium-formation assays), for example. Thus, there are various in vitro and in vivo assays useful for measuring HIV integrase inhibitory activity. See, e.g., Lewin, S. R. et al., Journal of Virology 73(7): 6099-6103 (July 1999); Hansen, M.S. et al., Nature Biotechnology 17(6): 578-582 (June 1999); and Butler, S. L. et al., Nature Medicine 7(5): 631-634 (May 2001).

Exemplary specific assay formats used to measure integrase-mediated integration include, but are not limited to, ELISA, DELFIA® (PerkinElmer Life Sciences Inc. (Boston, Mass.)) and ORIGEN® (IGEN International, Inc. (Gaithersburg, Md.)) technologies. In addition, gel-based integration (detecting integration by measuring product formation with SDS-PAGE) and scintillation proximity assay (SPA) disintegration assays that use a single unit of double stranded-DNA (ds-DNA) may be used to monitor integrase activity.

In one embodiment of the invention, the preferred assay is an integrase strand-transfer SPA (stINTSPA) which uses SPA to specifically measure the strand-transfer mechanism of integrase in a homogenous assay scalable for miniaturization to allow high-throughput screening. The assay focuses on strand transfer and not on DNA binding and/or 3' processing. This sensitive and reproducible assay is capable of distinguishing non-specific interactions from true enzymatic function by forming 3' processed viral DNA/integrase complexes before the addition of target DNA. Such a formation creates a bias toward compound modulators (e.g., inhibitors) of strand-transfer and not toward compounds that inhibit integrase 3' processing or prevent the association of integrase with viral DNA. This bias renders the assay more specific than known assays. In addition, the homogenous nature of the assay reduces the number of steps required to run the assay since the wash steps of a heterogenous assay are not required.

The integrase strand-transfer SPA format consists of 2 DNA components that model viral DNA and target DNA. The model viral DNA (also known as donor DNA) is biotinylated ds-DNA preprocessed at the 3' end to provide a CA nucleotide base overhang at the 5' end of the duplex. The target DNA (also known as host DNA) is a random nucleotide sequence of ds-DNA generally containing [$^3$H]-thymidine nucleotides on both strands, preferably, at the 3' ends, to enable detection of the integrase strand-transfer reaction that occurs on both strands of target ds-DNA.

Integrase (created recombinantly or synthetically and preferably, purified) is pre-complexed to the viral DNA bound to a surface, such as for example, streptavidin-coated SPA beads. Generally, the integrase is pre-complexed in a batch process by combining and incubating diluted viral DNA with integrase and then removing unbound integrase. The preferred molar ratio of viral DNA:integrase is about 1: about 5. The integrase/viral DNA incubation is optional, however, the incubation does provide for an increased specificity index with an integrase/viral DNA incubation time of about 15 to about 30 minutes at room temperature or at about 37° C. The preferred incubation is at about room temperature for about 15 minutes.

The reaction is initiated by adding target DNA, in the absence or presence of a potential integrase modulator compound, to the integrase/viral DNA beads (for example) and allowed to run for about 20 to about 50 minutes (depending on the type of assay container employed), at about room temperature or about 37° C., preferably, at about 37° C. The assay is terminated by adding stop buffer to the integrase reaction mixture. Components of the stop buffer, added sequentially or at one time, function to terminate enzymatic activity, dissociate integrase/DNA complexes, separate non-integrated DNA strands (denaturation agent), and, optionally, float the SPA beads to the surface of the reaction mixture to be closer in range to the detectors of, for example, a plate-based scintillation counter, to measure the level of integrated viral DNA which is quantified as light emitted (radiolabeled signal) from the SPA beads. The inclusion of an additional component in the stop buffer, such as for example CsCl or functionally equivalent compound, is optionally, and preferably, used with a plate-based scintillation counter, for example, with detectors positioned above the assay wells, such as for example a TopCount® counter (PerkinElmer Life Sciences Inc. (Boston, Mass.)). CsCl would not be employed when PMT readings are taken from the bottom of the plate, such as for example when a MicroBeta® counter (PerkinElmer Life Sciences Inc. (Boston, Mass.)) is used.

The specificity of the reaction can be determined from the ratio of the signal generated from the target DNA reaction with the viral DNA/integrase compared to the signal generated from the di-deoxy viral DNA/integrase. High concentrations (e.g., $\geq 50$ nM) of target DNA may increase the d/dd DNA ratio along with an increased concentration of integrase in the integrase/viral DNA sample.

The results can be used to evaluate the integrase modulatory, such as for example inhibitory, activity of test compounds. For example, the skilled artisan may employ a high-throughput screening method to test combinatorial compound libraries or synthetic compounds. The percent inhibition of the compound may be calculated using an equation such as for example (1-((CPM sample–CPM min)/(CPM max–CPM min)))*100. The min value is the assay signal in the presence of a known modulator, such as for example an inhibitor, at a concentration about 100-fold higher than the $IC_{50}$ for that compound. The min signal approximates the true background for the assay. The max value is the assay signal obtained for the integrase-mediated activity in the absence of compound. In addition, the $IC_{50}$ values of synthetic and purified combinatorial compounds may be determined whereby compounds are prepared at about 10 or 100-fold higher concentrations than desired for testing in assays, followed by dilution of the compounds to generate an 8-point titration curve with ½-log dilution intervals, for example. The compound sample is then transferred to an assay well, for example. Further dilutions, such as for example, a 10-fold dilution, are optional. The percentage inhibition for an inhibitory compound, for example, may then be determined as above with values applied to a nonlinear regression, sigmoidal dose response equation (variable slope) using GraphPad Prism curve fitting software (GraphPad Software, Inc., San Diego, Calif.) or functionally equivalent software.

The stINTSPA assay conditions are preferably optimized for ratios of integrase, viral DNA and target DNA to generate a large and specific assay signal. A specific assay signal is defined as a signal distinguishing true strand-transfer catalytic events from complex formation of integrase and DNA that does not yield product. In other integrase assays, a large non-specific component (background) often contributes to the total assay signal unless the buffer conditions are rigorously optimized and counter-tested using a modified viral DNA oligonucleotide. The non-specific background is due to formation of integrase/viral DNA/target DNA complexes that are highly stable independent of a productive strand-transfer mechanism.

The preferred stINTSPA distinguishes complex formation from productive strand-transfer reactions by using a modified viral DNA oligonucleotide containing a di-deoxy nucleoside at the 3' end as a control. This modified control DNA can be incorporated into integrase/viral DNA/target DNA complexes, but cannot serve as a substrate for strand-transfer. Thus, a distinct window between productive and non-productive strand-transfer reactions can be observed. Further, reactions with di-deoxy viral DNA beads give an assay signal closely matched to the true background of the assay using the preferred optimization conditions of the assay. The true background of the assay is defined as a reaction with all assay components (viral DNA and [$^3$H]-target DNA) in the absence of integrase.

Assay buffers used in the integrase assay generally contain at least one reducing agent, such as for example 2-mercaptoethanol or DTT, wherein DTT as a fresh powder is preferred; at least one divalent cation, such as for example $Mg^{++}$, $Mn^{++}$, or $Zn^{++}$, preferably, $Mg^{++}$; at least one emulsifier/dispersing agent, such as for example octoxynol (also known as IGEPAL-CA or NP-40) or CHAPS; NaCl or functionally equivalent compound; DMSO or functionally equivalent compound; and at least one buffer, such as for example MOPS. Key buffer characteristics are the absence of PEG; inclusion of a high concentration of a detergent, such as for example about 1 to about 5 mM CHAPS and/or about 0.02 to about 0.15% IGEPAL-CA or functionally equivalent compound(s) at least capable of reducing non-specific sticking to the SPA beads and assay wells and, possibly, enhancing the specificity index; inclusion of a high concentration of DMSO (about 1 to about 12%); and inclusion of modest levels of NaCl ($\leq 50$ mM) and $MgCl_2$ (about 3 to about 10 mM) or functionally equivalent compounds capable of reducing the dd-DNA background. The assay buffers may optionally contain a preservative, such as for example $NaN_3$, to reduce fungal and bacterial contaminants during storage.

The stop buffer preferably contains EDTA or functionally equivalent compound capable of terminating enzymatic activity, a denaturation agent comprising, for example, NaOH or guanidine hydrochloride, and, optionally, CsCl or functionally equivalent compound capable of assisting in floating the SPA beads to the top of the assay container for scintillation detection at the top of the reservoir and, possibly, minimizing compound interference. An example of an integrase strand-transfer SPA is set forth in Example 64.

Alternatively, the level of activity of the modulatory compounds may be determined in an antiviral assay, such as for example an assay that quantitatively measures the production of viral antigens (e.g., HIV-1 p24) or the activities of viral enzymes (e.g., HIV-1 reverse transcriptase) as indicators of virus replication, or that measures viral replication by monitoring the expression of an exogenous reporter gene introduced into the viral genome (HIV-1 reporter virus assays) (Chen, B. K. et al., *J. Virol.* 68(2): 654-660 (1994); Terwilliger, E. F. et al., *PNAS* 86:3857-3861 (1989)). A preferred method of measuring antiviral activity of a potential modulator compound employs an HIV-1 cell protection assay, wherein virus replication is measured indirectly by monitoring viral induced host-cell cytopathic effects using, for example, dye reduction methods as set forth in Example 65.

Preferred HIV integrase agents of the invention include those having an $EC_{50}$ value of at least 10-5 M (or at least 10 μM) when measured with an HIV cell protection assay. Especially preferred anti-integrase agents are those having an $EC_{50}$ value of at least 1 μM when measured with an HIV cell protection assay. Even more preferred are those agents having an $EC_{50}$ value of at least 0.1 μM when measured with an HIV cell protection assay.

Administration and Pharmaceutical Compositions

The HIV Integrase agents of the invention may be formulated into pharmaceutical compositions as described below in any pharmaceutical form recognizable to the skilled artisan as being suitable. Pharmaceutical compositions of the invention comprise a therapeutically effective amount of at least one compound of Formula I and an inert, pharmaceutically acceptable carrier or diluent.

A "therapeutically effective amount" is intended to mean that amount of a compound that, when administered to a mammal in need of such treatment, is sufficient to effect treatment, as defined herein. Thus, e.g., a therapeutically effective amount of a compound of the Formula I, salt, active metabolite or prodrug thereof, is a quantity sufficient to modulate or inhibit the activity of HIV Integrase such that a disease condition that is mediated by activity is reduced or alleviated.

It will be appreciated that the actual dosages of the agents of this invention will vary according to the particular agent being used, the particular composition formulated, the mode of administration, and the particular site, host, and disease being treated. Optimal dosages for a given set of conditions may be ascertained by those skilled in the art using conventional dosage-determination tests in view of the experimental data for a given compound. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

To treat or prevent diseases or conditions mediated by HIV, a pharmaceutical composition of the invention is administered in a suitable formulation prepared by combining a therapeutically effective amount (i.e., an HIV Integrase modulating, regulating, or inhibiting amount effective to achieve therapeutic efficacy) of at least one HIV Integrase agent of the invention (as an active ingredient) with one or more pharmaceutically suitable carriers, which may be selected, for example, from diluents, excipients and auxiliaries that facilitate processing of the active compounds into the final pharmaceutical preparations.

Additionally, the present invention is directed to a pharmaceutical composition comprising a therapeutically effective amount of at least one HIV Integrase agent in combination with one or more additional active ingredients, such as, for example, a second HIV Integrase agent, an HIV/AIDS antiviral agent, an anti-infective agent, and/or an immunomodulator.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added.

Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of an inventive agent may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration chosen. For injection, the agents of the invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly-soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

Methods of Use

The present invention is further directed to methods of modulating or inhibiting an enzyme activity of HIV Integrase, for example in mammals, by contacting the HIV Integrase enzyme with an effective amount of one or more HIV Integrase agent(s) or a composition comprising a HIV Integrase agent as described above. Additionally, the present invention is directed to methods of treating HIV mediated diseases or conditions by administering a therapeutically effective amount of one or more HIV Integrase agent(s) or a composition comprising a HIV Integrase agent to a mammal in need of such treatment.

The terms "treat", "treating", and "treatment" refer to any treatment of a HIV Integrase mediated disease or condition in a mammal, particularly a human, and include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition.

Diseases or conditions mediated by HIV include, but are not limited to, AIDS and ARC.

Synthesis of HIV Integrase Agents

The inventive agents may be prepared using the reaction routes and synthesis schemes as described below, employing the techniques available in the art using starting materials that are readily available. The preparation of preferred compounds of the present invention is described in detail in the following examples, but the artisan will recognize that the chemical reactions described may be readily adapted to prepare a number of other HIV Integrase agents of the invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

Reagents useful for synthesizing compounds may be obtained or prepared according to techniques known in the art. For example, the preparation of free amines from common salt forms and stock reagent solutions can be useful for small-scale reactions. See also Abdel-Magid et al., "Reductive Amination of Aldehydes and Ketones with Sodium Triacetoxyborohydride," *J. Org. Chem.* 61: 3849 (1996).

Methanolic solutions of the free bases can be prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1 M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37 M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1-2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5 M solution of sodium borohydride in ethanol may be prepared as follows. Sodium borohydride (520 mg, 13.8 mmol) is stirred in pure (non-denatured) anhydrous ethanol (25 mL) for ~2-3 minutes. The suspension is filtered through a medium fritted glass funnel to remove a small amount of undissolved solid (typically about 5% of the total mass of borohydride, or 25 mg). The filtrate should appear as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8 M. However, sometimes a small percentage of the solid remains undissolved regardless of the concentration being prepared, even after stirring for ≧5 minutes.

The following abbreviations employed throughout the application have the following meaning unless otherwise indicated:THF: tetrahydrofuran; DMF: N,N-dimethylformamide;TLC: thin-layer-chromatography; HATU: O-(azabenzotriazole-1-yl)-1,1,3,3-tetramethyluronium hexafluorophosphate; EDC: N-(3-dimethylaminopropyl)-N'-ethylcarbodiimide. Additional abbreviations employed throughout the application are either known to those skilled in the art or are explained in the Examples below.

EXAMPLES

The present invention will be further illustrated in the following, non-limiting examples.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeale bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60° F. 254 plates (Analtech (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat. Work-ups were typically done by doubling the reaction volume with the reaction solvent or extraction solvent and then washing with the indicated aqueous solutions using 25% by volume of the extraction volume (unless otherwise indicated). Product solutions were dried over anhydrous $Na_2SO_4$ prior to filtration, and evaporation of the solvents was under reduced pressure on a rotary evaporator and noted as solvents removed in vacuo. Flash column chromatography [Still et al., *A. J. Org. Chem.* 43:2923 (1978)] was conducted using Baker-grade flash silica gel (47-61 mm) and a silica gel: crude material ratio of about 20:1 to 50:1, unless otherwise stated. Hydrogenolysis was done at the pressure indicated or at ambient pressure.

$^1$H-NMR spectra were recorded on a Bruker instrument operating at 300 MHz, 500 MHz, and 13CNMR spectra was recorded operating at 75 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as $CDCl_3$ solutions, and when reported are in wave numbers ($cm^{-1}$).

The mass spectra were obtained using LC/MS or APCI. All melting points are uncorrected.

All final products had greater than 85% purity (by HPLC at wavelengths of 220 nm and 254 nm).

General Procedures

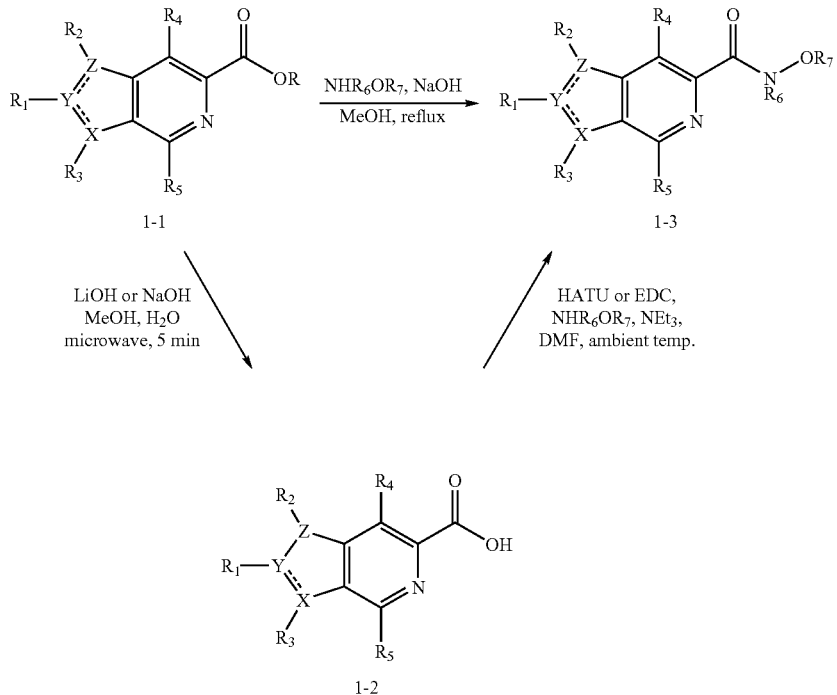

Scheme 1

The compounds of the present invention can be prepared directly from compound 1-1 (preferably a methyl or ethyl ester) and a substituted or unsubstituted hydroxyl amine in the presence of a base, such as, for example, sodium hydroxide or sodium alkoxide in methanol or ethanol (Hauser, C. R. et al., *Org. Synth. Coll. Vol.* 2, p. 67, John Wiley, New York (1943)). Alternatively, the compound 1-1 can be saponified to the free acid 1-2 using lithium hydroxide or sodium hydroxide in methanol/water mixtures and heating the mixture to 100° C. in a SmithCreator® microwave for 1 to 5 min. Compound 1-2 can be coupled with a substituted or unsubstituted hydroxyl amine using a coupling reagent. Typical coupling reagents and conditions can be used, such as, for example, O-(azabenzotriazole-1-yl)-1,1,3,3-tetramethyl uronium hexafluorophosphate (HATU), N-(3-dimethylaminopropyl)-N'-ethylcarbodiimide (EDC) in DMF at ambient temperature, or many others that are familiar to those skilled in the art. Other suitable methods are described, for example, in Jerry March, Advanced Organic Chemistry, 5th edition, John Whiley & Sons, p. 508-511 (2001). The use of the preferred conditions described in this Scheme would allow for parallel preparation or combinatorial libraries of such hydroxamates 1-3.

Preparation of Intermediates and Starting Materials

Scheme 2

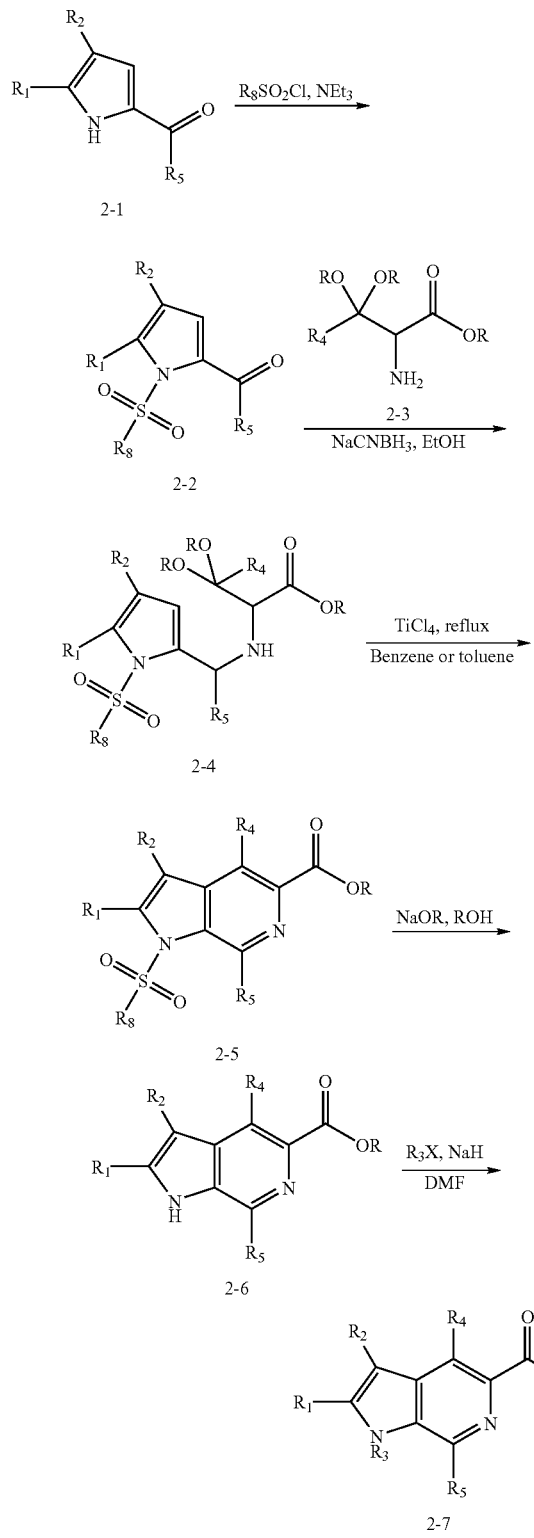

(Compound 2-7) can be prepared from an arylsulfonyl or alkylsulfonyl protected pyrrole compound 2-2 formed from pyrrole compound 2-1 and an arylsulfonylchloride or an alkylsulfonylchloride in the presence of a base, such as, for example, triethylamine, using methods decribed, for example, in T. W. Greene, Protective Groups in Organic Chemistry, $3^{rd}$ edition, John Wiley & Sons, pp. 615-617 (1999). Reductive amination with a suitable substituted glycine ester compound 2-3 and a reducing agent, such as, for example, $NaCNBH_3$ or $NaBH(OAc)_3$ (Abdel-Magid, A. F. et al., Tetrahedron Lett., 31, 5595-5598 (1990)) can provide the amine compound 2-4. Additional methods for reductive amination exist and are reviewed in C. F. Lane, Synthesis, p. 135 (1975). Titanium tetrachloride mediated cyclization (Dekhane, M. et al., Tetrahedron, 49, pp. 8139-8146 (1993); and Singh, S. K., Heterocycles, 44, pp. 379-391 (1997)) in a solvent, such as, for example, benzene or toluene, at the boiling temperature of the solvent can provide the arylsulfonyl or alkylsulfonyl protected precursor compound 2-5, which can be converted to the desired unprotected indole compound 2-6 using sodium alkoxide in alcohol (M. Dekhane, P. Potier, R. H. Dodd, Tetrahedron, 49, 8139-8146 (1993)). Alkylation of compound 2-6 with an alkylhalide in a polar solvent such as DMF or DMSO using sodium hydride as base (Eberle, M. K., J. Org. Chem. 41, pp. 633-636 (1976); Sundberg, R. J. et al., J. Org. Chem. 38, pp. 3324-3330 (1973)) can provide the desired precursor compound 2-7.

Scheme 3

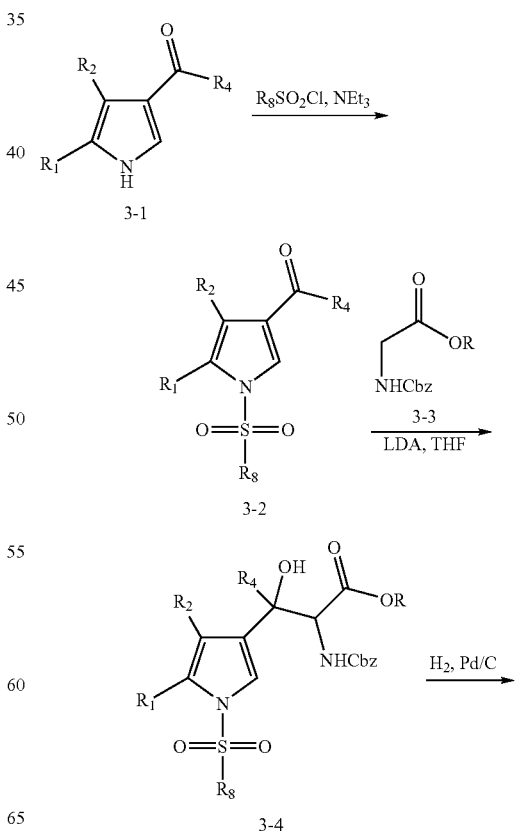

The precursors 1-1 (where X=N, Y=C, Z=C, $R_5$=H, and preferably where R=an alkyl group and $R_8$=an alkyl or aryl group unsubstituted or substituted with an alkyl group)

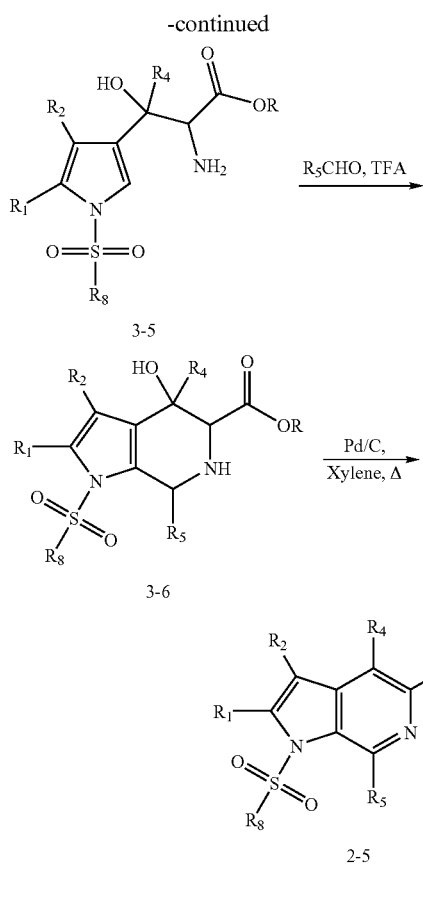

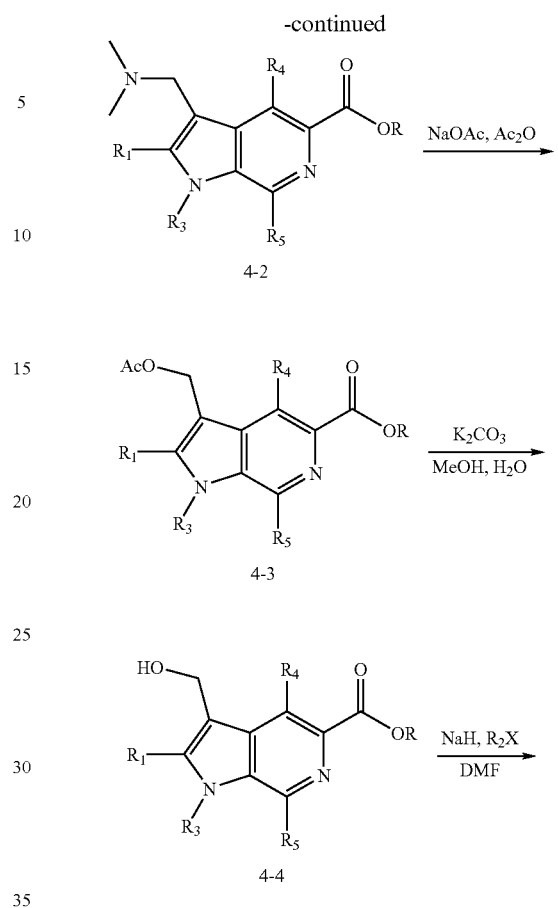

Scheme 3 depicts an alternative method for obtaining intermediate compound 2-5 adapted from the literature (preferably where R=an alkyl group and $R_8$=an alkyl or aryl group unsubstituted or substituted with an alkyl group) (Rousseau, J. F. et al., *J. Org. Chem.*, 63, pp. 2731-2737 (1998) and citations therein) starting from the substituted pyrrole compound 3-1. The pyrrole nitrogen can be protected as a sulfonamide using the same methods described in scheme 2. Addition of the anion of a N-Cbz glycine ester can provide the intermediate compound 3-4. Removal of the Cbz protecting group can be achieved using palladium catalyzed hydrogenation or other methods, such as those decribed in T. W. Greene, Protective Groups in Organic Chemistry, 3$^{rd}$ edition, John Wiley & Sons, pp. 531-537 (1999). Pictet-Spengler condensation followed by palladium catalyzed dehydrogenation in xylene can afford the intermediate compound 2-5.

Scheme 4

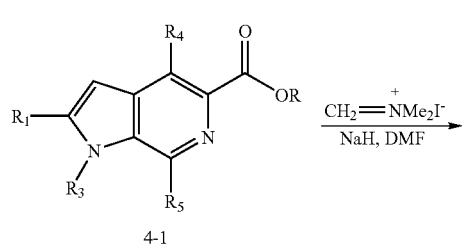

Scheme 4 (preferably where R=an alkyl group) depicts a route for synthesizing 3-5 substituted pyrrolo[2,3-c]pyridine compounds 4-5 from the unsubstituted precursor compound 4-1 (preferably where R=an alkyl group). Reaction of compound 4-1 with Eschenmoser' salt (Kozikowski, A. P. et al., *Heterocycles*, 14, pp. 55-58 (1980)) can give the dimethylaminomethyl derivative compound 4-2. Alternatively, this step can be performed using classic Mannich reaction conditions (review: Brewster, J. H. et al., *Org. Reactions*, 7, p. 99 (1953)). Upon treatment of compound 4-2 with sodium acetate and acetic anhydride in acetonitrile (Cocker, J. N. et al., *J. Org. Chem.*, 28, pp. 589-590 (1963)) the corresponding acetate compound 4-3 can be obtained which on hydrolysis with a base, such as, for example, potassium carbonate in methanol, can provide the precursor compound 4-4. Alkylation of the alcohol compound 4-4 can be achieved using, for example, an alkylhalide in a presence of a base, such as, sodium hydride in DMF as solvent.

Scheme 5

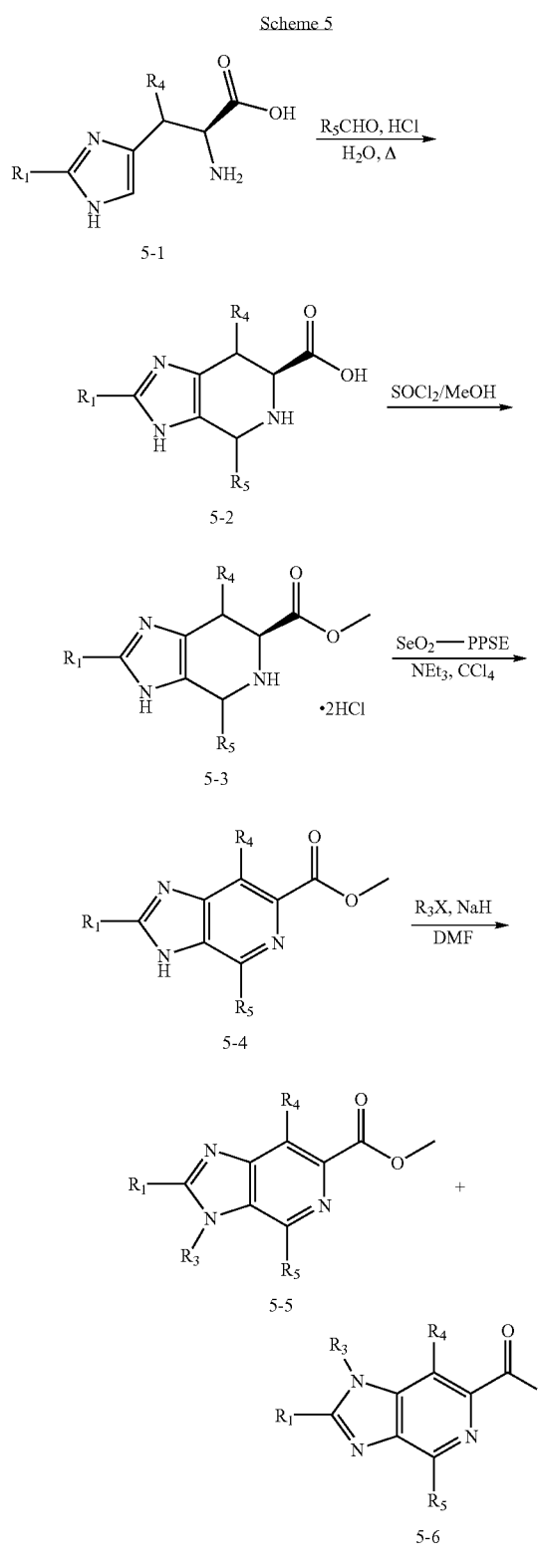

Chem. 20, pp. 721-723 (1977); Trout, G., *J. Med. Chem.*, 15, pp. 1259-1261 (1972)). Pictet-Spengler reaction of compound 5-1 (Guzman, F. et al., *J. Med. Chem.*, 27, pp. 564-570 (1984); Cain, M. et al., *Heterocycles*, 19, pp. 1003-1007 (1982)) can give the 1,2,3,4-tetrahydro-imidazo[4,5-c]pyridine-3-carboxylate compound 5-2, which can be converted to the methyl ester via the corresponding acyl chloride or similar methods of ester formation known to those skilled in the art. Dehydration to the unsaturated intermediate compound 5-3 can be achieved with selenium dioxide (Lee, J. G. et al, *Tetrahedron Lett,* 33, pp. 6363-6366 (1992)), or a catalyst such as palladium, platinum in a solvent, such as, for example, xylene, at the boiling temperature of the solvent (Soerens, D. et al., *J. Org. Chem.*, 44, pp. 535-545 (1979)). Alkylation of compound 5-4 with an alkylhalide in the presence of a base, such as, sodium hydride, similar to the methods described in scheme 2, can provide the desired precursors as a mixture of regioisomer compounds 5-5 and 5-6 that can be separated by column chromatography or other methods known to those skilled in the art.

Scheme 6

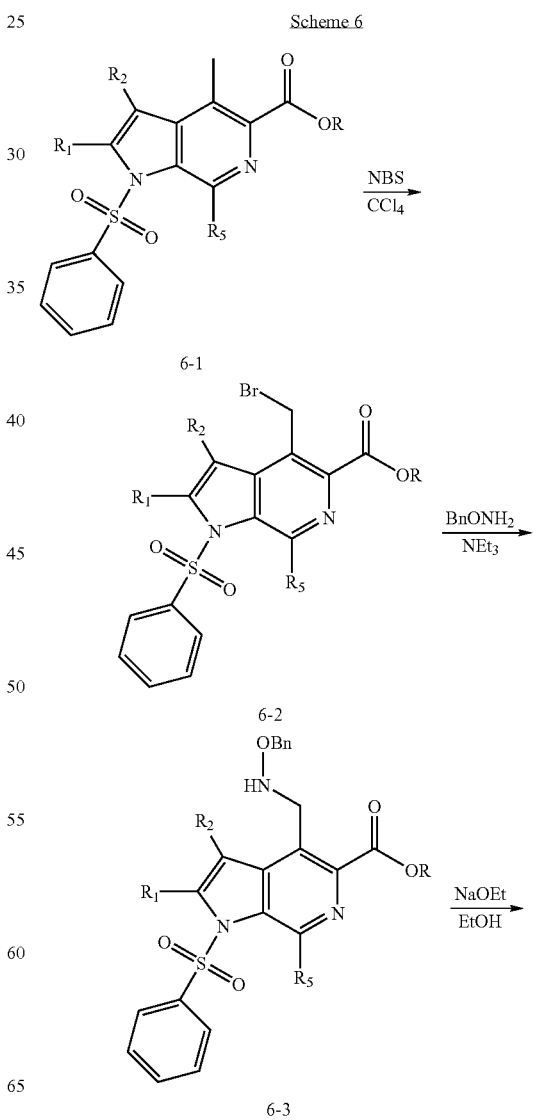

Scheme 5 depicts a method for obtaining imidazo[4,5-c]pyridine precursor compounds 1-1 where X=N, Y=C, Z=N (compounds 5-5 and 5-6). The histidine precursor compound 5-1 is commercially available or can be prepared according published methods (Kelley, J. L. et al., *J. Med.*

-continued

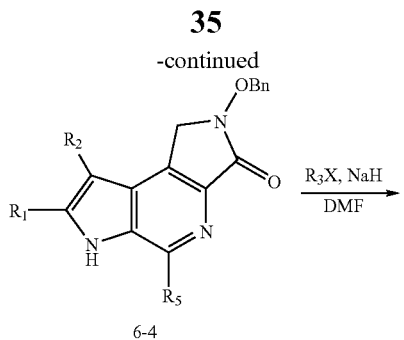
6-4

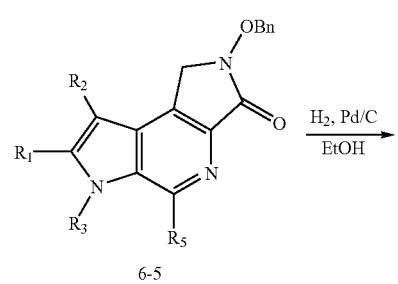
6-5

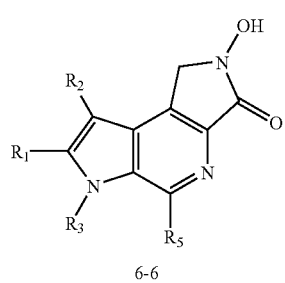
6-6

Scheme 6 depicts a method for formation of N-hydroxy lactame compounds 6-5 and 6-6 (where $R_1$=H or $CO_2Et$; $R_2$=H; $R_5$=H). Radical bromination of a methyl substituted indole 6-1 can be achieved by various reagents (March, Jerry, Advanced Organic Chemistry, 5th edition, John Whiley & Sons, pp. 911-914 (2001)), the most common being N-bromosuccinimide (NBS). It will be apparent to those skilled in the art that successful execution of this reaction can depend highly on the substitution pattern of the precursor 6-1. Reaction of an alkylhalide compound 6-2 (Doisy, X. et al., Bioorg. Med. Chem., 7, pp.921-932 (1999)) with benzyl hydroxylamine in a presence of a base, such as, triethylamine, can provide compound 6-3. Treatment with sodium ethoxide in ethanol can result in lactame formation and cleavage of the phenylsulfonyl protecting group. Alkylation of compound 6-4 with an alkylhalide in the presence of a base, such as, sodium hydride in DMF, similar to the methods described in scheme 2, can provide N-benzyloxy lactame compound 6-5. The benzyl protecting group can be removed using various methods known in the art (See, e.g, Greene, T. W., Protective Groups in Organic Chemistry, $3^{rd}$ edition, John Wiley & Sons, pp. 76-86 (1999)), such as, for example, palladium catalysed hydrogenation. As is obvious to those skilled in the art, different protecting groups, such as, for example, tert-butyl, 4-methoxybenzyl, tetrahydropyranyl, methoxymethyl, tert-butyl-dimethylsilyl, instead of the benzyl group, might be used to form the final product, compound 6-6.

Scheme 7

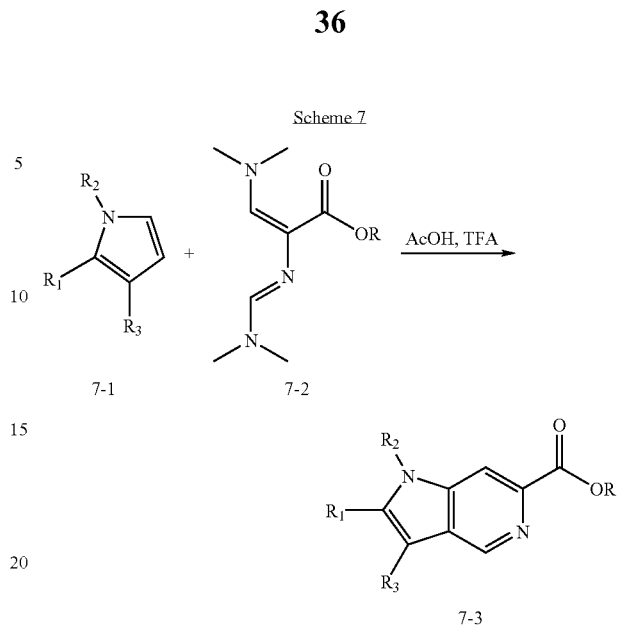

Scheme 7 sets forth a method for producing pyrrolo[3,2-c]pyridine derivatives 1-1 where X=C, Y=C, Z=N, and preferably R=an alkyl group (compound 7-3) via a substituted pyrrole compound 7-1 and 2-azabutadiene compound 7-3 (Kantlehner, W. et al., Liebigs Ann. Chem., pp. 344-357 (1980)) under proton catalysis, following the procedures described in Biere, H. et al., Liebigs Ann. Chem., pp. 491-494 (1987).

Scheme 8

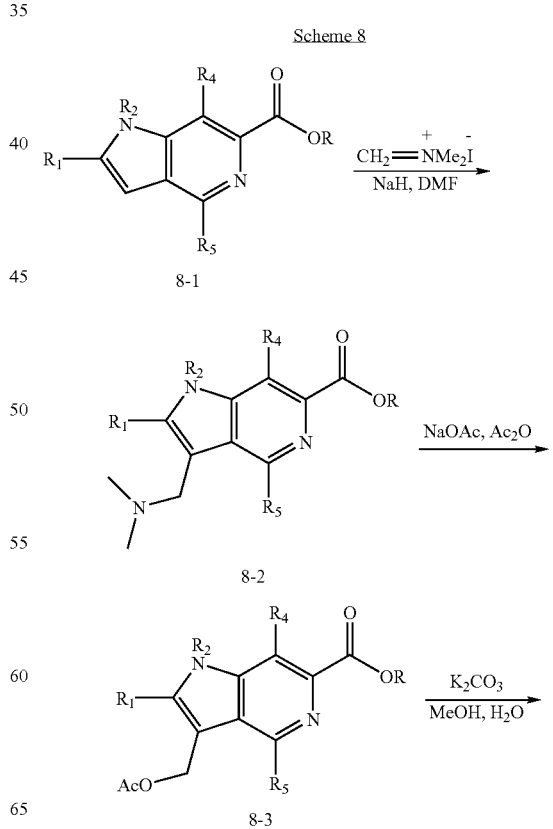

-continued

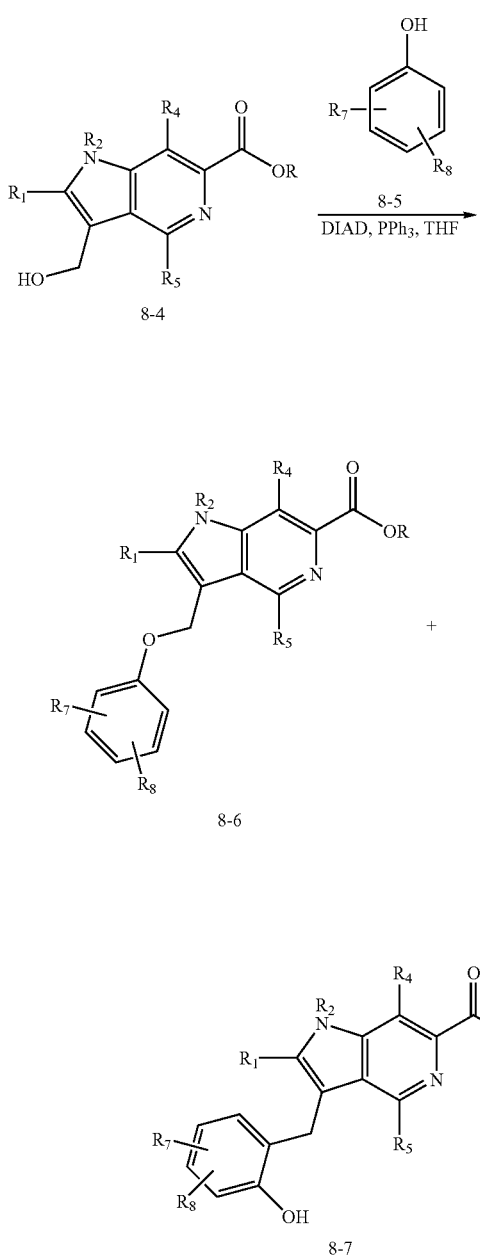

carbonate in methanol can provide the precursor compound 8-4. Treatment of the alcohol with a phenol compound 8-5 (preferably where $R_7$, and $R_8$=a halogen, nitro, $CO_2R$, CN, $CF_3$, or COR group) under standard Mitsunobu conditions (review: Hughes, D., *Org. Prep. Proced. Int.,* 28, pp.127-164 (1996)) using triphenylphosphine, diisopropylazodicarboxylate and a base, such as, for example, triethylamine, can provide a phenolic ether compound 8-6, and the benzylic isomer compound 8-7 formed via C-alkylation of the phenol compound 8-5.

Scheme 9

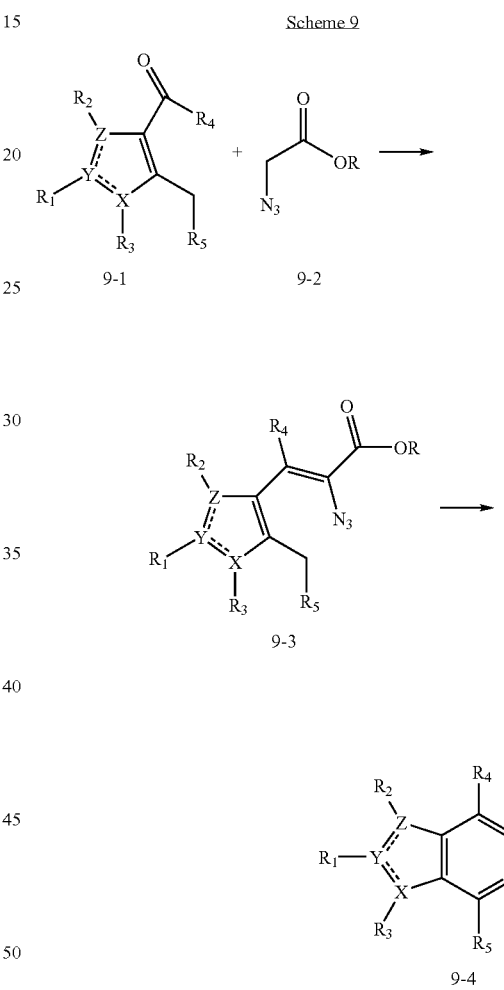

Scheme 8 depicts treating compound 7-3 where $R_3$=H and preferably R=an alkyl group (compound 8-1) in a fashion similar to the methods outlined in Scheme 4. Reaction of compound 8-1 with Eschenmoser' salt (Kozikowski, A. P. et al., *Heterocycles,* 14, pp. 55-58 (1980)) can give the dimethylaminomethyl derivative compound 8-2. Alternatively, this step can be performed using classic Mannich reaction conditions (review: Brewster, J. H. et al., *Org. Reactions,* 7, p. 99 (1953)). Upon treatment of compound 8-2 with sodium acetate and acetic anhydride in acetonitrile (Cocker, J. N. et al., *J. Org. Chem.,* 28, pp. 589-570 (1963)) the corresponding acetate 8-3 can be obtained which on hydrolysis with a base, such as, for example, potassium Scheme 9 depicts a general method for formation of compounds of general structure 1-1 described by Gilchrist, T. L. et al, *J. C. S. Chem. Comm., pp.* 627-628 (1979); Henn, L., *J. Chem. Soc. Perkin Trans.,* 1, pp. 2189-2196 (1984); and Shafiee, A. et al., *J. Heterocyclic Chem.,* 23, pp. 1171-1173 (1986). It is expected that reaction of a substituted heteroaromatic aldehyde or ketone compound 9-1 with ethyl or methyl azidoacetate compound 9-2 in the presence of a base, such as, for example, sodium hydride, will provide azidocinnamate compound 9-3, which on thermolysis in boiling toluene or xylene is expected to provide the desired product 9-4 (where preferably R=an alkyl group).

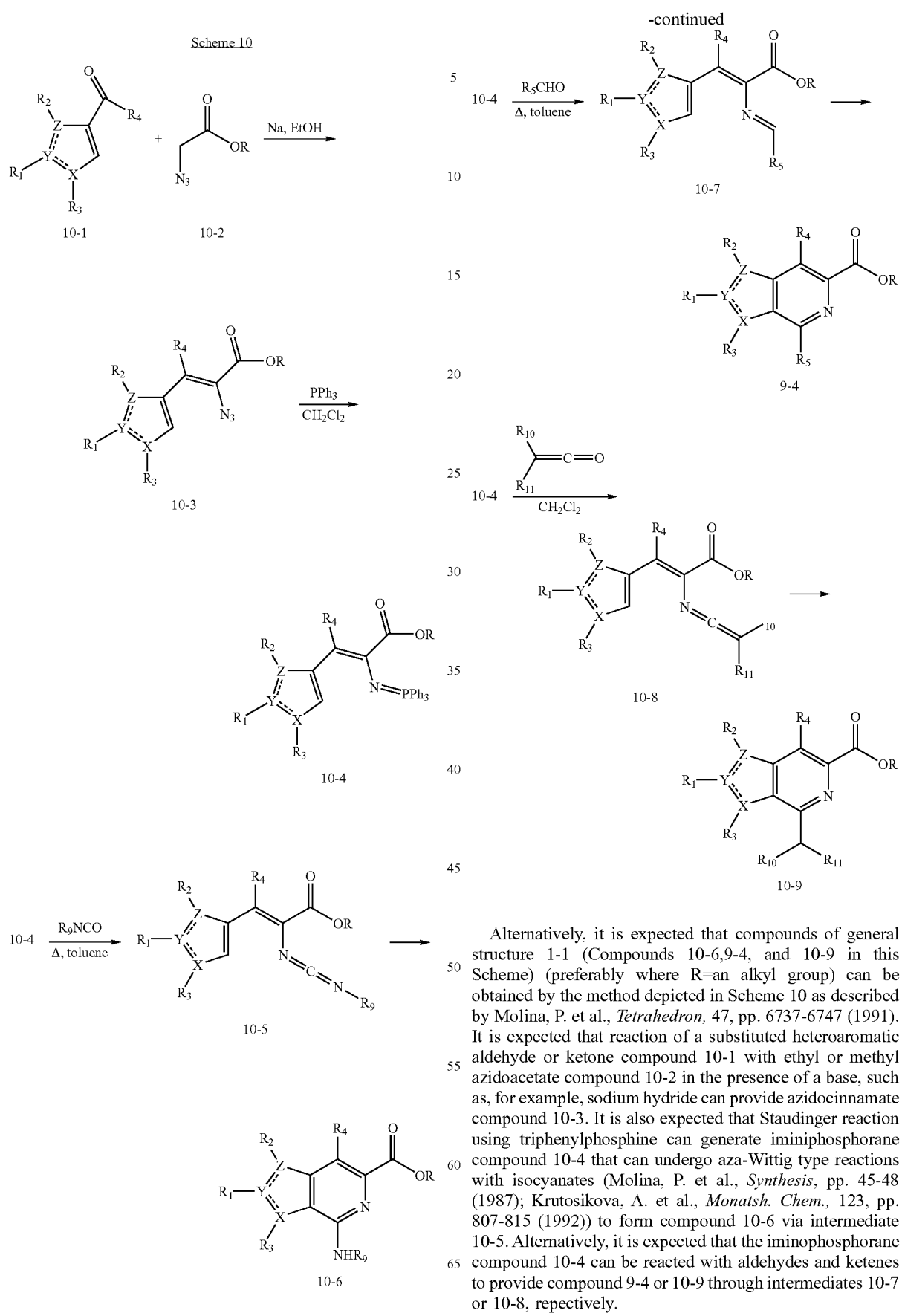

Alternatively, it is expected that compounds of general structure 1-1 (Compounds 10-6,9-4, and 10-9 in this Scheme) (preferably where R=an alkyl group) can be obtained by the method depicted in Scheme 10 as described by Molina, P. et al., *Tetrahedron,* 47, pp. 6737-6747 (1991). It is expected that reaction of a substituted heteroaromatic aldehyde or ketone compound 10-1 with ethyl or methyl azidoacetate compound 10-2 in the presence of a base, such as, for example, sodium hydride can provide azidocinnamate compound 10-3. It is also expected that Staudinger reaction using triphenylphosphine can generate iminiphosphorane compound 10-4 that can undergo aza-Wittig type reactions with isocyanates (Molina, P. et al., *Synthesis,* pp. 45-48 (1987); Krutosikova, A. et al., *Monatsh. Chem.,* 123, pp. 807-815 (1992)) to form compound 10-6 via intermediate 10-5. Alternatively, it is expected that the iminophosphorane compound 10-4 can be reacted with aldehydes and ketenes to provide compound 9-4 or 10-9 through intermediates 10-7 or 10-8, repectively.

Scheme 11

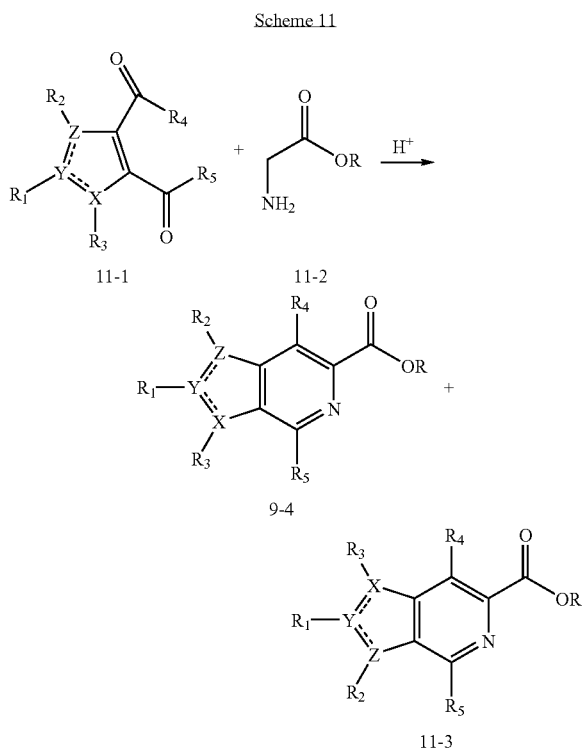

Another general method expected to provide the desired precursor compounds 1-1(Compound 9-4 in this Scheme) is depicted in Scheme 11. This method relies on the condensation of a dicarbonyl compound 11-1 with ethyl glycinate compound 11-2 (Mataka, S. et al., *J. Heterocyclic. Chem.,* 18, pp. 1073-1075 (1981); Kreher, R. P. et al., Chemiker-Zeitung, 9, pp. 275-277 (1984)) to provide a mixture of regioisomers compounds 9-4 and 11-3. The compounds 9-4 and 11-3 can be separated by column chromatography or any other methods known to persons skilled in the art.

Other compounds of Formula I may be prepared in manners analogous to the general procedures described above or the detailed procedures described in the following examples:

Example 1

1-(2,4-Difluorobenzyl)-N-hydroxy-1H-pyrrolo[2,3-c]pyridine-5-carboxamide

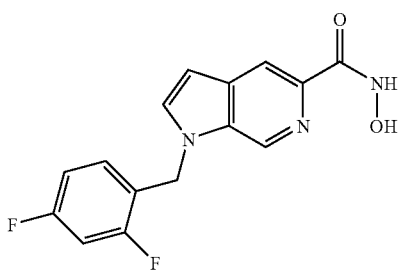

(a) Ethyl 1-(2,4-difluorobenzyl)-1H-pyrrolo[2,3-c]pyridine-5-carboxylate. To a stirred solution of ethyl 1H-pyrrolo[2,3-c]pyridine-5-carboxylate [prepared according to M. Dekhane, P. Potier, R. H. Dodd, Tetrahedron, 1993, 49, 8139-8146](0.50 g, 2.63 mmol) in DMF (10 mL) under a nitrogen atmosphere was added sodium hydride (0.087 g, 80% in mineral oil, 2.89 mmol) and 2,4-difluorobenzyl bromide (0.60 g, 2.89 mmol). The resulting mixture was stirred for 16 hours at ambient temperature. It was quenched with water (30 mL), and extracted with ethyl acetate (3×30 mL). The combined organic extracts were washed with water (2×30 mL), dried over sodium sulfate, concentrated in vacuo and purified by flash chromatography. Elution with hexane:ethyl acetate (1:1) provided the title compound as a light yellow solid (0.40 g, 48% yield). $^1$H NMR (CD$_3$OD) δ8.86 (s, 1H), 8.47 (s, 1H), 7.71 (d, 1H, J=3.2 Hz), 7.31 (dd, 1H, J=6.3 Hz), 6.94-7.05 (m, 2H), 6.79 (d, 1H, J=3.2 Hz), 5.63 (s, 2H), 4.46 (q, 2H, J=7.3 Hz), 1.45 (t, 3H, J=7.3 Hz). LCMS (API-ES, M+H$^+$): 317.0.

(b) 1-(2,4-Difluorobenzyl)-1H-pyrrolo[2,3-c]pyridine-5-carboxylic acid. To ethyl 1-(2,4-difluorobenzyl)-1H-pyrrolo[2,3-c]pyridine-5-carboxylate (0.30 g, 1.58 mmol) in methanol (3 mL) was added sodium hydroxide (0.076 g, 3.16 mmol) in water (0.5 mL). The reaction was heated in a SmithCreator™ (microwave reactor from Personal Chemistry) to 100° C. for five minutes. The reaction solution was poured into water (30 mL) and the pH was adjusted to 2-3 by addition of citric acid. The precipitate that formed was collected by filtration and dried in vacuo to provide the title compound as a white powder (0.15 g, 55% yield). $^1$H NMR (DMSO-d$_6$): δ: 8.97 (s, 1H), 8.35 (s, 1H), 7.82 (d, 1H, J=3.2 Hz), 7.28-7.38 (m, 2H), 7.09 (t, 1H, J=8.4 Hz), 6.76 (d, 1H, J=3.2 Hz), 5.67 (s, 2H). LCMS (API-ES, M+H$^+$): 289.1.

(c) 1-(2,4-Difluorobenzyl)-N-hydroxy-1H-pyrrolo[2,3-c]pyridine-5-carboxamide. To 1-(2,4-difluorobenzyl)-1H-pyrrolo[2,3-c]pyridine-5-carboxylic acid (0.15 g, 0.52 mmol) in DMF (10 mL) were added 0-(7-azabenzotriazol-1-yl)-1,1,3,3-tetramethyluronium hexafluorophosphate (HATU; 0.20 g, 0.52 mmol), triethylamine (0.15 ml, 1.05 mmol), and hydroxylamine hydrochloride (0.036 g, 0.52 mmol). The resulting mixture was stirred for 16 hours at ambient temperature. It was quenched with water (30 mL), extracted with ethyl acetate (3×30 mL). The combined organic extracts were washed with water (2×30 mL), dried over sodium sulfate, concentrated in vacuo and purified by preparative HPLC to provide the title compound as a white powder (0.075 g, 48% yield). $^1$H NMR (DMSO-d$_6$) δ: 11.14 (s, 1H), 8.92 (s, 1H), 8.85 (s, 1H), 8.21 (s, 1H), 7.78 (s, 1H), 7.26-7.38 (m, 2H), 7.08 (t, 1H, J=8.3 Hz), 6.71 (d, 1H, J=3.0 Hz), 5.64 (s, 2H). LCMS (API-ES, M+H$^+$): 304.1. HRMS calcd for C$_{15}$H$_{12}$F$_2$N$_3$O$_2$ (M+H) 304.0898, found 304.0886. HPLC: 98% purity.

Example 2

1-(2,4-Difluorobenzyl)-N-hydroxy-N-methyl-1H-pyrrolo[2,3-c]pyridine-5-carboxamide

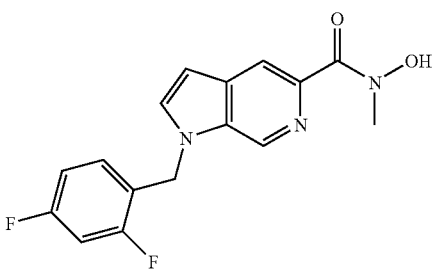

The title compound was prepared by coupling of 1-(2,4-difluorobenzyl)-1H-pyrrolo[2,3-c]pyridine-5-carboxylic acid and N-methyl hydroxylamine hydrochloride in a manner similar to step (c) of example 1. $^1$H NMR (DMSO-$d_6$) δ: 11.10 (br, 1H), 8.92 (s, 1H), 8.04 (s, 1H), 7.82 (s, 1H), 7.26-7.38 (m, 2H), 7.07-7.08 (m, 1H), 6.72 (s, 1H), 5.64 (s, 2H), 3.33 (s, 3H). LCMS (API-ES, M+H$^+$): 318.0. HRMS calcd for $C_{16}H_{14}F_2N_3O_2$(M+H) 318.1054, found 318.1037. HPLC: 100% purity.

Example 3

1-(4-Fluorobenzyl)-N-hydroxy-1H-pyrrolo[2,3-c]pyridine-5-carboxamide

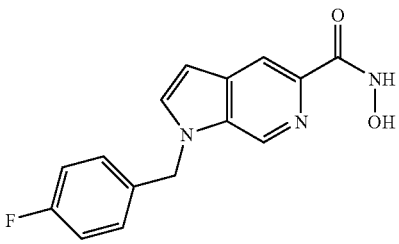

(a) Ethyl 1-(4-fluorobenzyl)-1H-pyrrolo[2,3-c]pyridine-5-carboxylate. The title compound was prepared by alkylation of ethyl 1H-pyrrolo[2,3-c]pyridine-5-carboxylate with 4-fluorobenzyl bromide in a manner similar to step (a) of example 1. $^1$H NMR (CD$_3$OD) δ: 8.91 (s, 1H), 8.62 (s, 1H), 7.90 (d, 1H, J=3.0 Hz), 7.42 (m, 2H), 7.20 (m, 2H), 6.90 (d, 1H, J=3.0 Hz), 5.75 (s, 2H), 4.60 (q, 2H, J=7.0 Hz), 1.60 (t, 3H, J=7.0 Hz). LCMS (API-ES, M+H$^+$): 299.1.

(b) 1-(4-Fluorobenzyl)-1H-pyrrolo[2,3-c]pyridine-5-carboxylic acid. The title compound was prepared by hydrolysis of ethyl 1-(4-fluoro-benzyl)-1H-pyrrolo[2,3-c]pyridine-5-carboxylate in a manner similar to step (b) of example 1. $^1$H NMR (DMSO-$d_6$): δ: 8.97 (s, 1H), 8.35 (s, 1H), 7.90 (d, 1H, J=3.0 Hz), 7.35 (m, 2 H), 7.15 (m, 2H), 6.76 (d, 1H, J=3.0 Hz), 5.67 (s, 2H). LCMS (API-ES, M+H$^+$): 271.1.

(c) 1-(4-Fluorobenzyl)-N-hydroxy-1H-pyrrolo[2,3-c]pyridine-5-carboxamide. The title compound was prepared by coupling of 1-(4-fluorobenzyl)-1H-pyrrolo[2,3-c]pyridine-5-carboxylic acid with hydroxylamine hydrochloride in a manner similar to step (c) of example 1. $^1$H NMR (DMSO-$d_6$) δ: 11.12 (s, 1H), 8.90 (s, 1H), 8.83 (s, 1H), 8.21 (s, 1H), 7.85 (d, 1H, J=3 Hz), 7.36 (d, 2H, J=8.3 Hz), 7.17 (d, 2H, J=8.4 Hz), 6.71 (d, 1H, J=3.0 Hz), 5.59 (s, 2H). LCMS (API-ES, M+H$^+$): 286.1. HRMS calcd for $C_{15}H_{13}FN_3O_2$ (M+H) 286.0992, found 286.0978. Anal. ($C_{15}H_{12}FN_3O_2$) C, H, N. HPLC: 96.6% purity.

Example 4

1-(4-Fluorobenzyl)-N-hydroxy-N-methyl-1H-pyrrolo[2,3-c]pyridine-5-carboxamide

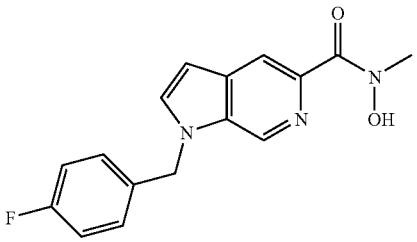

The title compound was prepared by coupling of 1-(4-fluorobenzyl)-1H-pyrrolo[2,3-c]pyridine-5-carboxylic acid with N-methyl hydroxylamine hydrochloride in a manner similar to step (c) of example 1. $^1$H NMR (DMSO-$d_6$) δ: 12.00 (br s, 1H), 8.91 (s, 1H), 8.03 (s, 1H), 7.91 (d, 1H, J=2.8 Hz), 7.38 (dd, 2H, J=5.7 Hz, J=8.5 Hz), 7.12 (d, 2H, J=8.5 Hz), 6.71 (d, 1H, J=3.0 Hz), 5.59 (s, 2H), 3.33 (s, 3H). LCMS (API-ES, M+H$^+$): 301.1. HRMS calcd for $C_{16}H_{15}FN_3O_2$ (M+H) 300.1148, found 300.1138. HPLC: 100% purity

Example 5

N-Benzyl-1-(4-fluorobenzyl)-N-hydroxy-1H-pyrrolo[2,3-c]pyridine-5-carboxamide

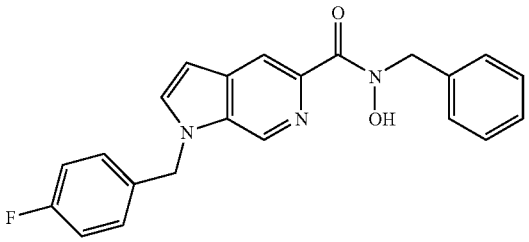

The title compound was prepared by coupling of 1-(4-fluorobenzyl)-1H-pyrrolo[2,3-c]pyridine-5-carboxylic acid with N-benzyl hydroxylamine hydrochloride in a manner similar to step (c) of example 1. $^1$H NMR (DMSO-$d_6$) δ: 8.92 (s, 1H), 8.11 (s, 1H), 7.91 (d, 1H, J=2.8 Hz), 7.26-7.38 (m, 7H), 7.16 (d, 2H, J=8.5 Hz), 6.72 (d, 1H, J=2.8 Hz), 5.58 (s, 2H), 4.97 (s, 2H). LCMS (API-ES, M+H$^+$): 376.1, HRMS calcd for $C_{22}H_{19}FN_3O_2$ (M+H) 376.1461, found 376.1448. Anal. ($C_{22}H_{18}FN_3O_2$) C, H, N. HPLC: 100% purity.

Example 6

1-(3-Chloro-2,6-difluorobenzyl)-N-hydroxy-1H-pyrrolo[2,3-c]pyridine-5-carboxamide

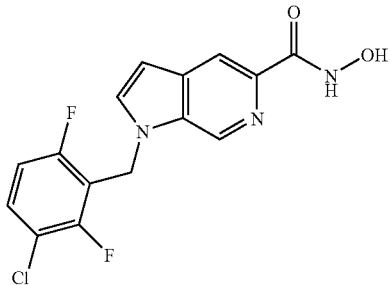

(a) Ethyl 1-(3-chloro-2,6-difluorobenzyl)-1H-pyrrolo[2,3-c]pyridine-5-carboxylate. The title compound was prepared by alkylation of ethyl 1H-pyrrolo[2,3-c]pyridine-5-carboxylate with 3-chloro-2,6-difluoro-benzyl bromide in a manner similar to step (a) of example 1. $^1$H NMR (CD$_3$OD) δ: 8.96 (s, 1H), 8.47 (s, 1H), 7.71 (d, 1H, J=3.0 Hz), 7.55 (m, 1H), 7.05 (m, 1H), 6.75 (d, 1H, J=3.0 Hz), 5.72 (s, 2H), 4.52 (q, 2H, J=7.3 Hz), 1.45 (t, 3H, J=7.3 Hz). LCMS (API-ES, M+H$^+$): 351.0.

(b) 1-(3-Chloro-2,6-difluorobenzyl)-1H-pyrrolo[2,3-c]pyridine-5-carboxylic acid. The title compound was prepared by hydrolysis of ethyl 1-(3-Chloro-2,6-difluoro-benzyl)-1H-pyrrolo[2,3-c]pyridine-5-carboxylate in a manner similar to step (b) of example 1. $^1$H NMR (DMSO-d$_6$): δ: 8.95 (s, 1H), 8.34 (s, 1H), 7.75 (d, 1H, J=3.2 Hz), 7.65-7.73 (m, 1H), 7.24-7.31 (m, 1H), 6.75 (d, 1H, J=3.2 Hz), 5.75 (s, 2H). LCMS (API-ES, M+H$^+$): 323.0.

(c) 1-(3-Chloro-2,6-difluorobenzyl)-N-hydroxy-1H-pyrrolo[2,3-c]pyridine-5-carboxamide. The title compound was prepared by coupling of 1-(1-(3-Chloro-2,6-difluoro-benzyl)-1H-pyrrolo[2,3-c]pyridine-5-carboxylic acid and hydroxylamine hydrochloride in a manner similar to step (c) of example 1. $^1$H NMR (DMSO-d$_6$) δ: 11.17 (s, 1H), 8.89 (s, 1H), 8.81 (s, 1H), 8.18 (s, 1H), 7.69-7.70 (m, 2H), 7.25 (m, 1H), 6.68 (s, 1H), 5.70 (s, 2H). LCMS (APCI, M+H$^+$): 338.0. HRMS (M+H) calcd for C$_{15}$H$_{11}$ClF$_2$N$_3$O$_2$ (M+H) 338.0508, found 338.0511. HPLC: 95% purity

Example 7

1-(5-Chloro-thiophen-2-ylmethyl)-N-hydroxy-1H-pyrrolo[2,3-c]pyridine-5-carboxamide

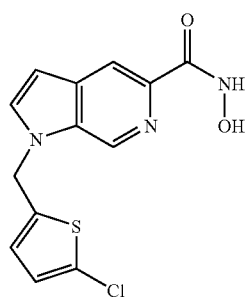

(a) Ethyl 1-(5-chloro-thiophen-2-ylmethyl)-1H-pyrrolo[2,3-c]pyridine-5-carboxylate. The title compound was prepared by alkylation of ethyl 1H-pyrrolo[2,3-c]pyridine-5-carboxylate with 2-chloro-5-(chloromethyl)-thiophene in a manner similar to step (a) of example 1. $^1$H NMR (CD$_3$OD) δ: 8.89 (s, 1H), 8.48 (s, 1H), 7.72 (d, 1H, J=3.2 Hz), 6.99 (d, 1H, J=3.8 Hz)), 6.87 (d, 1H, J=4.8 Hz), 6.75(d, 1H, J=3.2 Hz), 5.73 (s, 2H), 4.46 (q, 2H, J=7.2 Hz), 1.46 (t, 3H, J=7.2 Hz). LCMS (API-ES, M+H$^+$): 321.0.

(b) 1-(5-Chloro-thiophen-2-yl methyl)-1H-pyrrolo[2,3-c]pyridine-5-carboxylic acid. The title compound was prepared by hydrolysis of ethyl 1-(5-chloro-thiophen-2-ylmethyl)-1H-pyrrolo[2,3-c]pyridine-5-carboxylate in a manner similar to step (b) of example 1. $^1$H NMR (DMSO-d$_6$): δ: 9.05 (s, 1H), 8.34 (s, 1H), 7.88 (d, 1H, J=3.0 Hz), 7.12 (d, 1H, J=3.8 Hz), 7.01 (d, 1H, J=4.0 Hz), 6.75 (d, 1H, J=3.2 Hz), 5.78 (s, 2H). LCMS (API-ES, M+H$^+$): 293.0.

(c) 1-(5-Chloro-thiophen-2-yl methyl)-N-hydroxy-1H-pyrrolo[2,3-c]pyridine-5-carboxamide. The title compound was prepared by coupling of 1-(1-(5-Chloro-thiophen-2-ylmethyl)-1H-pyrrolo[2,3-c]pyridine-5-carboxylic acid with hydroxylamine hydrochloride in a manner similar to step (c) of example 1. $^1$H NMR (DMSO-d$_6$) δ: 11.15 (s, 1H), 8.93 (s, 2H), 8.21 (s, 1H), 7.81 (d, 1H, J=2.1 Hz), 7.10 (d, 1H, J=3.6 Hz), 6.99 (d, 1H, J=2.8 Hz), 6.70 (d, 1H, J=3.0 Hz), 5.76 (s, 2H). LCMS (API-ES, M+H$^+$): 308.0. HRMS calcd for C$_{13}$H$_{11}$N$_3$O$_2$SCl (M+H) 308.0261, found 308.0265. Anal. (C$_{13}$H$_{10}$ClN$_3$O$_2$S) C, H, N. HPLC: 100% purity.

Example 8

1-(3-Chloro-2-fluorobenzyl)-N-hydroxy-1H-pyrrolo[2,3-c]pyridine-5-carboxamide

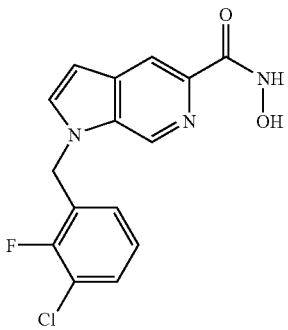

(a) Ethyl 1-(3-chloro-2-fluorobenzyl)-1H-pyrrolo[2,3-c]pyridine-5-carboxylate. The title compound was prepared by alkylation of ethyl 1H-pyrrolo[2,3-c]pyridine-5-carboxylate and 3-chloro-2-fluoro-benzyl bromide in a manner similar to step (a) of example 1. $^1$H NMR (CDCl$_3$) δ: 9.05 (s, 1H), 8.50 (s, 1H), 7.55 (d, 1H, J=3.0 Hz), 7.40 (m, 1H), 7.00 (m, 2H), 6.80 (d, 1H, J=3.0 Hz), 5.55 (s, 2H), 4.50 (q, 2H, J=7.0 Hz), 1.50 (t, 3H, J=7.0 Hz). LCMS (API-ES, M+H$^+$): 333.0.

(b) 1-(3-Chloro-2-fluorobenzyl)-1H-pyrrolo[2,3-c]pyridine-5-carboxylic acid. The title compound was prepared by hydrolysis of ethyl 1-(3-chloro-2-fluoro-benzyl)-1H-pyrrolo[2,3-c]pyridine-5-carboxylate in a manner similar to step (b) of example 1. $^1$H NMR (DMSO-d$_6$): δ: 8.96 (s, 1H), 8.35 (s, 1H), 7.84 (d, 1H, J=3.0 Hz), 7.56 (t, 1H, J=7.4 Hz), 7.19 (t, 1H, J=7.9 Hz), 7.09 (t, 1H, J=7.3 Hz), 5.75 (s, 2H). LCMS (API-ES, M+H$^+$): 305.0.

(c) 1-(3-Chloro-2-fluorobenzyl)-N-hydroxy-1H-pyrrolo[2,3-c]pyridine-5-carboxamide. The title compound was prepared by coupling of 1-(3-chloro-2-fluoro-benzyl)-1H-pyrrolo[2,3-c]pyridine-5-carboxylic acid with hydroxylamine hydrochloride in a manner similar to step (c) of example 1. $^1$H NMR (DMSO-d$_6$) δ: 11.16 (s, 1H), 8.95 (s, 1H), 8.85 (s, 1H), 8.23 (s, 1H), 7.79 (d, 1H, J=2.8 Hz), 7.55 (t,1H, J=7.5 Hz), 7.19 (t, 1H, J=7.5 Hz), 7.10 (t, 1H, J=7.5 Hz), 6.73 (d, 1H, J=3.0 Hz), 5.74 (s, 2H). LCMS (API-ES, M+H$^+$): 320.0. HRMS calcd for C$_{15}$H$_{12}$ClFN$_3$O$_2$ (M+H) 320.0602, found 320.06045. HPLC: 100% purity.

Example 9

(1-(2,3-Dichlorobenzyl)-N-hydroxy-1H-pyrrolo[2,3-c]pyridine-5-carboxamide

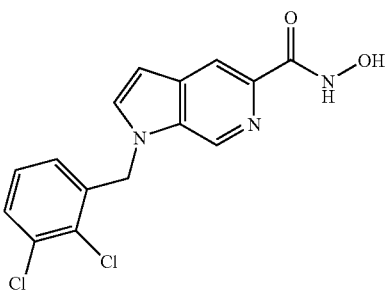

(a) Ethyl 1-(2,3-dichlorobenzyl)-1H-pyrrolo[2,3-c]pyridine-5-carboxylate. The title compound was prepared by alkylation of ethyl 1H-pyrrolo[2,3-c]pyridine-5-carboxylate with 2,3-dichlorobenzyl chloride in a manner similar to step (a) of example 1. $^1$H NMR (DMSO-d$_6$) δ: 9.15 (s, 1H), 8.63 (s, 1H), 8.04 (d, 1H, J=3.0 Hz), 7.85 (d, 1H, J=8.1 Hz), 7.52 (t, 1H, J=7.9 Hz), 7.04 (d, 1H, J=3.0 Hz), 6.91 (d, 1H, J=7.9 Hz), 6.01 (s, 2H), 4.56 (q, 2H, J=7.2 Hz), 1.57 (t, 3H, J=7.0 Hz). LCMS (API-ES, M+H$^+$): 349.0, 351.0, 353.0 (10:6:1).

(b) 1-(2,3-Dichlorobenzyl)-1H-pyrrolo[2,3-c]pyridine-5-carboxylic acid. The title compound was prepared by hydrolysis of 1-(2,3-dichloro-benzyl)-1H-pyrrolo[2,3-c]pyridine-5-carboxylic acid ethyl ester in a manner similar to step (b) of example 1. $^1$H NMR (DMSO-d$_6$): δ: 8.92 (s, 1H), 8.40 (s, 1H), 7.83 (d, 1H, J=3.0 Hz), 7.62 (d, 1H, J=7.4 Hz), 7.30 (t, 1H, J=7.8 Hz), 6.83 (d, 1H, J=3.0 Hz), 6.68 (d, 1H, J=7.9 Hz), 5.79 (s, 2H). LCMS (API-ES, M+H$^+$): 320.9, 323.0, 325.0 (10:6:1).

(c) (1-(2,3-Dichlorobenzyl)-N-hydroxy-1H-pyrrolo[2,3-c]pyridine-5-carboxamide. The title compound was prepared by coupling of 1-(2,3-dichloro-benzyl)-1H-pyrrolo[2,3-c]pyridine-5-carboxylic acid with hydroxylamine hydrochloride in a manner similar to step (c) of example 1. $^1$H NMR (DMSO-d$_6$) δ: 11.15 (s, 1H), 8.91 (s, 1H), 8.78 (s, 1H), 8.24 (s, 1H), 7.76 (d, 1H, J=3.2 Hz), 7.60 (d, 1H, J=8.1 Hz), 7.28 (t, 1H, J=8.1 Hz), 6.76 (d, 1H, J=3.0 Hz), 6.67 (d, 1H, J=7.7 Hz), 5.75 (s, 2H). LCMS (API-ES, M+H$^+$): 336.0, 338.0, 340.0 (10:6:1). HRMS calcd C$_{15}$H$_{12}$Cl$_2$N$_3$O$_2$(M+H) 336.0303, found 336.0300. HPLC: 100% purity Example 10

1-(5-Ethoxy-[1,2,3]thiadiazol-4-ylmethyl)-N-hydroxy-1H-pyrrolo[2,3-c]pyridine-5-carboxamide

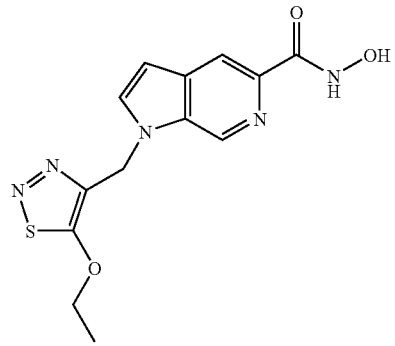

(a) Ethyl 1-(5-chloro-[1,2,3]thiadiazol-4-ylmethyl)-1H-pyrrolo[2,3-c]pyridine-5-carboxylate. The title compound was prepared by alkylation of ethyl 1H-pyrrolo[2,3-c]pyridine-5-carboxylate and 5-chloro-4-chloromethyl-[1,2,3]thiadiazole in a manner similar to step (a) of example 1. $^1$H NMR (DMSO-d$_6$) δ: 8.99 (s, 1H), 8.36 (s, 1H), 7.85 (d, 1H, J=3.0 Hz), 6.75 (d, 1H, J=3.0 Hz), 6.04 (s, 2H), 4.32 (q, 2H, J=7.0 Hz), 1.32 (t, 3H, J=7.0 Hz). LCMS (API-ES, M+H$^+$): 323.0.

(b) 1-(5-Ethoxy-[1,2,3]thiadiazol-4-ylmethyl)-1H-pyrrolo[2,3-c]pyridine-5-carboxylic acid. The title compound was prepared by hydrolysis of ethyl 1-(5-chloro-[1,2,3]thiadiazol-4-ylmethyl)-1H-pyrrolo[2,3-c]pyridine-5-carboxylate in a manner similar to step (b) of example 1 using sodium hydroxide as base and anhydrous ethanol as solvent. $^1$H NMR (DMSO-d$_6$): δ: 9.01 (s, 1H), 8.35 (s, 1H), 7.85 (d, 1H, J=3.0 Hz), 6.75 (d, 1H, J=3.0 Hz), 5.86 (s, 2H), 4.36 (q, 2H, J=6.8 Hz), 1.42 (t, 3H, J=6.8 Hz). LCMS (API-ES, M+H$^+$): 305.0.

(c) 1-(5-Ethoxy-[1,2,3]thiadiazol-4-ylmethyl)-N-hydroxy-1H-pyrrolo[2,3-c]pyridine-5-carboxamide. The title compound was prepared by coupling of 1-(5-ethoxy-[1,2,3]thiadiazol-4-ylmethyl)-1H-pyrrolo[2,3-c]pyridine-5-carboxylic acid and hydroxylamine hydrochloride in a manner similar to step (c) of example 1. $^1$H NMR (DMSO-d$_6$) 6; 11.15 (s, 1H), 8.88 (s, 2H), 8.19 (s, 1H), 7.73 (d, 1H, J=3.0 Hz), 6.66 (d, 1H, J=3.0 Hz), 5.81 (s, 2H), 4.32 (q, 2H, J=6.8 Hz), 1.39 (t, 3H, J=6.9 Hz). LCMS (APCI, M+H$^+$): 320.1. HRMS calcd for C$_{13}$H$_{14}$N$_5$O$_3$S (M+H) 320.0817, found 320.0823. HPLC: 100% purity.

Example 11

1-(2,4-Difluorobenzyl)-3-ethoxymethyl-N-hydroxy-1H-pyrrolo[2,3-c]pyridine-5-carboxamide

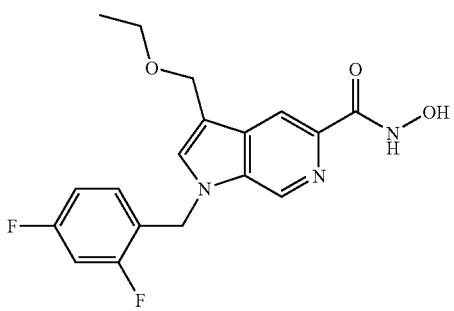

(a) Ethyl 1-(2,4-difluorobenzyl)-3-dimethylaminomethyl-1H-pyrrolo[2,3-c]pyridine-5-carboxylate. A solution of ethyl 1-(2,4-difluoro-benzyl)-1H-pyrrolo[2,3-c]pyridine-5-carboxylate (1.5 g, 4.74 mmol) in acetonitrile (50 mL) was refluxed for 16 h under nitrogen. The reaction mixture was cooled, quenched with saturated aqueous sodium bicarbonate solution (30 mL), and extracted with ethyl acetate (3×30 mL). The combined organic extracts were dried over sodium sulfate, concentrated and purified by flash chromatograph with methanol/dichloromethane (1:10) to provide the title compound (1.5 g, yield 85% ). $^1$H NMR (DMSO-$d_6$) δ: 8.92 (s, 1H), 8.36 (s, 1H), 7.67 (s, 1H), 7.25-7.36 (m, 2H), 6.04 -7.07 (m, 1H), 5.60 (s, 2H), 4.30 (q, 2H, J=7.0 Hz), 3.57 (s, 2H), 2.13 (s, 6H), 1.31 (t, 3H, J=7.0 Hz). LCMS (APCI, M+H$^+$): 374.2.

(b) Ethyl 3-acetoxymethyl-1-(2,4-difluorobenzyl)-1H-pyrrolo[2,3-c]pyridine-5-carboxylate. A solution of ethyl 1-(2,4-difluoro-benzyl)-3-dimethylaminomethyl-1H-pyrrolo[2,3-c]pyridine-5-carboxylate (1.0 g, 2.68 mmol) in anhydrous acetic anhydride (20 mL) containing dry sodium acetate (0.44 g, 5.36 mmol) was refluxed for 4 h under nitrogen. The reaction mixture was cooled, saturated aqueous sodium bicarbonate solution (30 mL) was added and the solution was extracted with ethyl acetate (3×30 mL). The combined organic extracts dried over sodium sulfate, concentrated and dried in vacuo to provide the title compound as a solid (1.0 g, 96% yield).1H NMR (CDCl$_3$) δ; 8.85 (s, 1H), 8.53 (s, 1H), 7.44 (s, 1H), 7.07 -7.09 (m, 1H), 6.08-6.87 (m, 2H), 5.40 (s, 2H), 5.28 (s, 2H), 4.49 (q, 2H, J=7.2 Hz), 2.03 (s, 3H), 1.43-1.48 (t, 3H, J=7.2 Hz). LCMS (APCI, M+H$^+$): 389.1.

(c) Ethyl 1-(2,4-difluorobenzyl)-3-hydroxymethyl-1H-pyrrolo[2,3-c]pyridine-5-carboxylate. To ethyl 3-acetoxymethyl-1-(2,4-difluoro-benzyl)-1H-pyrrolo[2,3-c]pyridine-5-carboxylate (1.0 g, 2.58 mmol) in ethanol (50 mL) and water (0.5 mL) was added potassium carbonate (0.21 g, 1.52 mmol). The mixture was stirred at ambient temperature for 3 hours, quenched with water (30 mL), extracted with ethyl acetate (3×30 mL). The combined organic extracts were dried over sodium sulfate, concentrated and dried in vacuo to provide the title compound (0.85 g, quant.). $^1$H NMR (CD$_3$OD) δ: 8.85 (s, 1H), 8.53 (s, 1H), 7.44 (s, 1H), 7.05-7.10 (m, 1H), 6.79-6.90 (m, 2H), 5.40 (s, 2H), 5.28 (s, 2H), 4.49-4.53 (q, 2H, J=7.0 Hz), 1.46 (t, 3H, J=7.0 Hz). LCMS (APCI, M+H$^+$): 347.1.

(d) Ethyl 1-(2,4-difluorobenzyl)-3-ethoxymethyl-1H-pyrrolo[2,3-c]pyridine-5-carboxylate. A single neck 25 mL flask with magnetic stir bar was dried in vacuum with heat and then nitrogen gas was introduced into flask at ambient temperature. To ethyl 1-(2,4-difluorobenzyl)-3-hydroxymethyl-1H-pyrrolo[2,3-c]pyridine-5-carboxylic acid (0.28 g, 0.81 mmol) in anhydrous DMF (5 mL) was added sodium hydride (0.026 g, 80% in mineral oil, 0.87 mmol). The resulting mixture was stirred at ambient temperature for five minutes and iodoethane (0.07 mL, 1.36 g, 0.88 mmol) was added to the flask. The mixture was stirred 16 hours at ambient temperature, quenched with water (30 mL), and extracted with ethyl acetate (3×30 mL). The combined organic extracts were dried over sodium sulfate, concentrated and purified by flash chromatography. Elution with ethyl acetate provided the title product as a solid (0.15 g, 50% yield ). $^1$H NMR (CD$_3$OD) δ: 8.87 (s, 1H), 8.53 (s, 1H), 7.71 (s, 1H), 7.30-7.36 (m, 1H), 6.94-7.08 (m, 2H), 6.62 (s, 2H), 4.76 (s, 2H), 4.46 (q, 2H, J=7.1 Hz), 3.62 (q, 2H, J=7.0 Hz), 1.46 (t, 3H, J=7.1 Hz), 1.25 (t, 3H, J=7.0 Hz). LCMS (API-ES, M+H$^+$): 375.0.

(e) 1-(2,4-Difluorobenzyl)-3-ethoxymethyl-N-hydroxy-1H-pyrrolo[2,3-c]pyridine-5-carboxamide. To ethyl 1-(2,4-difluoro-benzyl)-3-ethoxymethyl-1H-pyrrolo[2,3-c]pyridine-5-carboxylate (0.13 g, 0.35 mmol) in methanol (10 mL) were added hydroxylamine (2.0 mL, 50% in water, 33.3 mmol) and sodium hydroxide solution (1.0 mL, 1 N aqueous solution, 1.0 mmol) at ambient temperature. The solution was stirred at ambient temperature for 5 hours. The solution was concentrated until the product precipitated out. It was collected by filtration, and successively washed with water (10 mL) and ethyl acetate/hexane 1:1 (10 mL), and recrystallized from ethanol to give pure title compound (0.050 g, 39% yield). $^1$H NMR (DMSO-$d_6$) δ: 11.18 (s, 1H), 8.94 (s, 1H), 8.86 (s, 1H), 8.23 (s, 1H), 7.75 (s, 1H), 7.33-7.39 (m, 2H), 7.10 (m, 1H), 5.62 (s, 2H), 4.64 (s, 2H), 3.51 (q, 2H, J=6.9 Hz), 1.17 (t, 3H, J=7.0 Hz). LCMS (API-ES, M+H$^+$): 362.0. HRMS calcd for $C_{18}H_{18}F_2N_3O_3$ (M+H) 362.1316, found 362.1309. Anal. ($C_{18}H_{17}F_2N_3O_3$) C, H, N. HPLC: 98.0% purity

Example 12

1-(2,4-Difluorobenzyl)-N-hydroxy-4-methyl-1H-pyrrolo[2,3-c]pyridine-5-carboxamide

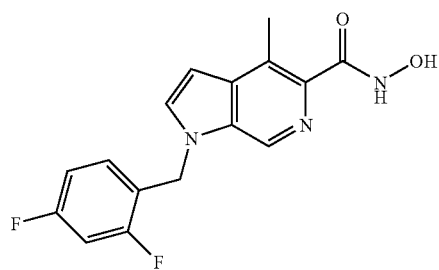

(a) Methyl 1-(2,4-difluorobenzyl)-4-methyl-1H-pyrrolo[2,3-c]pyridine-5-carboxylate. The title compound was prepared by alkylation of methyl 4-methyl-1H-pyrrolo[2,3-c]pyridine-5-carboxylate [prepared according to X. Doisy et al., Bioorg. Med. Chem. 1999, 7, 921-932) with 2,4-difluoro-benzyl bromide in a manner similar to step (a) of example 1. $^1$H NMR (CDCl$_3$) δ: 8.75 (s, 1H), 7.75 (d, 1H, J=3.0 Hz), 7.20 (m, 2H), 7.10 (m, 1H), 6.80 (d, 1H, J=3.0 Hz), 5.60 (s, 2H), 3.80 (s, 3H), 2.65 (s, 3H). LCMS (API-ES, M+H$^+$): 317.1.

(b) 1-(2,4-Difluorobenzyl)-N-hydroxy-4-methyl-1H-pyrrolo[2,3-c]pyridine-5-carboxamide. The title compound was prepared from 1-(2,4-difluoro-benzyl)-1H- pyrrolo[2,3-c]pyridine-5-carboxylic acid methyl ester in a manner similar to step (e) of example 11. $^1$H NMR (DMSO-d$_6$) δ: 10.82 (s, 1H), 8.86 (broad s, 1H), 8.67 (s, 1H), 7.73 (d, 1H, J=3.0 Hz), 7.25-7.32 (m, 2H), 7.02-7.09 (m, 1H), 6.73 (d, 1H, J=3.0 Hz), 5.60 (s, 2H), 2.66 (s, 3H). LCMS (APCI, M+H$^+$): 318.0. HRMS calcd for C$_{16}$H$_{14}$F$_2$N$_3$O$_2$ (M+H) 318.1054, found 318.1044. HPLC: 95.1% purity.

Example 13

1-(2,4-Difluorobenzyl)-N-hydroxy-3-hydroxymethyl-1H-pyrrolo[2,3-c]pyridine-5-carboxamide

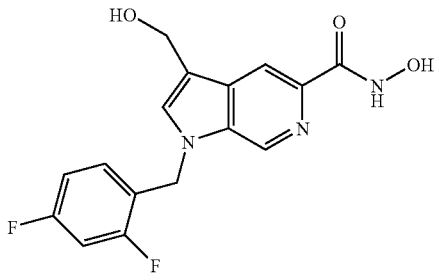

The title compound was prepared from ethyl 1-(2,4-difluoro-benzyl)-3-hydroxymethyl-1H-pyrrolo[2,3-c]pyridine-5-carboxylate in a manner similar to step (e) of example 11. $^1$H NMR (CD$_3$OD) δ: 8.79 (s, 1H), 8.43 (s, 1H), 7.62 (s, 1H), 7.24-7.32 (m, 1H), 7.01 (m, 1H), 7.92-6.98 (m, 1H), 5.58 (s, 2H), 4.84 (s, 2H). LCMS (API-ES, M+H$^+$): 334.1. HRMS calcd for C$_{16}$H$_{14}$F$_2$N$_3$O$_3$(M+H) 334.1003, found 334.0998. Anal. (C$_{16}$H$_{14}$F$_2$N$_3$O$_3$) C, H, N. HPLC: 100% purity.

Example 14

1-(2,4-Difluorobenzyl)-3-dimethylaminomethyl-N-hydroxy-1H-pyrrolo[2,3-c]pyridine-5-carboxamide

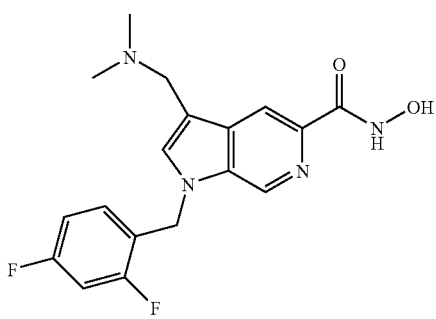

The title compound was prepared from ethyl 1-(2,4-difluoro-benzyl)-3-dimethylaminomethyl-1H-pyrrolo[2,3-c]pyridine-5-carboxylate in a manner similar to step (e) of example 11. $^1$H NMR (CD$_3$OD) δ: 8.81 (s, 1H), 8.41 (s, 1H), 7.72 (s, 1H), 7.33 (m, 1H), 7.03 (m, 2H), 5.60 (s, 2H), 4.06 (s, 2H), 2.52 (s, 6H). LCMS (API-ES, M+H$^+$): 361.1 HRMS calcd for C$_{18}$H$_{19}$F$_2$N$_4$O$_3$ (M+H) 361.1474, found 361.1483. HPLC: 100% purity.

Example 15

3-Benzyloxymethyl-1-(2,4-difluorobenzyl)-N-hydroxy-1H-pyrrolo[2,3-c]pyridine-5-carboxamide

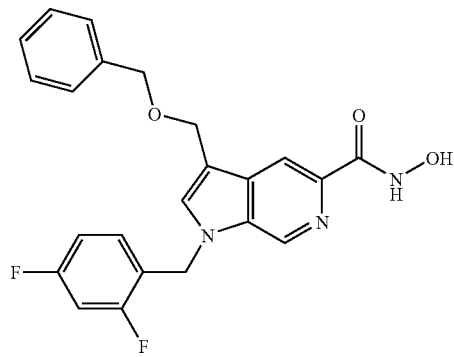

(a) Ethyl 3-benzyloxymethyl-1-(2,4-difluorobenzyl)-1H-pyrrolo[2,3-c]pyridine-5-carboxylate. The title compound was prepared by alkylation of ethyl 1-(2,4-difluoro-benzyl)-3-hydroxymethyl-1H-pyrrolo[2,3-c]pyridine-5-carboxylate and benzyl bromide in a manner similar to step (d) of example 11. $^1$H NMR (CD$_3$OD) δ; 8.83 (s, 1H), 8.48 (s, 1H), 7.68 (s, 1H), 7.34 (m, 6H), 7.02 (m, 2H), 5.58 (s, 2H), 4.76 (s, 2H), 4.56 (s, 2H), 4.44 (q, 2H, J=7.0 Hz), 1.43 (t, 3H, J=7.0 Hz). LCMS (API-ES, M+H$^+$): 437.1.

(b) 3-Benzyloxymethyl-1-(2,4-difluorobenzyl)-N-hydroxy-1H-pyrrolo[2,3-c]pyridine-5-carboxamide. The title compound was prepared from ethyl 3-benzyloxymethyl-1-(2,4-difluorobenzyl)-1H-pyrrolo[2,3-c]pyrid example 11. $^1$H NMR (DMSO-d$_6$) δ: 11.16 (s, 1H), 8.95 (s, 1H), 8.84 (s, 1H), 8.25 (s, 1H), 7.77 (s, 1H), 7.01 (m, 1H), 7.31 (m, 7H), 7.07 (m, 1H), 5.61 (s, 2H), 4.71 (s, 2H), 4.51 (s, 2H). LCMS (API-ES, M+H$^+$): 424.1. HRMS calcd for C$_{23}$H$_{20}$F$_2$N$_3$O$_3$ (M+H) 424.1473, found 424.1472. Anal. (C$_{23}$H$_{19}$F$_2$N$_3$O$_3$) C, H, N. HPLC: 100% purity.

Example 16

3-(2,4-Difluorobenzyl)-N-hydroxy-3H-imidazo[4,5-c]pyridine-6-carboxamide

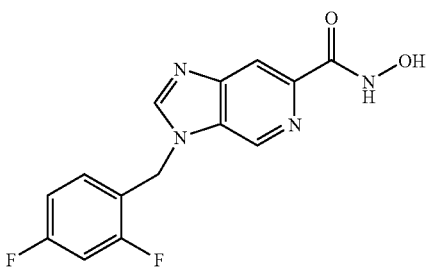

(a) (6S)-4,5,6,7-Tetrahydro-3H-imidazo[4,5-c]pyridine-6-carboxylic acid dihydrochloride. L-histidine (204.8 g, 1.32 mol) was added to water (1.2 L) and cooled on an ice/water bath. Concentrated hydrochloric acid (116.0 mL, 1.39 mol, 1.05 mol eqv.) was added slowly. Formaldehyde, 37 wt/wt % in water (112.5 g, 1.39 mol, 1.05 mol eqv.) was added in one portion. The reaction mixture was stirred for 30 min upon cooling on an ice/water bath, and then refluxed for 75 min. After cooling to room temperature, the solvent was removed under reduced pressure. The residue was suspended in isopropanol (2 L) and HCl (400 mL of a 4 M solution in dioxane) for 30 min. The white solid was filtered and washed with ether. After drying in a vacuum oven (40° C.), the title product was obtained. (313.0 g, 99% yield, 95% pure). $^1$H NMR (DMSO-$d_6$): δ: 3.05-3.33 (m, 2H), 4.30 (s, 2H), 4.54 (m, 1H), 9.00 (s, 1H), 12.60 (br s, 3H). LC-MS: Rt=0.59 min, and M+1=168.1 m/z (M+1 of free base).

(b) Methyl (6S)-4,5,6,7-tetrahydro-3H-imidazo[4,5-c]pyridine-6-carboxylate dihydrochloride. Thionylchloride (200 mL, 2.74 mol, 3.0 mol eqv.) was added dropwise to methanol (3.5 L), which was cooled to 0-5° C. (6S)-4,5,6,7-tetrahydro-3H-imidazo[4,5-c]pyridine-6-carboxylic acid dihydrochloride (210.0 g, 0.87 mol) was added, and the suspension was allowed to warm up to room temperature, and refluxed for 3.5 h. After cooling to room temperature, the solvent was removed under reduced pressure. The white residue was suspended in ether (3 L). The solid was filtered and washed with ether. After drying in a vacuum oven (40° C.), the title compound was obtained (225.0 g, 100% yield, 95% pure). $^1$H NMR (DMSO-$d_6$): δ: 12.65 (br s, 2H), 9.04 (s, 1H), 4.71 (m, 1H), 4.33 (t, J=16.2 Hz, 2H), 3.81 (s, 3H), 3.10-3.33 (m, 2H), LC-MS: Rt=0.61 min, and M+1=182.1 m/z (M+1 of free base).

(c) Methyl 3H-imidazo[4,5-c]pyridine-6-carboxylate. Methyl (6S)-4,5,6,7-tetrahydro-3H-imidazo[4,5-c]pyridine-6-carboxylate dihydrochloride (156.5 g, 0.62 mol), triethylamine (445.0 g, 4.4 mol, 7.0 mol eqv.), selenium dioxide (158.2 g, 1.43 mol, 2.3 mol eqv.), and polyphosphatesilyl ether (PPSE) (15.0 g) were added to $CCl_4$ (1.5 L). The mixture was refluxed for 6 h. After cooling to room temperature, the solvent was removed under reduced pressure. The residue was suspended in methanol (1.5 L), and triethylamine was added to adjust to pH 8. The brown solid was filtered and washed well with methanol. This brown solid (117.0 g) was recrystallized from hot DMF (2 L)/140° C. The solution was filtered hot to remove black side product of selenium salt. Upon cooling to room temperature, the desired product crystallized out as a yellow solid (51.3 g, 47% yield, 95% pure). $^1$H NMR (DMSO-$d_6$): δ: 13.20 (br s, 1H), 9.02 (s, 1H), 8.58 (s, 1H), 8.31 (s, 1H), 3.89 (s, 3H); LCMS: Rt=1.33 min, and M+1=178.1 m/

(d) Methyl 3-(2,4-difluorobenzyl)-3H-imidazo[4,5-c]pyridine-6-carboxylate and methyl 1-(2,4-difluorobenzyl)-1H-imidazo[4,5-c]pyridine-6-carboxylate. The title compounds were prepared by alkylation of methyl1 H-imidazo[4,5-c]pyridine-6-carboxylate with 2,4-difluorobenzyl bromide in a manner similar to step (a) of example 1. The two regioisomers were separated by column chromatograph using ethyl acetate as eluent and characterized by Roesy $^1$H NMR.

Methyl 3-(2,4-difluorobenzyl)-3H-imidazo[4,5-c]pyridine-6-carboxylate: Rf: 0.29 (ethyl acetate); $^1$H NMR (CD$_3$OD) δ: 9.02 (s, 1H), 8.70 (s, 1H), 8.34 (s, 1H), 7.53-7.59 (m, 1H), 7.30-7.33 (m, 1H), 7.09-7.12 (m, 1H), 5.71 (s, 2H), 3.87 (s, 3H). LCMS (API-ES, M+H$^+$): 304.0. Methyl 1-(2,4-difluorobenzyl)-1H-imidazo[4,5-c]pyridine-6-carboxylate: Rf: 0.18 (ethyl acetate); $^1$H NMR (CD$_3$OD) δ: 9.03 (s, 1H), 8.68 (s, 1H), 8.40 (s, 1H), 7.45-7.51 (m, 1H), 7.29-7.31 (m, 1H), 7.09-7.11 (m, 1H), 5.69 (s, 2H), 3.88 (s, 3H). LCMS (, API-ES, M+H$^+$): 304.1.

(e) 3-(2,4-Difluorobenzyl)-N-hydroxy-3H-imidazo[4,5-c]pyridine-6-carboxamide. The title compound was prepared from methyl 3-(2,4-difluorobenzyl)-3H-imidazo[4,5-c]pyridine-6-carboxylate in a manner similar to step (e) of example 11. $^1$H NMR (DMSO-$d_6$) δ: 11.27 (s, 1H), 9.00 (s, 1H), 8.88 (s, 1H), 8.66 (s, 1H), 8.19 (s, 1H), 7.58 (m,1H), 7.31 (m, 1H), 7.11 (m, 1H), 5.70 (s, 2H). LCMS (API-ES, M+H$^+$): 305.0. HRMS calcd for $C_{14}H_{11}F_2N_4O_2$ (M+H) 305.0850, found 305.0837. HPLC: 100% purity.

Example 17

1-(2,4-Difluorobenzyl)-N-hydroxy-1H-imidazo[4,5-c]pyridine-6-carboxamide

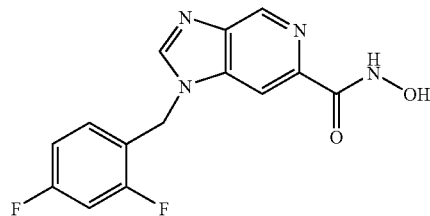

The title compound was prepared from methyl 1-(2,4-difluoro-benzyl)-1H-imidazo[4,5-c]pyridine-6-carboxylate in a manner similar to step (e) of example 11. $^1$H NMR (DMSO-$d_6$) δ: 11.36 (s, 1H), 9.00 (s, 1H), 8.93(s, 1H), 8.61 (s, 1H), 8.25 (s, 1H), 7.49 (m, 1H), 7.30 (m, 1H), 7.11 (m, 1H), 5.68 (s, 2H). LCMS (API-ES, M+H$^+$): 305.0. HRMS calcd for $C_{14}H_{11}F_2N_4O_2$. (M+H) 305.0850, found 305.0838. HPLC: 100% purity.

Example 18

1-(2,4-Difluorobenzyl)-3-ethoxymethyl-N-hydroxy-N-methyl-1H-pyrrolo[2,3-c]pyridine-5-carboxamide

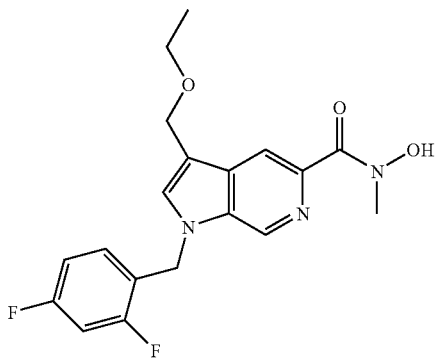

(a) 1-(2,4-Difluorobenzyl)-3-ethoxymethyl-1H-pyrrolo[2,3-c]pyridine-5-carboxylic acid. The title compound was prepared by hydrolysis of ethyl 1-(2,4-difluorobenzyl)-3-ethoxymethyl-1H-pyrrolo[2,3-c]pyridine-5-carboxylate in a manner similar to step (b) of example 1. $^1$H NMR (DMSO-d$_6$). δ: 8.96 (s, 1H), 8.34 (s, 1H), 7.78 (s, 1H), 7.08-7.40 (m, 2H), 7.07 (m, 1H), 5.62 (s, 2H), 4.63 (s, 2H), 3.48 (q, 2H, J=7.0 Hz), 1.11 (t, 3H, J=7.0 Hz). LCMS (API-ES, M+H$^+$): 347.0.

(b) 1-(2,4-Difluorobenzyl)-3-ethoxymethyl-N-hydroxy-N-methyl-1H-pyrrolo[2,3-c]pyridine-5-carboxamide. The title compound was prepared by coupling of 1-(2,4-difluorobenzyl)-3-ethoxymethyl-1H-pyrrolo[2,3-c]pyridine-5-carboxylic acid and N-methyl hydroxylamine hydrochloride in a manner similar to step (c) of example 1. $^1$H NMR (CD$_3$OD) δ: 8.81 (s, 1H), 8.27 (s, 1H), 7.71 (s, 1H), 7.29 -7.30 (m, 1H), 6.98 -7.30 (m, 2H), 5.58 (s, 2H), 4.72 (s, 2H), 3.59 (q, 2H, J=7.0 Hz), 3.43 (s, 3H), 1.20 (t, 3H, J=7.0 Hz). LCMS (APCI, M+H$^+$): 376.1. HRMS calcd for C$_{19}$H$_{20}$F$_2$N$_3$O$_3$ (M+H) 376.1473, found 376.1454. Anal. (C$_{19}$H$_{19}$F$_2$N$_3$O$_3$× 0.2H$_2$O) C, H, N. HPLC: 100% purity.

Example 19

1-(2,4-Difluorobenzyl)-N-hydroxy-3-hydroxymethyl-N-methyl-1H-pyrrolo[2,3-c]pyridine-5-carboxamide

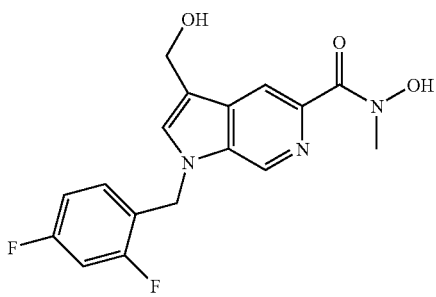

(a) 1-(2,4-Difluorobenzyl)-3-hydroxymethyl-1H-pyrrolo[2,3-c]pyridine-5-carboxylic acid. The title compound was prepared by hydrolysis of ethyl 1-(2,4-difluoro-benzyl)-3-hydroxymethyl-1H-pyrrolo[2,3-c]pyridine-5-carboxylate in a manner similar to step (b) of example 1. $^1$H NMR (DMSO-d$_6$). δ: 8.96 (s, 1H), 8.41 (s, 1H), 7.69 (s, 1H), 7.29-7.32 (m, 2H), 7.08 (m, 1H), 5.61 (s, 2H), 5.09 (s, 1H), 4.66 (s, 2H). LCMS (API-ES, M+H+): 319.1.

(b) 1-(2,4-Difluorobenzyl)-N-hydroxy-3-hydroxymethyl-N-methyl-1H-pyrrolo[2,3-c]pyridine-5-carboxamide. The title compound was prepared by coupling of 1-(2,4-difluorobenzyl)-3-hydroxymethyl-1H-pyrrolo[2,3-c]pyridine-5-carboxylic acid and N-methyl hydroxylamine hydrochloride in a manner similar to step (c) of example 1. $^1$H NMR (CD$_3$OD) δ: 8.80 (s, 1H), 8.29 (s, 1H), 7.67 (s, 1H), 7.29-7.32 (m, 1H), 6.93-7.04 (m, 2H), 5.57 (s, 2H), 4.81 (s, 2H), 3.43 (s, 3H). LCMS (APCI, M+H$^+$): 348.0. HRMS (M+H): 348.1175; cal: 348.1160 with C$_{17}$H$_{16}$F$_2$N$_3$O$_3$. HPLC: 96.15% purity.

Example 20

1-(2,4-Difluorobenzyl)-3-dimethylaminomethyl-N-hydroxy-N-methyl-1H-pyrrolo[2,3-c]pyridine-5-carboxamide

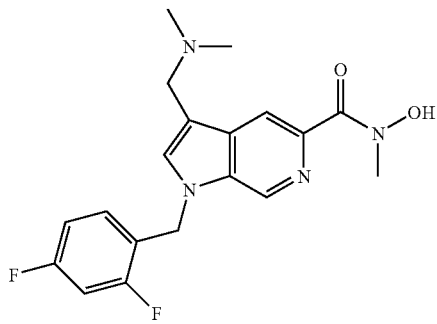

(a) 1-(2,4-Difluorobenzyl)-3-dimethylaminomethyl-1H-pyrrolo[2,3-c]pyridine-5-carboxylic acid. The title compound was prepared by hydrolysis of ethyl 1-(2,4-difluorobenzyl)-3-dimethylaminomethyl-1H-pyrrolo[2,3]-ccarboxylate in a manner similar to step (b) of example 1. $^1$H NMR (DMSO-d$_6$) δ: 8.91 (s, 1H), 8.43 (s, 1H), 7.74 (s, 1H), 7.29-7.37 (m, 2H), 7.04-7.10 (m, 1H), 5.62 (s, 2H), 3.70 (s, 2H), 2.22 (s, 6H). LCMS (API-ES, M+H$^+$): 346.3.

(b) 1-(2,4-Difluorobenzyl)-3-dimethylaminomethyl-N-hydroxy-N-methyl-1H-pyrrolo[2,3-c]pyridine-5-carboxamide. The title compound was prepared by coupling of 1-(2,4-difluorobenzyl)-3-dimethylaminomethyl-1H-pyrrol (DMSO-d$_6$)δ: 9.44 (broad s, 1H), 8.96 (s, 1H), 8.26 (s, 1H), 7.93 (s, 1H), 7.44 (m, 1H), 7.28-7.35 (m, 1H), 7.10 (m, 1H), 5.66 (s, 2H), 4.47 (s, 2H), 3.32 (s, 3H), 2.72 (s, 6H). LCMS (APCI, M+H$^+$): 375.0. HRMS calcd for C$_{19}$H$_{21}$F$_2$N$_4$O$_2$. (M+H) 375.1633, found 375.1632. HPLC: 97.62% purity.

Example 21

1-(2,4-Difluorobenzyl)-N-methoxy-1H-pyrrolo[2,3-c]pyridine-5-carboxamide

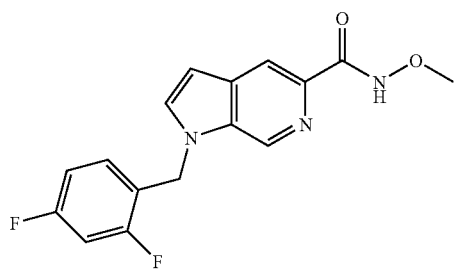

The title compound was prepared by coupling of 1-(2,4-difluorobenzyl)-1H-pyrrolo[2,3-c]pyridine-5-carboxylic acid and O-methyl hydroxylamine hydrochloride in analogy to step (c) of example 1. $^1$H NMR (CD$_3$OD) δ: 8.80 (s, 1H), 8.33 (s, 1H), 7.64 (d, 1H, J=3.0 Hz), 7.24-7.27 (m, 1H), 6.96-7.08 (m, 2H), 6.74 (d, 1H, J=3.0 Hz), 5.62 (s, 2H) 3.85

(s, 3H). LCMS (API-ES, M+H⁺): 318.0. HRMS calcd for $C_{16}H_{14}F_2N_3O_2$. (M+H) 318.1054, found 318.1045. Anal. ($C_{16}H_{13}F_2N_3O_2$) C, H, N. HPLC: 99.6% purity.

Example 22

1-(2,4-Difluorobenzyl)-3-ethoxymethyl-N-methoxy-1H-pyrrolo[2,3-c]pyridine-5-carboxamide

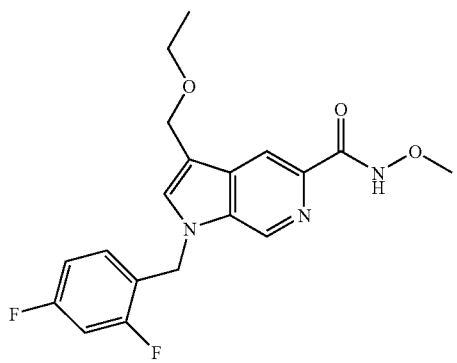

The title compound was prepared by coupling of 1-(2,4-difluoro-benzyl)-3-ethoxymethyl-1H-pyrrolo[2,3-c]pyridine-5-carboxylic acid and O-methyl hydroxylamine hydrochloride in a manner similar to step (c) of example 1. ¹H NMR (CD₃OD) δ: 8.75 (s, 1H), 8.37 (s, 1H), 7.61 (s, 1H), 7.21-7.28 (m, 1H), 6.88-7.00 (m, 2H), 5.54 (s, 2H), 4.70 (s, 2H), 3.82 (s, 3H), 3.59 (q, 2H, J=7.0 Hz), 1.20 (t, 3H, J=7.0 Hz). LCMS (APCI, M+H⁺): 376.1. HRMS calcd for $C_{19}H_{20}F_2N_3O_3$ (M+H) 376.1473, found 376.1485. HPLC: 99.24% purity.

Example 23

1-(2,4-Difluorobenzyl)-3-hydroxymethyl-N-methoxy-1H-pyrrolo[2,3-c]pyridine-5-carboxamide

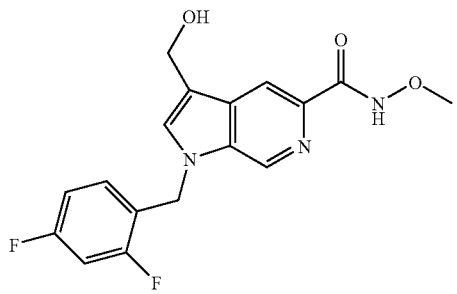

The title compound was prepared by coupling of 1-(2,4-difluoro-benzyl)-3-hydroxymethyl-1H-pyrrolo[2,3-c]pyridine-5-carboxylic acid and O-methyl hydroxylamine hydrochloride in a manner similar to step (c) of example 1. ¹H NMR (CD₃OD) δ: 8.76 (s, 1H), 8.41 (s, 1H), 7.58 (s, 1H), 7.23-7.29 (m, 1H), 6.88-7.00 (m, 2H), 5.54 (s, 2H), 4.80 (s, 2H), 3.82 (s, 3H). LCMS (APCI, M+H⁺): 348.0. HRMS calcd for $C_{17}H_6F_2N_3O_3$ (M+H) 348.1160, found 348.1148. HPLC: 100% purity.

Example 24

1-(2,4-Difluorobenzyl)-3-dimethylaminomethyl-N-methoxy-1H-pyrrolo[2,3-c]pyridine-5-carboxamide

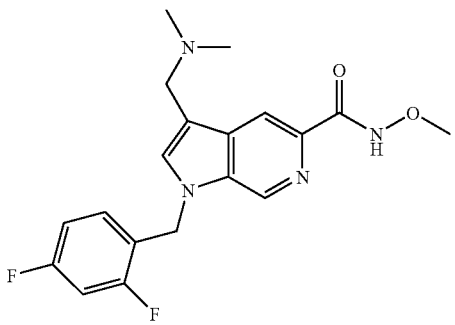

The title compound was prepared by coupling of 1-(2,4-difluoro-benzyl)-3-dimethylaminomethyl-1H-pyrrolo[2,3-c]pyridine-5-carboxylic acid and O-methyl hydroxylamine hydrochloride in a manner similar to step (c) of example 1. ¹H NMR (CD₃OD) δ; 8.90 (s, 1H), 8.50 (s, 1H), 7.89 (s, 1H), 7.41 (m, 1H), 7.00-7.07 (m, 2H), 5.64 (s, 2H), 4.52 (s, 2H), 3.82 (s, 3H), 2.85 (s, 6H). LCMS (APCI, M+H⁺): 375.0. HRMS calcd for $C_{19}H_{21}F_2N_4O_2$ (M+H) 375.1633, found 375.1644. HPLC: 100% purity.

Example 25

N-Benzyloxy-1-(2,4-difluorobenzyl)-1H-pyrrolo[2,3-c]pyridine-5-carboxamide

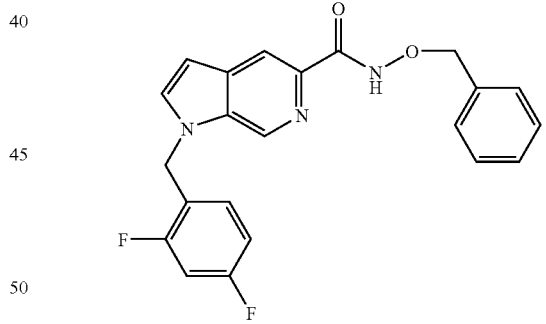

1-[3-(dimethylamino)propyl]-3-ethyl-carbodiimide hydrochloride (EDC, 126 mg, 0.67 mmol) and 1-hydroxybenzotriazole (HOBt, 56 mg, 0.56 mmol) was added to a the stirred solution of 1-(2,4-difluorobenzyl)-1H-pyrrolo[2,3-c]pyridine-5-carboxylic acid (70 mg, 0.24 mmol) in DMF (8 mL). The mixture was stirred for 1 h, and then triethylamine (0.33 ml, 2.37 mmol) and O-benzylhydroxylamine (231 mg, 1.80 mmol) were added. The resulting mixture was stirred for 24 h at ambient temperature, and then water (50 mL) was added. The precipitates were collected, and dried to give the title compound (60 mg, 63%). ¹H NMR (DMSO-d₆) δ: 11.71 (s, 1H), 8.81 (s, 1H), 8.20(s, 1H), 7.74 (s, 1H), 7.15-7.45 (m, 7H), 7.02 (m, 1H), 6.68 (s, 1H), 5.60 (s, 2H), 4.88 (s, 2H). HRMS calcd for $C_{22}H_8F_2N_3O_2$ (M+H) 394.1367, found 394.1388.

Example 26

N-Benzyloxy-3-(4-fluorobenzyl)-3H-imidazo[4,5-c]pyridine-6-carboxamide

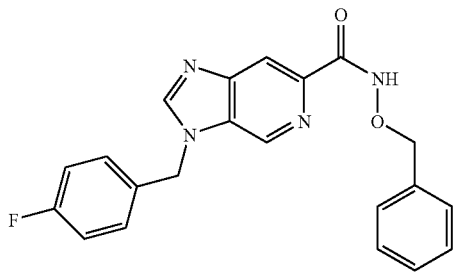

(a) Methyl 3-(4-fluorobenzyl)-3H-imidazo[4,5-c]pyridine-6-carboxylate and methyl 1-(4-fluorobenzyl)-1H-imidazo[4,5-c]pyridine-6-carboxylate. The title compounds were prepared by alkylation of methyl 1H-imidazo[4,5-c]pyridine-6-carboxylate with 4-fluorobenzyl bromide under the same conditions as those in step (a) of example 1. The two isomers were separated by column chromatography using ethyl acetate as eluent and characterized by NOESY $^1$H NMR.

Methyl 3-(4-fluorobenzyl)-3H-imidazo[4,5-c]pyridine-6-carboxylate: $^1$H NMR (300 MHz, DMSO-$d_6$) δ: 8.95 (s, 1H), 8.71 (s, 1H), 8.26 (s, 1H), 7.42-7.40 (m, 2H), 7.12-7.09 (m, 2H), 5.57 (s, 2H), 3.79 (s, 3H). LCMS (API-ES, M+H$^+$): 286.1

Methyl 1-(4-fluorobenzyl)-1H-imidazo[4,5-c]pyridine-6-carboxylate: $^1$H NMR (300 MHz, DMSO-$d_6$) δ: 8.96 (s, 1H), 8.67 (s, 1H), 8.31 (s, 1H), 7.35-7.33 (m, 2H), 7.14-7.08 (m, 2H), 5.57 (s, 2H), 3.79 (s, 3H). LCMS (API-ES, M+H$^+$): 286.1.

(b) 3-(4-Fluorobenzyl)-3H-imidazo[4,5-c]pyridine-6-carboxylic acid. Methyl 3-(4-fluorobenzyl)-3H-imidazo[4,5-c]pyridine-6-carboxylate (1.30 g, 4.56 mmol) in 30 ml 1 M LiOH in MeOH solution was stirred for 16 hours at ambient temperature. The mixture was concentrated to ⅓ of its volume in vacuo, and the pH of the concentrated solution was adjusted to 4-5 using 0.5 M hydrochloric acid. The precipitate that formed was collected by filtration and dried in vacuo to afford the title compound as a white powder (1.10 g, 88% yield). $^1$H NMR (300 MHz, MeOH-$d_4$) δ: 8.73 (s, 1H), 8.56 (s, 1H), 8.39 (s, 1H), 7.36-7.34 (m, 2H), 7.07-7.02 (m, 2H), 5.57 (s, 2H). LCMS (API-ES, M+H$^+$): 272.1.

(c) N-Benzyloxy-3-(4-fluorobenzyl)-3H-imidazo[4,5-c]pyridine-6-carboxamide. The title compound was prepared by coupling of 3-(4-fluorobenzyl)-3H-imidazo[4,5-c]pyridine-6-carboxylic acid and N-benzyloxyamine hydrochloride under the same conditions as those in step (c) of example 1. $^1$H NMR (300 MHz, MeOH-$d_4$) δ: 8.70 (s, 1H), 8.53 (s, 1H), 8.31 (s, 1H), 7.46-7.28 (m, 7H), 7.07-7.05 (m, 2H), 5.56 (s, 2H), 4.92 (s, 2H). LCMS (API-ES, M+H$^+$): 377.1. HRMS calcd for $C_{21}H_{18}FN_4O_2$ (M+H) 377.1444, found 377.1424. HPLC: >91% purity.

Example 27

3-(4-Fluorobenzyl)-N-methoxy-3H-imidazo[4,5-c]pyridine-6-carboxamide

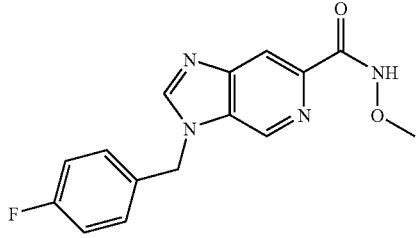

The title compound was prepared by coupling of 3-(4-fluorobenzyl)-3H-imidazo[4,5-c]pyridine-6-carboxylic acid and N-methoxyamine hydrochloride under the same conditions as those in step (c) of example 1. $^1$H NMR (300 MHz, MeOH-$d_4$) δ: 8.71 (s, 1H), 8.53 (s, 1H), 8.32 (s, 1H), 7.36-7.33 (m, 2H), 7.07-7.05 (m, 2H), 5.57 (s, 2H), 3.75 (s, 3H). LCMS (API-ES, M+H$^+$): 301.1. HRMS calcd for $C_{15}H_{14}FN_4O_2$ (M+H) 301.1101, found 301.1105. HPLC: >84% purity.

Example 28

3-(4-Fluorobenzyl)-N-phenoxy-3H-imidazo[4,5-c]pyridine-6-carboxamide

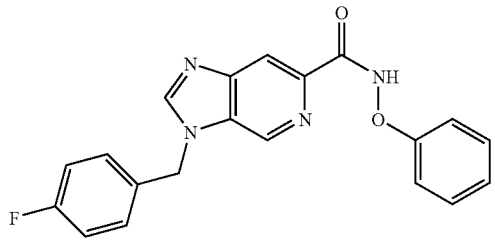

The title compound was prepared by coupling of 3-(4-fluoro-benzyl)-3H-imidazo[4,5-c]pyridine-6-carboxylic acid and N-phenoxyamine hydrochloride under the same conditions as those in step (c) of example 1. $^1$H NMR (300 MHz, MeOH-$d_4$) δ: 8.82 (s, 1H), 8.53 (s, 1H), 8.43 (s, 1H), 8.24 (d, 2H, J=7.9 Hz), 7.38-7.33 (m, 2H), 7.07-7.01 (m, 2H), 6.88-6.74 (m, 3H), 5.57 (s, 2H). LCMS (API-ES, M+H$^+$): 363.1. HRMS calcd for $C_{20}H_6FN_4O_2$ (M+H) 363.1257, found 363.1256. HPLC: >85% purity.

Example 29

3-(4-Fluorobenzyl)-N-[(pentafluorobenzyl)oxy]-3H-imidazo[4,5-c]pyridine-6-carboxamide

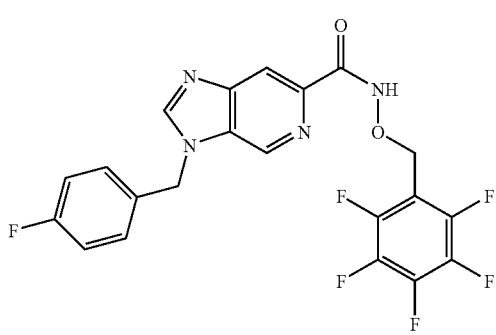

The title compound was prepared by coupling of 3-(4-fluorobenzyl)-3H-imidazo[4,5-c]pyridine-6-carboxylic acid and N-[(2,3,4,5,6-pentafluorobenzyl)oxy]amine hydrochloride under the same conditions as those in step (c) of example 1. $^1$H NMR (300 MHz, MeOH-$d_4$) δ: 8.69 (s, 1H), 8.52 (s, 1H), 8.28 (s, 1H), 7.33-7.32 (m, 2H), 7.07-7.02 (m, 2H), 5.56 (s, 2H), 5.09 (s, 2H). LCMS (API-ES, M+H$^+$): 467.0. HRMS calcd for $C_{21}H_{13}F_6N_4O_2$ (M+H) 467.0943, found 467.0942. HPLC: >80% purity.

Example 30

N-(Allyloxy)-3-(4-fluorobenzyl)-3H-imidazo[4,5-c]pyridine-6-carboxamide

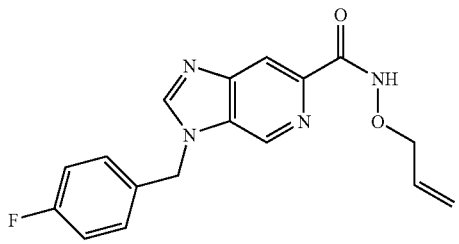

The title compound was prepared by coupling of 3-(4-fluorobenzyl)-3H-imidazo[4,5-c]pyridine-6-carboxylic acid and N-allyloxyamine hydrochloride under the same conditions as those in step (c) of example 1. $^1$H NMR (300 MHz, MeOH-$d_4$) δ: 8.71 (s, 1H), 8.53 (s, 1H), 8.31 (s, 1H), 7.40-7.33 (m, 2H), 7.09-7.01 (m, 2H), 6.01-5.99 (m, 1H), 5.57 (s, 2H), 5.40-5.20 (m, 2H), 4.41 (d, 2H, J=6.0 Hz). LCMS (API-ES, M+H$^+$): 327.0.1. HRMS calcd for $C_{17}H_{16}FN_4O_2$ (M+H) 327.1257, found 327.1248. HPLC: 100% purity.

Example 31

6-(2,4-Difluorobenzyl)-2-hydroxy-1,6-dihydrodipyrrolo[3,2-d:3',4'-b]pyridin-3(2H)-one

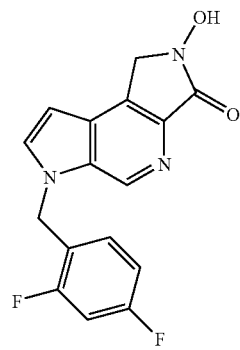

(a) Methyl 1-{[4-(benzyloxy)amino]methyl)}-1-phenylsulfonyl-1H-pyrrolo[2,3-c]pyridine-5-carboxylate. To a stirred solution of methyl 4-bromomethyl-1-phenylsulfonyl-1H-pyrrolo[2,3-c]pyridine-5-carboxylate (0.30 g, 0.73 mmol) [prepared acc. X. Doisy et al., *Bioorg. Med. Chem.* 1999, 7, 921-932]in DMF (20 mL) were added benzyloxyamine (0.45 g, 3.65 mmol) and triethylamine (0.51 mL, 3.65 mmol). The resulting mixture was stirred for 16 hours at ambient temperature. It was quenched with water (30 mL), and extracted with ethyl acetate (3×30 mL). The combined organic extracts were washed with water (2×30 mL), dried over sodium sulfate, concentrated in vacuo and purified by flash chromatography. Elution with hexane:ethyl acetate (1:1) provided the title compound as a solid (0.11 g, 33% yield).1H NMR (CD$_3$OD) δ: 9.14 (s, 1H), 8.04 (d, 2H, J=8.3 Hz), 7.98 (d, 1H, J=3.0 Hz), 7.53-7.68 (m, 3H), 7.34 (d, 2H, J=4.3 Hz), 7.13-7.15 (m, 2H), 7.05-7.07 (m, 2H), 6.98 (d, 1H, J=3.0 Hz), 4.47 (s, 2H), 4.46 (s, 2H), 3.90 (s, 3H). LCMS (API-ES, M+H$^+$): 452.1.

(b) 2-Benzyloxy-1,6-dihydrodipyrrolo[3,2-d:3',4'-b]pyridin-3(2H)-one. To a stirred solution of methyl 1-{[4-(benzyloxy)amino]methyl)}-1-phenylsulfonyl-1H-pyrrolo[2,3-c]pyridine-5-carboxylate (0.11 g, 0.24 mmol) in anhydrous methanol (10 mL) was added sodium ethoxide (0.18 mL, 21 wt % in ethanol, 0.48 mmol). The resulting mixture was stirred for 2 hours at ambient temperature. It was neutralized with excess acetic acid (0.1 mL). On addition of water, the product precipitated out. It was collected by filtration, washed with water and hexane, and dried in vacuo to give a light yellow solid (0.062 g, 91% yield). $^1$H NMR (DMSO-$d_6$) δ: 12.16 (s, 1H), 8.86 (s, 1H), 7.80 (d, 1H, J=2.6 Hz), 7.52 (d, 2H, J=6.3 Hz), 7.40-7.42 (m, 3H), 6.67 (s, 1H), 5.13 (s, 2H), 4.75 (s, 2H). LCMS (API-ES, M+H$^+$): 280.1.

(c) 2-Benzyloxy-6-(2,4-difluoro-benzyl)-1,6-dihydrodipyrrolo[3,2-d:3',4'-b]pyridin-3(2H)-one. The title compound was prepared by alkylation of 2-benzyloxy-1,6-dihydrodipyrrolo[3,2-d:3',4'-b]pyridin-3(2H)-one with 2,4-difluorobenzyl bromide in a manner similar to step (a) of example 1. $^1$H NMR (CD$_3$OD) δ: 8.91 (s, 1H), 7.75 (d, 1H, J=3.0 Hz), 7.51-7.54 (m, 2H), 7.38-7.40 (m, 3H), 7.27-7.29 (m, 1H), 7.02-7.05 (m, 1H), 6.93-7.01 (m, 1H), 6.71 (d, 1H, J=3.0 Hz), 5.64 (s, 2H), 5.18 (s, 2H), 4.65 (s, 2H). LCMS (API-ES, M+H$^+$): 406.1.

(d) 6-(2,4-Difluorobenzyl)-2-hydroxy-1,6-dihydrodipyrrolo[3,2-d:3',4'-b]pyridin-3(2H)-one. To a stirred solution of 2-benzyloxy-6-(2,4-difluorobenzyl)-1,6-dihydrodipyrrolo[3,2-d:3',4'-b]pyridin-3(2H)-one (0.050 g, 0.12 mmol) in anhydrous ethanol (15 mL) was added palladium hydroxide (5 mg, 20 wt % on carbon). The solution was stirred under a hydrogen atmosphere for 16 h. The catalyst was filtered off and the solution was concentrated until a product precipitated. The product was collected by filtration, washed with water and hexane. Repeated recrystallization from methanol provided the title compound as a light yellow solid (0.002 g, 5.1% yield). $^1$H NMR (CD$_3$OD) δ: 8.90 (s, 1H), 7.76 (d, 1H, J=3.0 Hz), 7.25-7.29 (m, 1H), 6.99-7.02 (m, 1H), 6.93 (m, 1H), 6.77 (d, 1H, J=3.0 Hz), 5.64 (s, 2H), 5.18 (s, 2H), 4.60 (s, 2H). LCMS (API-ES, M+H$^+$): 316.0. HRMS calcd for C$_{16}$H$_{12}$F$_2$N$_3$O$_2$ (M+H) 316.0898, found 316.0897. HPLC: 100% purity.

Example 32

3-(2,3-Difluorobenzyl)-N-phenoxy-3H-imidazo[4,5-c]pyridine-6-carboxamide

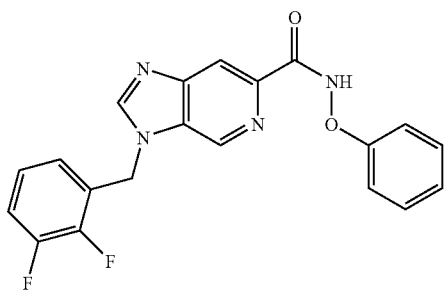

The title compound can be prepared by coupling of 3-(2,3-difluorobenzyl)-3H-imidazo[4,5-c]pyridine-6-carboxylic acid and N-phenoxyamine under the same conditions as those in step (c) of example 1.

Example 33

3-(2,3-Difluorobenzyl)-N-methoxy-3H-imidazo[4,5-c]pyridine-6-carboxamide

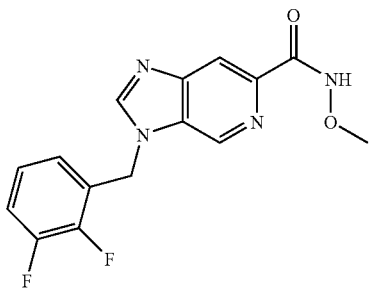

The title compound can be prepared by coupling of 3-(2,3-difluorobenzyl)-3H-imidazo[4,5-c]pyridine-6-carboxylic acid and N-methoxyamine under the same conditions as those in step (c) of example 1.

Example 34

N-Allyloxy-3-(2,3-difluorobenzyl)-3H-imidazo[4,5-c]pyridine-6-carboxamide

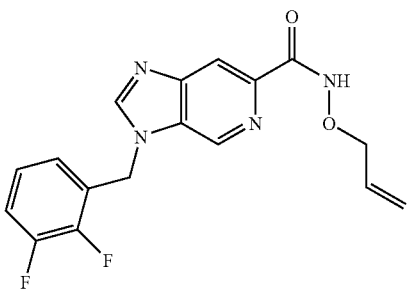

The title compound can be prepared by coupling of 3-(2,3-difluorobenzyl)-3H-imidazo[4,5-c]pyridine-6-carboxylic acid and N-allyloxyamine under the same conditions as those in step (c) of example 1.

Example 35

1-(4-Fluorobenzyl)-N-phenoxy-1H-imidazo[4,5-c]pyridine-6-carboxamide

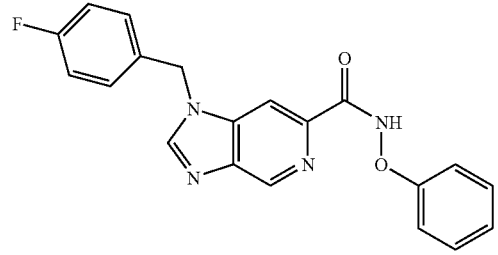

The title compound can be prepared from 1-(4-fluorobenzyl)-1H-imidazo[4,5-c]pyridine-6-carboxylic acid and N-phenoxyamine under the same conditions as those in step (c) of Example 1.

Example 36

N-tert-Butoxy-3-(2,3-difluorobenzyl)-3H-imidazo[4,5-c]pyridine-6-carboxamide

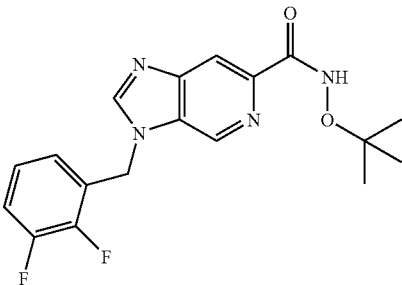

The title compound can be prepared by coupling of 3-(2,3-difluorobenzyl)-3H-imidazo[4,5-c]pyridine-6-carboxylic acid and N-(tert-butoxy)amine under the same conditions as those in step (c) of Example 1.

Example 37

N-Methoxy-3-(3-methyl-butyl)-3H-imidazo[4,5-c]
pyridine-6-carboxamide

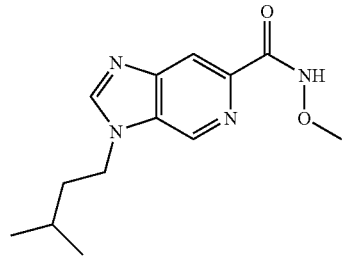

The title compound can be prepared by coupling of 3-(3-methyl-butyl)-3H-imidazo[4,5-c]pyridine-6-carboxylic acid [prepared by alkylation of methyl 1H-imidazo[4,5-c]pyridine-6-carboxylate with 1-bromo-3-methyl-butane in a manner similar to step (d) of example 16] and N-methoxyamine under the same conditions as those in step (c) of Example 1.

Example 38

3-(3-Methyl-butyl)-N-phenoxy-3H-imidazo[4,5-c]
pyridine-6-carboxamide

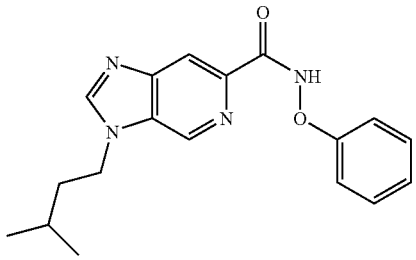

The title compound can be prepared by coupling of 3-(3-methyl-butyl)-3H-imidazo[4,5-c]pyridine-6-carboxylic acid (prepared by alkylation of methyl 1H-imidazo[4,5-c]pyridine-6-carboxylic with 1-bromo-3-methyl-butane in a manner similar to step (d) of example 16) and N-phenoxyamine under the same conditions as those in step (c) of Example 1.

Example 39

3-(2-Cyclohexyl-ethyl)-N-phenoxy-3H-imidazo[4,5-c]pyridine-6-carboxamide

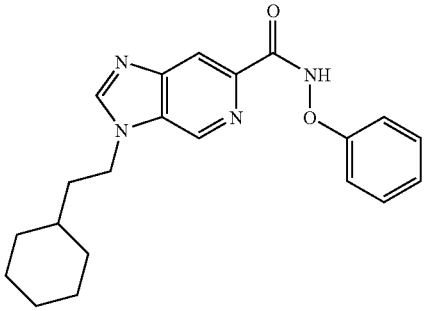

The title compound can be prepared by coupling of 3-(2-cyclohexyl-ethyl)-3H-imidazo[4,5-c]pyridine-6-carboxylic acid (prepared by alkylation of methyl 1H-imidazo[4,5-c]pyridine-6-carboxylate with 1-bromo-3-cyclohexyl ethane in a manner similar to step (d) of example 16) and N-phenoxyamine under the same conditions as those in step (c) of Example 1.

Example 40

3-(2-Cyclohexyl-ethyl)-N-methoxy-3H-imidazo[4,5-c]pyridine-6-carboxamide

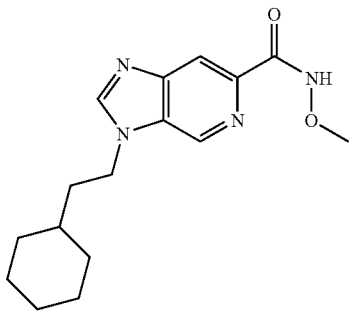

The title compound can be prepared by coupling of 3-(2-cyclohexyl-ethyl)-3H-imidazo[4,5-c]pyridine-6-carboxylic acid (prepared by alkylation of methyl 1H-imidazo[4,5-c]pyridine-6-carboxylate with 1-bromo-3-cyclohexyl ethane in a manner similar to step (d) of example 16) and N-methoxyamine under the same conditions as those in step (c) of Example 1.

Example 41

N-Allyloxy-3-(2-cyclohexyl-ethyl)-3H-imidazo[4,5-c]pyridine-6-carboxamide

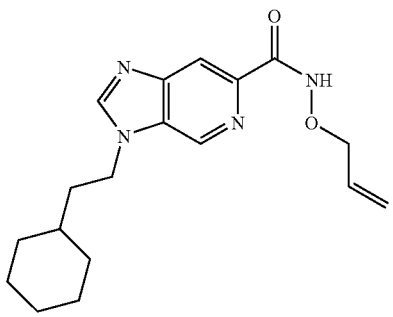

The title compound can be prepared by coupling of 3-(2-cyclohexyl-ethyl)-3H-imidazo[4,5-c]pyridine-6-carboxylic acid (prepared by alkylation of methyl 1H-imidazo[4,5-c]pyridine-6-carboxylate with 1-bromo-3-cyclohexyl ethane in a manner similar to step (d) of example 16) and N-allyloxyamine under the same conditions as those in step (c) of Example 1.

Example 42

1-(2,4-Difluorobenzyl)-N-hydroxy-4-methoxymethyl-1H-pyrrolo[2,3-c]pyridine-5-carboxamide

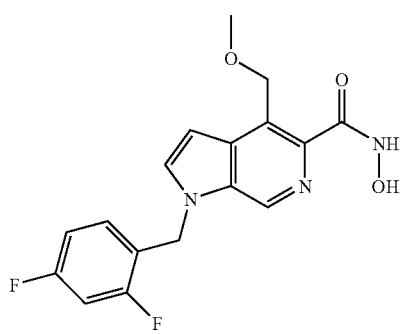

The title compound can be prepared from methyl 4-methoxymethyl-1H-pyrrolo[2,3-c]pyridine-5-carboxylate (prepared according to X. Doisy et al., *Bioorg. Med. Chem.* 1999, 7, 921-932) and 2,4-difluorobenzyl bromide following the steps as described in Example 1.

Example 43

1-(2,4-Difluorobenzyl)-N-hydroxy-3-(2-phenylvinyl)-1H-pyrrolo[2,3-c]pyridine-5-carboxamide

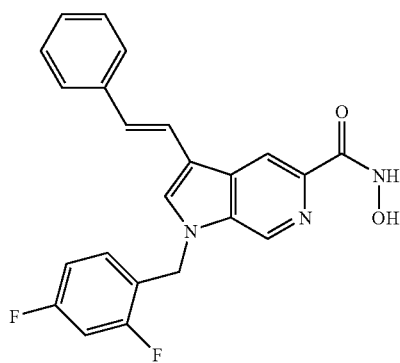

The title compound can be prepared from ethyl 3-(2-phenylvinyl)-1H-pyrrolo[2,3-c]pyridine-5-carboxylate (prepared according to X. Doisy et al., *Bioorg. Med. Chem.* 1999, 7, 921-932) and 2,4-difluoro-benzyl bromide following the steps as described in Example 1.

Example 44

1-(2,4-difluorobenzyl)-N-hydroxy-3-(3-phenylprop-1-enyl)-1H-pyrrolo[2,3-c]pyridine-5-carboxamide

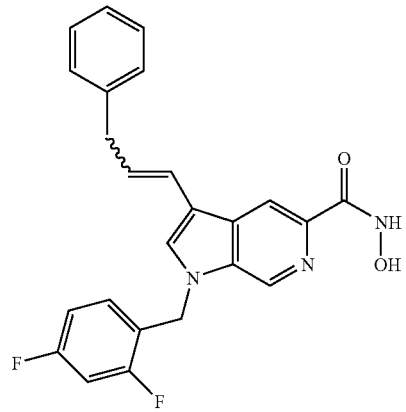

The title compound can be prepared from ethyl 3-(3-phenylprop-1-enyl)-1H-pyrrolo[2,3-c]pyridine-5-carboxylate (prepared according to X. Doisy et al., *Bioorg. Med. Chem.* 1999, 7, 921-932) and 2,4-difluoro-benzyl bromide following the steps as described in Example 1.

Example 45

1-(2,4-difluorobenzyl)-N-hydroxy-3-(2-phenylethyl)-1H-pyrrolo[2,3-c]pyridine-5-carboxamide

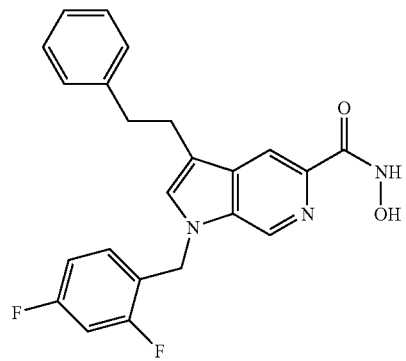

The title compound can be prepared from ethyl 3-(2-phenylethyl)-1H-pyrrolo[2,3-c]pyridine-5-carboxylate (prepared according to X. Doisy et al., *Bioorg. Med. Chem.* 1999, 7, 921-932) and 2,4-difluorobenzyl bromide following the steps as described in Example 1.

Example 46

1-(2,4-difluorobenzyl)-N-hydroxy-3-(3-phenylpropyl)-1H-pyrrolo[2,3-c]pyridine-5-carboxamide

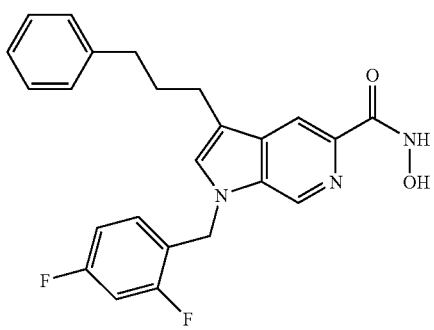

The title compound can be prepared from ethyl 3-(3-phenyl-propyl)-1H-pyrrolo[2,3-c]pyridine-5-carboxylate (prepared according to X. Doisy et al., *Bioorg. Med. Chem.* 1999, 7, 921-932) and 2,4-difluorobenzyl bromide following the steps as described in Example 1.

Example 47

1-(2,4-Difluorobenzyl)-N-hydroxy-3-{[(2-phenylethyl)oxy]methyl}-1H-pyrrolo[2,3-c]pyridine-5-carboxamide

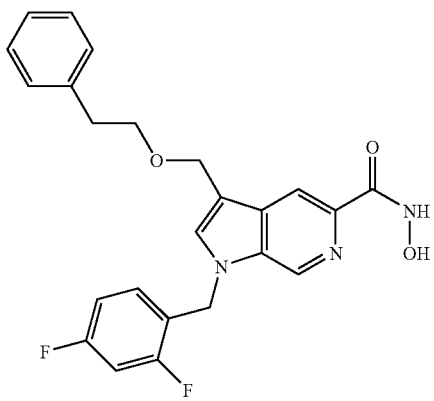

The title compound can be prepared from ethyl 3-[(2-phenylethoxy)methyl]-1H-pyrrolo[2,3-c]pyridine-5-carboxylate (prepared according to X. Doisy et al., *Bioorg. Med. Chem.* 1999, 7, 921-932) and 2,4-difluorobenzyl bromide following the steps as described in Example 1.

Example 48

1-(2,4-Difluorobenzyl)-N-hydroxy-3-{[(3-phenylallyl)oxy]methyl}-1H-pyrrolo[2,3-c]pyridine-5-carboxamide

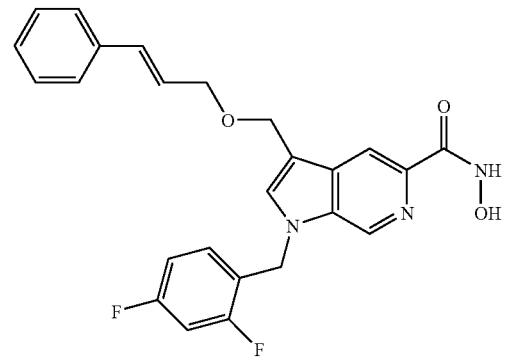

The title compound can be prepared from ethyl 3-{[(3-phenylallyl)oxy]methyl}-1H-pyrrolo[2,3-c]pyridine-5-carboxylate (prepared according to X. Doisy et al., *Bioorg. Med. Chem.* 1999, 7, 921-932) and 2,4-difluorobenzyl bromide following the steps as described in Example 1.

Example 49

1-(2,4-Difluorobenzyl)-N-hydroxy-3-methyl-1H-pyrrolo[2,3-c]pyridine-5-carboxamide

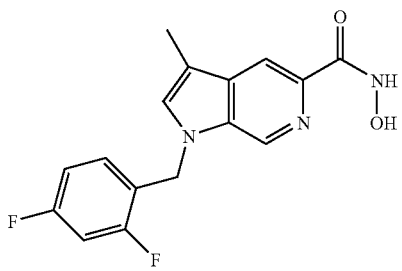

The title compound can be prepared from ethyl 3-methyl-1H-pyrrolo[2,3-c]pyridine-5-carboxylate (prepared according to S. K. Singh et al., *Heterocycles,* 1997, 44, 379-391) and 2,4-difluorobenzyl bromide following the steps as described in Example 1.

Example 50

1-(2,4-Difluorobenzyl)-3-ethyl-N-hydroxy-1H-pyrrolo[2,3-c]pyridine-5-carboxamide

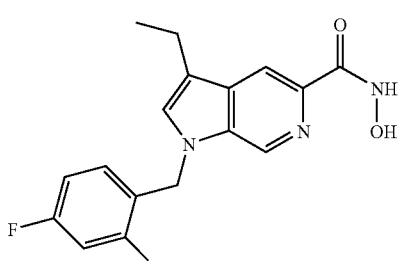

The title compound can be prepared from ethyl 3-ethyl-1H-pyrrolo[2,3-c]pyridine-5-carboxylate (prepared according to S. K. Singh et al., *Heterocycles*, 1997, 44, 379-391) and 2,4-difluorobenzyl bromide following the steps as described in Example 1.

Example 51

3-Allyl-1-(2,4-difluorobenzyl)-N-hydroxy-1H-pyrrolo[2,3-c]pyridine-5-carboxamide

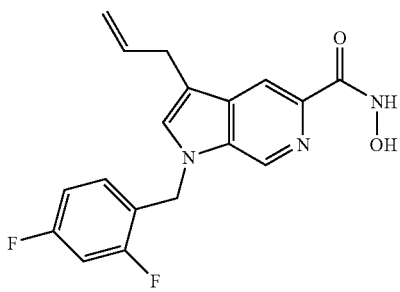

The title compound can be prepared from ethyl 3-allyl-1H-pyrrolo[2,3-c]pyridine-5-carboxylate (prepared according to S. K. Singh et al., *Heterocycles*, 1997, 44, 379-391) and 2,4-difluorobenzyl bromide following the steps as described in Example 1.

Example 52

1-(2,4-Difluorobenzyl)-N-hydroxy-7-methyl-1H-pyrrolo[2,3-c]pyridine-5-carboxamide

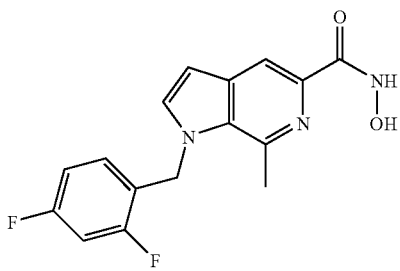

The title compound can be prepared from ethyl 7-methyl-1H-pyrrolo[2,3-c]pyridine-5-carboxylate (prepared according to J.-F. Rousseau, R. H. Dodd, *J. Org. Chem.* 1998, 63, 2731-2737) and 2,4-difluorobenzyl bromide following the steps as described in Example 1.

Example 53

Ethyl 1-(2,4-Difluorobenzyl)-5-hydroxycarbamoyl-1H-pyrrolo[2,3-c]pyridine-2-carboxylate

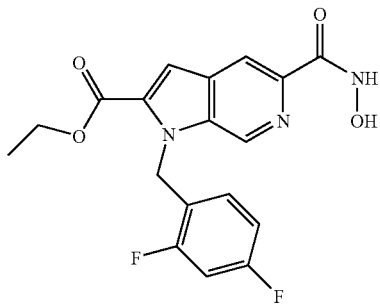

(a) Ethyl 1-(2,4-difluorobenzyl)-5-formyl-1H-pyrrolo[2,3-c]pyridine-2-carboxyl ate. The title compound can be prepared by alkylation of ethyl 5-formyl-1H-pyrrolo[2,3-c]pyridine-2-carboxylate (prepared according to J.-F. Rousseau, R. H. Dodd, X. Doisy, P. Potier, *Heterocycles* 1989, 28, 1101-1113) and 2,4-difluorobenzyl bromide in a manner similar to step (a) in Example 1.

(b) 1-(2,4-Difluorobenzyl)-(2-ethoxycarbonyl)-1H-pyrrolo[2,3-c]pyridine-5-carboxylic acid. The title compound can be prepared by oxidation of ethyl 1-(2,4-difluoro-benzyl)-5-formyl-1H-pyrrolo[2,3-c]pyridine-2-carboxylate according to the procedure by R. H. Dodd, M. Le Hyaric, *Synthesis* 1993, 295-287.

(c) Ethyl 1-(2,4-Difluorobenzyl)-5-hydroxycarbamoyl-1H-pyrrolo[2,3-c]pyridine-2-carboxylate. The title compound can be prepared from 1-(2,4-difluorobenzyl)-(2-ethoxycarbonyl)-1H-pyrrolo[2,3-c]pyridine-5-carboxylic acid following in a manner similar to step (c) in Example 1.

Example 54

3-(2,4-Difluoro-phenoxymethyl)-1-ethyl-N-hydroxy-1H-pyrrolo[3,2-c]pyridine-6-carboxamide

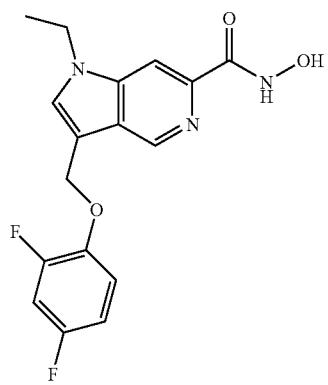

(a) Ethyl 1-ethyl-1H-pyrrolo[3,2-c]pyridine-6-carboxylate. A solution of 1-ethylpyrrole (1.20 g, 12.62 mmol), ethyl 3-dimethylamino-2-(dimethylamino-methyleneamino)-acrylate (3.2 g, 15.15 mmol) (prepared according to W.

Kantlehner, F. Wagner, H. Bredereck, *Liebigs Ann. Chem.* 1980, 344-357) and trifluoroacetic acid (4.0 mL, 50.48 mmol) in acetic acid (20 mL) was stirred for 16 h at ambient temperature. Then the solution was heated in a SmithCreator™ (microwave reactor from Personal Chemistry) to 180° C. for 2 minutes. The reaction solution was poured into satd. potassium carbonate solution (600 mL), extracted with ethyl acetate (3×300 mL). The combined organic extracts were washed with brine (2×200 mL), dried over sodium sulfate, and concentrated. Purification by column chromatograph with ethyl acetate provided the title compound. (1.90 g, 70% yield). $^1$H NMR (CD$_3$OD) δ: 8.85 (s, 1H), 8.30 (s, 1H), 7.61 (d, 1H, J=3.0 Hz), 6.76 (d, 1H, J=3.0 Hz), 4.30-4.48 (m, 4H), 1.41-1.50 (m, 6H). LCMS (API-ES, M+H$^+$): 219.1.

(b) Ethyl 3-dimethylaminomethyl-1-ethyl-1H-pyrrolo[3,2-c]pyridine-6-carboxylate. The title compound was prepared from ethyl 1-ethyl-1H-pyrrolo[3,2-c]pyridine-6-carboxylate and N,N-dimethylmethylene ammonium iodide in a manner similar to step (a) of Example 12. $^1$H NMR (DMSO-d$_6$) δ: 8.95 (s, 1H), 8.22 (s, 1H), 7.63 (s, 1H), 4.27-4.38 (m, 4H), 3.61 (s, 2H), 2.17 (s, 6H), 1.33-1.40 (m, 6H). MS (API-ES, M+H$^+$): 276.0.

(c) Ethyl 3-acetoxymethyl-1-ethyl-1H-pyrrolo[3,2-c]pyridine-6-carboxylate. The title compound was prepared from ethyl 3-dimethylaminomethyl-1-ethyl-1H-pyrrolo[3,2-c]pyridine-6-carboxylate in a manner similar to step (b) of Example 12. $^1$H NMR (CD$_3$OD) δ: 8.96 (s, 1H), 8.29 (s, 1H), 7.70 (s, 1H), 5.37 (s, 2H), 4.45 (q, 2H, J=7 Hz), 4.33 (q, 2H, J=7 Hz), 2.03 (s, 3H), 1.33-1.40 (m, 6H). MS (API-ES, M+H$^+$): 291.0.

(d) Ethyl 3-hydroxymethyl-1-ethyl-1H-pyrrolo[3,2-c]pyridine-6-carboxylate. The title compound was prepared from ethyl 3-acetoxymethyl-1-ethyl-1H-pyrrolo[3,2-c]pyridine-6-carboxylate in a manner similar to step (b) of Example 12. $^1$H NMR (CD$_3$OD) δ: 8.97 (s, 1H), 8.28 (s, 1H), 7.58 (s, 1H), 4.85 (s, 2H), 4.45 (q, 2H, J=7 Hz), 4.32 (q, 2H, J=7 Hz), 1.33-1.40 (m, 6H). MS (API-ES, M+H$^+$): 249.2.

(e) Ethyl 3-(2,4-difluoro-phenoxymethyl)-1-ethyl-1H-pyrrolo[3,2-c]pyridine-6-carboxylate and ethyl 3-(3,5-difluoro-2-hydroxy-benzyl)-1-ethyl-1H-pyrrolo[3,2-c]pyridine-6-carboxylate. A solution of ethyl 3-hydroxymethyl-1-ethyl-1H-pyrrolo[3,2-c]pyridine-6-carboxylate (0.31 g, 1.25 mmol), 2,4-difluorophenol (0.12 mL, 1.25 mmol), diisopropylazodicarboxylate (0.25 mL, 1.25 mmol) and triphenylphosphine (0.33 g, 1.25 mmol) in THF (10 mL) was stirred for 16 h at ambient temperature. The reaction mixture was concentrated and purified by chromatograph to provide the title compounds as a mixture that was used without further purification in the next step. (0.25 g, 55% yield ). LCMS (API-ES, M+H$^+$): 361.1.

(f) 3-(2,4-Difluoro-phenoxymethyl)-1-ethyl-N-hydroxy-1H-pyrrolo[3,2-c]pyridine-6-carboxamide. The title compound was prepared from the mixture of ethyl 3-(2,4-difluoro-phenoxymethyl)-1-ethyl-1H-pyrrolo[3,2-c]pyridine-6-carboxylate and ethyl 3-(3,5-difluoro-2-hydroxy-benzyl)-1-ethyl-1H-pyrrolo[3,2-c]pyridine-6-carboxylate in a manner similar to step (e) of example 11. Purification by HPLC provided the pure title compound. $^1$H NMR (DMSO-d$_6$) δ: 11.18 (s, 1H), 8.87 (s, 1H), 8.78 (s, 1H), 8.06 (s, 1H), 7.71 (s, 1H), 7.29-7.31 (m, 1H), 7.14-7.18 (m, 1H), 6.93 (m, 1H), 5.31 (s, 2H), 4.24 (q, 2H, J=7.0 Hz), 1.28 (t, 3H, J=7.0 Hz). MS (API-ES, M+H$^+$): 348.0. HRMS calcd for C$_{17}$H$_{16}$F$_2$N$_3$O$_3$ (M+H) 348.1160, found 348.1164. HPLC: 100% purity.

Example 55

3-(3,5-Difluoro-2-hydroxybenzyl)-1-ethyl-N-hydroxy-1H-pyrrolo[3,2-c]pyridine-6-carboxamide

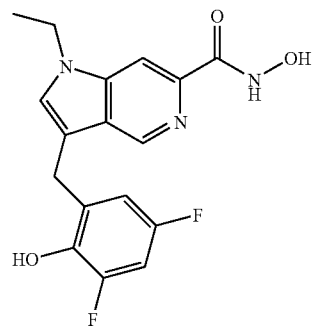

The title compound was prepared following the steps (a)-(f) in Example 55. The title compound was prepared from the mixture of ethyl 3-(2,4-difluoro-phenoxymethyl)-1-ethyl-1H-pyrrolo[3,2-c]pyridine-6-carboxylate and ethyl 3-(3,5-difluoro-2-hydroxy-benzyl)-1-ethyl-1H-pyrrolo[3,2-c]pyridine-6-carboxylate in a manner similar to step (e) of example 11. Purification by HPLC provided the pure title compound. $^1$H NMR (DMSO-d$_6$) δ: 11.19 (s, 1H), 9.60 (s, 1H), 8.94 (s, 1H), 8.75 (s, 1H), 8.07 (s, 1H), 7.45 (s, 1H), 7.03-7.04 (m, 1H), 6.83-6.86 (m, 1H), 4.30 (q, 2H, J=7.0 Hz), 4.10 (s, 2H), 1.34 (t, 3H, J=7.0 Hz). MS (API-ES, M+H$^+$): 348.0. HRMS calcd for C$_{17}$H$_{16}$F$_2$N$_3$O$_3$ (M+H) 348.1160, found 348.1162. HPLC: 95% purity.

Example 56

3-(2-Chloro-4-fluoro-phenoxymethyl)-1-ethyl-N-hydroxy-1H-pyrrolo[3,2-c]pyridine-6-carboxamide

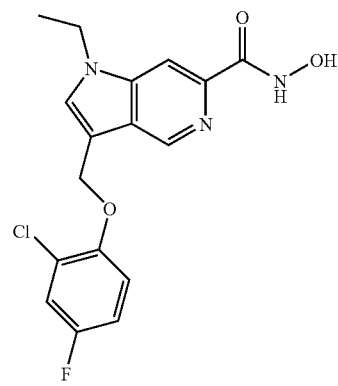

(a) Ethyl 3-(2-chloro-4-fluoro-phenoxymethyl)-1-ethyl-1H-pyrrolo[3,2-c]pyridine-6-carboxylate and ethyl 3-(3-chloro-5-fluoro-2-hydroxy-benzyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 2-chloro-4-fluorophenol using methods similar to step (e) of Example 54.

(b) 3-(2-Chloro-4-fluoro-phenoxymethyl)-1-ethyl-N-hydroxy-1H-pyrrolo[3,2-c]pyridine-6-carboxamide. The title compound can be prepared from a mixture of ethyl 3-(2-chloro-4-fluoro-phenoxymethyl)-1-ethyl-1H-pyrrolo[3,2-c]

pyridine-6-carboxylate and ethyl 3-(3-chloro-5-fluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 57

3-(3-Chloro-5-fluoro-2-hydroxybenzyl)-1-ethyl-N-hydroxy-1H-pyrrolo[3,2-c]pyridine-6-carboxamide

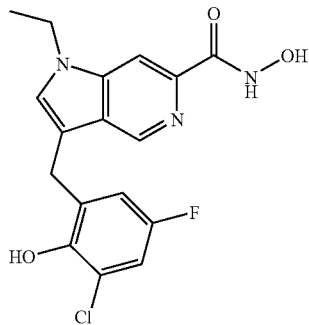

(a) Ethyl 3-(3-chloro-5-fluoro-2-hydroxybenzyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 2-chloro-4-fluorophenol using methods similar to that set forth in Example 55.

(b) 3-(3-Chloro-5-fluoro-2-hydroxybenzyl)-1-ethyl-N-hydroxy-1H-pyrrolo[3,2-c]pyridine-6-carboxamide. The title compound can be prepared from the mixture of ethyl 3-(2-chloro-4-fluoro-phenoxymethyl)-1-ethyl-1H-pyrrolo[3,2-c]pyridine-6-carboxylate and ethyl 3-(3-chloro-5-fluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 58

3-(4-Fluoro-phenoxymethyl)-1-ethyl-N-hydroxy-1H-pyrrolo[3,2-c]pyridine-6-carboxamide

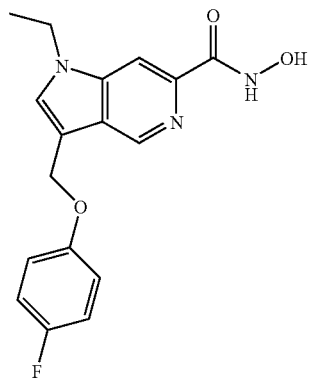

(a) Ethyl 3-(4-fluoro-phenoxymethyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 4-fluorophenol using a methods similar to step (e) of Example 54.

(b) 3-(4-Fluoro-phenoxymethyl)-1-ethyl-N-hydroxy-1H-pyrrolo[3,2-c]pyridine-6-carboxamide. The title compound can be prepared from the mixture of ethyl 3-(4-fluoro-phenoxymethyl)-1-ethyl-1H-pyrrolo[3,2-c]pyridine-6-carboxylate and ethyl 3-(5-fluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 59

3-(5-Fluoro-2-hydroxybenzyl)-1-ethyl-N-hydroxy-1H-pyrrolo[3,2-c]pyridine-6-carboxamide

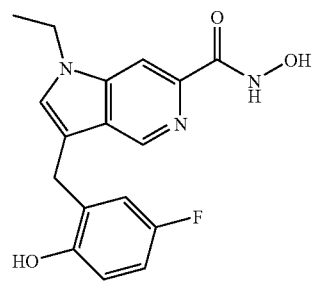

(a) Ethyl 3-(5-fluoro-2-hydroxybenzyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 4-fluorophenol using methods similar to that set forth in Example 55.

(b) 3-(5-Fluoro-2-hydroxybenzyl)-1-ethyl-N-hydroxy-1H-pyrrolo[3,2-c]pyridine-6-carboxamide. The title compound can be prepared from the mixture of ethyl 3-(4-fluoro-phenoxymethyl)-1-ethyl-1H-pyrrolo[3,2-c]pyridine-6-carboxylate and ethyl 3-(5-fluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 60

1-Ethyl-N-hydroxy-3-(2,3,4-trifluoro-2-phenoxymethyl)-1H-pyrrolo[3,2-c]pyridine-6-carboxamide

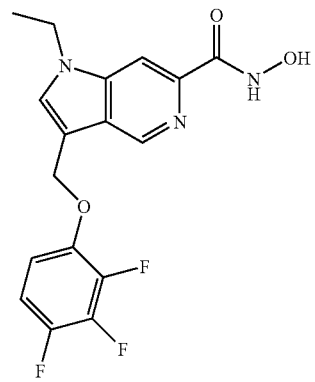

(a) Ethyl 3-(2,3,4-trifluoro-phenoxymethyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 2,3,4-trifluorophenol using methods similar to step (e) of Example 54.

(b) 1-Ethyl-N-hydroxy 3-(2,3,4-trifluoro-2-phenoxymethyl)-1H-pyrrolo[3,2-c]pyridine-6-carboxamide. The title compounds can be prepared from the mixture of ethyl 3-(3,3,4-trifluoro-phenoxymethyl)-1-ethyl-1H-pyrrolo[3,2-c]pyridine-6-carboxylate and ethyl 3-(3,4,5-trifluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 61

1-Ethyl-N-hydroxy 3-(3,4,5-trifluoro-2-hydroxybenzyl)-1H-pyrrolo[3,2-c]pyridine-6-carboxamide

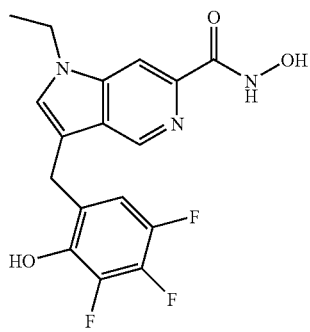

(a) Ethyl 3-(3,4,5-trifluoro-2-hydroxybenzyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 2,3,4-trifluorophenol using a methods similar to that set forth in Example 55.

(b) 1-Ethyl-N-hydroxy 3-(3,4,5-trifluoro-2-hydroxybenzyl)-1H-pyrrolo[3,2-c]pyridine-6-carboxamide. The title compound can be prepared from a mixture of ethyl 3-(3,3,4-trifluoro-phenoxymethyl)-1-ethyl-1H-pyrrolo[3,2-c]pyridine-6-carboxylate and ethyl 3-(3,4,5-trifluoro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 62

3-(2-Chloro-phenoxymethyl)-1-ethyl-N-hydroxy-1H-pyrrolo[3,2-c]pyridine-6-carboxamide

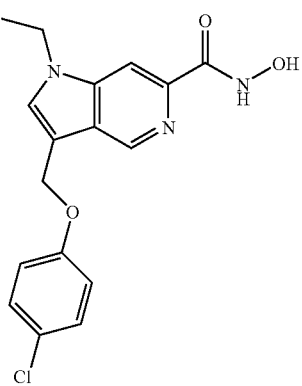

(a) Ethyl 3-(2-chloro-phenoxymethyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 4-chlorophenol using methods similar to step (e) of Example 54.

(b) 3-(2-Chloro-phenoxymethyl)-1-ethyl-N-hydroxy-1H-pyrrolo[3,2-c]pyridine-6-carboxamide. The title compound can be prepared from the mixture of ethyl 3-(4-chloro-phenoxymethyl)-1-ethyl-1H-pyrrolo[3,2-c]pyridine-6carboxylate and ethy 3-(5-chloro-2-hydroxy-benzyl)-1-ethyl-1H-pyrrolo[3,2-c]pyridine-6-carboxylate in a manner similar to step (e) of example 11. Purification by HPLC can provide the pure title compound.

Example 63

3-(5-Chloro-2-hydroxybenzyl)-1-ethyl-N-hydroxy-1H-pyrrolo[3,2-c]pyridine-6-carboxamide

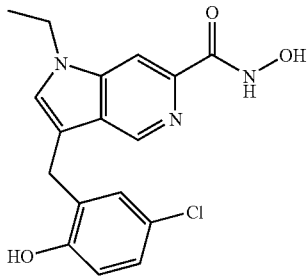

(a) Ethyl 3-(3-chloro-2-hydroxybenzyl)-1-ethyl-1H-pyrrolo[3,2-c]pyridine-6-carboxylate. The title compound can be prepared from ethyl 3-hydroxymethyl-1-ethyl-1H-pyrrolo[3,2-c]pyridine-6-carboxylate and 4-chlorophenol using a methods similar to that set forth in Example 55.

(b) 3-(5-Chloro-2-hydroxybenzyl)-1-ethyl-N-hydroxy-1H-pyrrolo[3,2-c]pyridine-6-carboxamide. The title compound can be prepared from the mixture of ethyl 3-(4-chloro-phenoxymethyl)-1-ethyl-1H-pyrrolo[3,2-c]pyridine-6-carboxylate and ethyl 3-(5-chloro-2-hydroxy-benzyl)-1-ethyl-1H-pyrrolo[3,2-c]pyridine-6-carboxylate in a manner similar to step (e) of Example 11. Purification by HPLC can provide the pure title compound.

Example 64

Integrase Strand-Transfer Scintillation Proximity Assay

Oligonucleotides: Oligonucleotide #1-5'-(biotin) CCCCTTTTAGTCAGTGTGGAAAATCTCTAGCA-3' (SEQ ID NO: 1) and oligonucleotide #2-5'-ACTGCTA-GAGATTTTCCACACTGACTAAAAG-3' (SEQ ID NO: 2), were synthesized by TriLink BioTechnologies, Inc. (San Diego, Calif.). The annealed product represents preprocessed viral ds-DNA derived from the LTR U5 sequence of the viral genome. A ds-DNA control to test for non-specific interactions was made using a 3' di-deoxy derivative of oligonucleotide #1 annealed to oligonucleotide #2. The CA overhang at the 5' end of the non-biotinylated strand of the ds-DNA was created artificially by using a complimentary DNA oligonucleotide shortened by 2 base pairs. This configuration eliminates the requisite 3' processing step of the integrase enzyme prior to the strand-transfer mechanism.

Host ds-DNA was prepared as an unlabeled and [$^3$H]-thymidine labeled product from annealed oligonucleotide #3-5-AAAAAATGACCAAGGGCTAATTCACT-3' (SEQ ID NO: 3), and oligonucleotide #4-5'-AAAAAAAGT-GAATTAGCCCTTGGTCA-3' (SEQ ID NO: 4), both synthesized by TriLink BioTechnologies, Inc. (San Diego, Calif.). The annealed product had overhanging 3' ends of poly(dA). Host DNA was custom radiolabeled by PerkinElmer Life Sciences Inc. (Boston, Mass.) using an enzymatic method with a 12/1 ratio of [methyl-$^3$H]dTTP/cold ds-DNA to yield 5'-blunt end ds-DNA with a specific activity of >900 Ci/mmol. The radiolabeled product was purified using a NENSORB cartridge and stored in stabilized aqueous solution (PerkinElmer). The final radiolabeled product had six [$^3$H]-thymidine nucleotides at both 5' ends of the host ds-DNA.

Reagents: Streptavidin-coated polyvinyltoluene (PVT) SPA beads were purchased from Amersham Pharmacia (Piscataway, N.J.). Cesium chloride was purchased from Shelton Scientific, Inc. (Shelton, Conn.). White polystyrene, flat bottom, non-binding surface 384-well plates were purchased from Corning. All other buffer components were purchased from Sigma (St. Louis, Mo.) unless otherwise indicated.

Enzyme Construction: Full-length HIV-1 integrase (SF1) sequence (amino acids 1-288) (SEQ ID NO: 5) was constructed in a pET 15b vector (Novagen, Madison, Wis.) with mutations outlined by Chen et al., (Chen, C-H. J. et al., PNAS 97: 8233-8238 (2000)) that facilitate solubility of the enzyme and decrease oxidation. The vector contained a T7 promoter, a 6-histidine tag at the amino terminus, and a thrombin cleavage site. Mutations C56S, W131D, F139D, F185K, and C280S were introduced using a QuickChange kit (Stratagene, San Diego, Calif.). The construct was confirmed through DNA sequencing.

Enzyme Purification: The penta-mutant was expressed in *E. coli* BL21 (DE3) cells and induced with 1 mM isopropyl-1 thio-β-D-galactopyranoside (IPTG) when cells reached an optical density between 0.8-1.0 at 600 nm. Cells were lysed in 20 mM HEPES (pH 7.5), 1.5 M NaCl, 5 mM imidazole, and 2 mM 2-mercaptoethanol. The enzyme was purified following standard methods for histidine tagged proteins (Jenkins, T. M. et al., *Journal of Biological Chemistry* 271: 7712-7718 (1996)). Specifically, cell lysate was passed over a Ni-Nta column (Qiagen, Chatsworth, Calif.) with the 6-His tagged integrase protein eluted by adding 250 mM imidazole. A G-25 Sepharose® column (Amersham Pharmacia, Piscataway, N.J.) was used to exchange the buffer prior to thrombin cleavage of the integrase protein and subsequent removal of thrombin using a benzamidine-Sepharose® 6B column. The cleaved 6-His tag was separated from the integrase using a second Ni-Nta column. The integrase was further purified with a heparin-Sepharose® column and a gradient of NaCl (0.4 to 1 M) in 20 mM HEPES (pH 7.5), 400 mM NaCl, and 1 mM DTT buffer. The purified protein was dialyzed against 20 mM HEPES (pH 7.5), 800 mM NaCl, and 1 mM DTT and concentrated by stirred cell ultrafiltration (Millipore, Bedford, Mass.) or Ultra-free spin concentrators (Millipore, Bedford, Mass.) when required.

Viral DNA Bead Preparation: Streptavidin-coated SPA beads were suspended to 20 mg/ml in 25 mM 3-morpholinopropanesulfonic acid (MOPS) (pH 7.2) and 0.1% NaN$_3$. Biotinylated viral DNA was bound to the hydrated SPA beads in a batch process by combining 25 pmoles of ds-DNA to 1 mg of suspended SPA beads (10 μl of 50 μM viral DNA to 1 ml of 20 mg/ml SPA beads). The mixture was incubated at 22° C. for 20 min. with occasional mixing followed by centrifugation at about 2500 rpm for about 10 min. However, the centrifugation speed and time may vary depending upon the particular centrifuge and conditions. The supernatant was removed and the beads suspended to 20 mg/ml in 25 mM MOPS (pH 7.2) and 0.1% NaN$_3$. The viral DNA beads were stable for more than 2 weeks when stored at 4° C. Di-deoxy viral DNA was prepared in an identical manner to yield control di-deoxy viral DNA beads.

Preparation of Integrase-DNA Complex: Assay buffer was made as a 10× stock of 250 mM MOPS (pH 7.2), 250 mM NaCl, 50 mM 3-[(3-cholamidopropyl)dimethylammonio]-1-propanesulfonate (CHAPS), 0.5% (octylphenoxy)polyethoxyethanol (NP40) (IGEPAL-CA) and 0.05% NaN$_3$. Viral DNA beads were diluted to 2.67 mg/ml in 1× assay buffer plus 3 mM MgCl$_2$, 1% DMSO, and 10 mM fresh DTT. Integrase (IN) was pre-complexed to viral DNA beads in a batch process (IN/viral DNA/bead complex) by combining diluted viral DNA beads with integrase at a concentration of 385 nM followed by a minimum incubation time of 15 min. at 22° C. The sample was kept at 22° C. until transferred to the assay wells. Long-term storage at 4° C. was possible, but not routinely applied.

Preparation of Host DNA: Host DNA was prepared to 200 nM as a mixture of unlabeled and [$^3$H]T-labeled host DNA diluted in 1× assay buffer plus 8.5 mM MgCl$_2$ and 15 mM DTT. Typical concentrations were about 10 nM to about 12 nM [$^3$H]T-labeled host DNA and about 188 nM to about 190 nM unlabeled host DNA. The ratio was adjusted relative to enzyme activity and specific activity of the [$^3$H]T-labeled host DNA to generate a SPA assay signal of 2000-3000 CPM in the absence of modulators such as inhibitors.

Strand-transfer Scintillation Proximity Assay: The strand-transfer reaction was carried out in 384-well microtiter plates, though an identical protocol can be used for a 96-well plate format with a final enzymatic reaction volume of 50 μl. Five microliters of compounds or test reagents diluted in 10% DMSO were added to the assay wells followed by the addition of 32.5 μl of the IN/viral-DNA/bead complex. The strand-transfer reaction was initiated by adding 12.5 μl of host DNA with vigorous vortexing of the plates and transferring them to a humidified 37° C. incubator. An incubation time of 50 min. was shown to be within the linear range of the enzymatic reaction in a 384-well plate. Reaction kinetics are faster in a 96-well format. An incubation time of 20 or 50 minutes was used as the time point to evaluate compound inhibitors for assays run in the 96- or 384-well plate format, respectively. The final concentrations of integrase and host DNA in the assay wells were 246 nM and 50 nM, respectively.

The integrase strand-transfer reaction was terminated by adding 35 μl of stop buffer (150 mM EDTA, 90 mM NaOH, and 6 M CsCl) to the wells. Components of the stop buffer function to terminate enzymatic activity (EDTA), dissociate integrase/DNA complexes in addition to separating non-integrated DNA strands (NaOH), and float the SPA beads to the surface of the wells to be in closer range to the PMT detectors of the TopCount® plate-based scintillation counter (PerkinElmer Life Sciences Inc. (Boston, Mass.)). After the addition of stop buffer, the plates were vigorously vortexed, sealed with transparent tape, and allowed to incubate a minimum of 60 min. at 22° C. The assay signal was measured using a TopCounte plate-based scintillation counter with settings optimal for [$^3$H]-PVT SPA beads. The TopCounte program incorporated a quench standardization curve to normalize data for color absorption of the compounds (color quench correction program (QstINT file). Data values for quench-corrected counts per minute (QCPM) were used to quantify integrase activity. Counting time was 30 sec./well for plates processed in HTS mode, and up to 2 min./well for plates containing purified compound.

The di-deoxy viral DNA beads were used to optimize the integrase strand-transfer reaction. The di-deoxy termination of the viral ds-DNA sequence prevented productive integration of viral DNA into the host DNA by integrase. Thus, the assay signal in the presence of di-deoxy viral DNA was a measure of non-specific interactions. Assay parameters were optimized to where reactions with di-deoxy viral DNA beads gave an assay signal closely matched to the true background of the assay. The true background of the assay was defined as a reaction with all assay components (viral DNA and [$^3$H]-host DNA) in the absence of integrase.

Determination of Compound Activity: Compounds were evaluated for integrase inhibitory activity using two different methods. A high-throughput screening method was employed to test combinatorial compound libraries or synthetic compounds that were solvated and transferred to microtiter plates. The percent inhibition of the compound was calculated using the equation (1-((QCPM sample–QCPM min)/(QCPM max–QCPM min)))*100. The min value is the assay signal in the presence of a known inhibitor at a concentration 100-fold higher than the IC$_{50}$ for that compound. The min signal approximates the true background for the assay. The max value is the assay signal obtained for the integrase-mediated activity in the absence of compound.

The IC$_{50}$ values of synthetic and purified combinatorial compounds were also determined. Compounds were prepared in 100% DMSO at 100-fold higher concentrations than desired for testing in assays, followed by dilution of the compounds in 100% DMSO to generate an 8-point titration curve with ½-log dilution intervals. The compound sample was further diluted 10-fold with water and transferred to the assay wells. The percentage inhibition for an inhibitory compound was determined as above with values applied to a nonlinear regression, sigmoidal dose response equation (variable slope) using GraphPad Prism curve fitting software (GraphPad Software, Inc., San Diego, Calif.).

Example 65

HIV-1 Cell Protection Assay

The antiviral activities of potential modulator compounds (test compounds) were determined in HIV-1 cell protection assays using the RF strain of HIV-1, CEM-SS cells, and the XTT dye reduction method (Weislow, O. S. et al., *J. Natl. Cancer Inst.* 81: 577-586 (1989)). Subject cells were infected with HIV-1 RF virus at an moi of 0.025 to 0.819 or mock infected with medium only and added at 2×10$^4$ cells per well into 96 well plates containing half-log dilutions of test compounds. Six days later, 50 µl of XTT (1 mg/ml XTT tetrazolium and 0.02 nM phenazine methosulfate) were added to the wells and the plates were reincubated for four hours. Viability, as determined by the amount of XTT formazan produced, was quantified spectrophotometrically by absorbance at 450 nm.

Data from CPE assays were expressed as the percent of formazan produced in compound-treated cells compared to formazan produced in wells of uninfected, compound-free cells. The fifty percent effective concentration (EC$_{50}$) was calculated as the concentration of compound that affected an increase in the percentage of formazan production in infected, compound-treated cells to 50% of that produced by uninfected, compound-free cells. The 50% cytotoxicity concentration (CC$_{50}$) was calculated as the concentration of compound that decreased the percentage of formazan produced in uninfected, compound-treated cells to 50% of that produced in uninfected, compound-free cells. The therapeutic index was calculated by dividing the cytotoxicity (CC$_{50}$) by the antiviral activity (EC$_{50}$).

We claim:
1. A compound of formula (I),

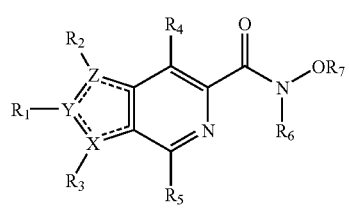

Formula I wherein:
R$_1$ is hydrogen or —C(O)O-ethyl;
R$_2$ is hydrogen, methyl, ethyl, propyl, vinyl, allyl, or benzyl, unsubstituted or substituted with one or more substituents independently selected from the group consisting of:
halogens, —O—, OH, amino, and phenyl, unsubstituted or substituted with one or more substituents selected from the group consisting of:
methyl, ethyl, phenyl, benzyl, 2-phenylethyl, 3-phenylallyl, and 2-phenylvinyl;
R$_3$ is methyl, ethyl, butyl, or benzyl, unsubstituted or substituted with one or more substituents independently selected from the group consisting of:
halogens, OH, methyl, cyclohexyl, —O—, thiadiazole, thiophenyl, and phenoxy, unsubstituted or substituted with one or more substituents independently selected from the group consisting of:
halogens, phenyl, and ethoxy;
R$_4$ is hydrogen, methyl or methoxymethyl;
R$_5$ is hydrogen or methyl;
R$_6$ is hydrogen, methyl, or benzyl;
R$_7$ is hydrogen, methyl, benzyl, phenyl, allyl, or tert-butyl, unsubstituted or substituted with one or more halogens;
X is C or N;
Y is C;
Z is C or N; and
there is a double bond between X and the 6-membered ring and Z and the 6-membered ring;
or between X and Y; or between Y and Z.

2. A compound of formula (I),

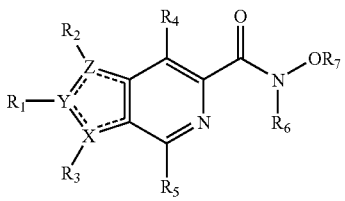

Formula I wherein:

R₁ is hydrogen or —C(O)O-ethyl;

R₂ is selected from hydrogen; hydroxymethyl; methoxymethyl; ethoxymethyl; 2-phenylvinyl; 3-phenylprop-1-enyl; [(2-phenylvinyl)oxy]methyl; dimethylaminomethyl; benzyloxymethyl; 4-fluorobenzyl; 2-phenylvinyl; 2-phenylethyl; 3-phenylpropyl; 2-phenylethoxymethyl; [(phenylprop-2-enyl)oxy]methyl; [(3-phenylallyl)oxy]methyl; methyl; ethyl; and allyl;

R₃ is selected from hydrogen; 2,4-difluorobenzyl; 2,3-difluorobenzyl; 4-fluorobenzyl; 3-chloro-2,6-difluorobenzyl; 3-chloro-5-fluoro-2-hydroxybenzyl; 5-chloro-thiophen-2-ylmethyl; 3-chloro-2-fluorobenzyl; 2,3-dichlorobenzyl; 5-ethoxy-[1,2,3]thiadiazol-4-ylmethyl; 3-methylbutyl; 2-cyclohexylethyl; 2,4-difluorophenoxymethyl; 3,5-difluoro-2-hydroxybenzyl; 2-chloro-4-fluorophenoxymethyl; 3-chloro-5-fluoro-2-hydroxybenzyl; 4-fluorophenoxymethyl; 5-fluoro-2-hydroxybenzyl; 2,3,4-trifluorophenoxymethyl; 3,4,5-trifluoro-2-hydroxybenzyl; 2-chlorophenoxymethyl; and 5-chloro-2-hydroxybenzyl R₄ is hydrogen, methyl or methoxymethyl;

R₅ is hydrogen or methyl;

R₆ is hydrogen, methyl, or benzyl;

R₇ is hydrogen, methyl, benzyl, phenyl, pentafluorobenzyl, allyl, or tert-butyl;

X is C or N;

Y is C;

Z is C or N; and there is a double bond between X and the 6-membered ring and Z and the 6-membered ring; or between X and Y; or between Y and Z.

* * * * *